United States Patent
Wu et al.

(10) Patent No.: US 11,485,735 B2
(45) Date of Patent: Nov. 1, 2022

(54) SELECTIVE CDK4/6 INHIBITOR AND PREPARATION THEREOF

(71) Applicant: Wuxi Shuangliang Biotechnology Co., Ltd., Jiangsu (CN)

(72) Inventors: Jiaquan Wu, Wayland, MA (US); Feng Fan, Jiangsu (CN); Shuai Zhang, Jiangsu (CN); Zhenghua Lu, Jiangsu (CN); Chengchen Wang, Jiangsu (CN); Jian Dong, Jiangsu (CN); Jie Zhang, Jianngsu (CN); Teng Wang, Jiangsu (CN); Xiaoyi Ji, Jiangsu (CN); Minqi Gao, Jiangsu (CN)

(73) Assignee: Wuxi Shuangliang Biotechnology Co., Ltd., Jiangsu (CN)

( * ) Notice: Subject to any disclaimer, the term of this patent is extended or adjusted under 35 U.S.C. 154(b) by 16 days.

(21) Appl. No.: 16/847,487

(22) Filed: Apr. 13, 2020

(65) Prior Publication Data
US 2020/0339572 A1   Oct. 29, 2020

Related U.S. Application Data

(60) Provisional application No. 62/838,689, filed on Apr. 25, 2019.

(51) Int. Cl.
| | |
|---|---|
| *C07D 401/14* | (2006.01) |
| *C07D 471/04* | (2006.01) |
| *A61P 35/00* | (2006.01) |
| *C07D 487/04* | (2006.01) |

(52) U.S. Cl.
CPC ............ *C07D 471/04* (2013.01); *A61P 35/00* (2018.01); *C07D 401/14* (2013.01); *C07D 487/04* (2013.01)

(58) Field of Classification Search
CPC .......................... C07D 401/14; C07D 471/04
See application file for complete search history.

(56) References Cited

FOREIGN PATENT DOCUMENTS

WO    WO 2018/106870    *   6/2018

* cited by examiner

*Primary Examiner* — Brian E McDowell
(74) *Attorney, Agent, or Firm* — Muncy, Geissler, Olds & Lowe, P.C.

(57) ABSTRACT

The present disclosure discloses a compound as represented by formula (I) or a pharmaceutically acceptable salt, a solvate or a stereoisomer thereof, that can be represented by the following structure

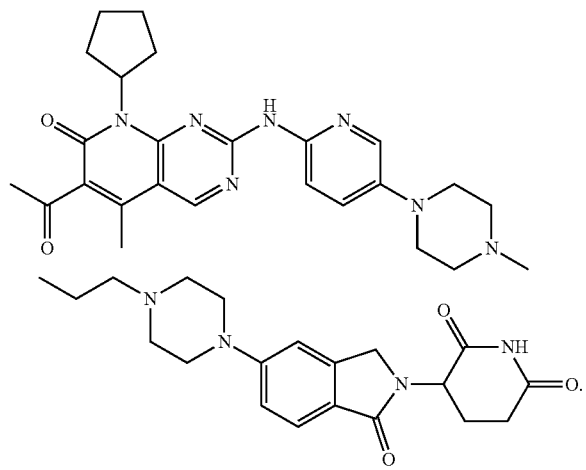

As a selective inhibitor of cyclin-dependent kinase 4/6 (CDK4/6), the compounds of the present disclosure may be used for treating or preventing a disease at least partially modulated by CDK4/6.

8 Claims, No Drawings

SELECTIVE CDK4/6 INHIBITOR AND PREPARATION THEREOF

TECHNICAL FIELD

The present disclosure belongs to the technical field of medicinal chemistry, and particularly relates to a selective CDK4/6 inhibitor and the pharmaceutical composition, pharmaceutical preparation and application thereof.

BACKGROUND

The ubiquitin-proteasome system (UPS) is a main pathway for intracellular protein degradation, which is involved in the degradation of more than 80% of the intracellular proteins. It plays an important role in cell regulation such as gene transcription, growth and development, selective elimination of abnormal proteins, antigen presentation, angiogenesis, tumorigenesis and the like, and is therefore considered to be an important new target for the innovative drug design.

Proteolysis targeting chimera (PROTAC) is a platform technology that induces protein degradation. It comprises three moieties, one end has a structure that targets the target protein, and the other end has a structure that recruits a system for protein degradation. These two ends are linked by a suitable linker. This technique utilizes the ubiquitin-proteasome system which act as a "cleaner" in cell. Ubiquitin is attached to a target protein via ligase, and the target protein is transported into proteasome for degradation.

Cell cycle regulatory factors mainly include cyclin, cyclin-dependent kinase (CDK), and cyclin-dependent kinase inhibitors (CKI). Among these, CDK is a kinase family in which multiple signaling pathways are integrated to control the cell cycle or gene transcription.

CDK is a class of critical cell cycle-regulating protein kinases, and the activation and inactivation of CDK maintain the orderly progression of each phase of the cell cycle. CDK has 13 members, among which CDK4 and CDK6 are important kinases to drive the cell cycle. Relying on the binding to specific cyclin(s), CDK4 and CDK6 promote the phase transition in a cell cycle, initiate DNA synthesis, regulate key functions such as transcription in a cell, and regulate the initiation and progression of each phase of the cell cycle, thereby controlling cell proliferation and apoptosis. CDK binds to cyclin(s) and plays an important role during the transition from Gi phase to S phase in a cell. In cancer cells, the activity of CDK is often uncontrolled and is abnormally high. By selectively inhibiting CDK, cells are arrested in the middle of Gi phase, thereby causing cell arrest and blocking the proliferation of tumor cells. Although the initial response of cells to CDK inhibitors is cell arrest, in some cases, the arrested cells may further senesce and die. As for this type of cancer, CDK inhibitors may achieve the best clinical efficacy.

Therefore, the development of novel CDK4/6 inhibitors has a broad market prospect.

SUMMARY

The present disclosure relates to a novel bifunctional complex (selective CDK4/6 inhibitor) prepared by PROTAC technology as well as the application of the complex.

In a first aspect, the present disclosure provides a compound as represented by formula (I):

PBM-L-PDM     (I)

wherein PBM is a protein binding moiety for CDK4/6, which acts as a structure targeting a target protein and binds to CDK4/6; L is a linking moiety, which links PBM and PDM; and PDM is a protein degradation moiety for CDK4/6, which acts as a structure recruiting a system for protein degradation and gets involved in the degradation of CDK4/6.

Further, in the above-mentioned compound of formula (I), said PBM is

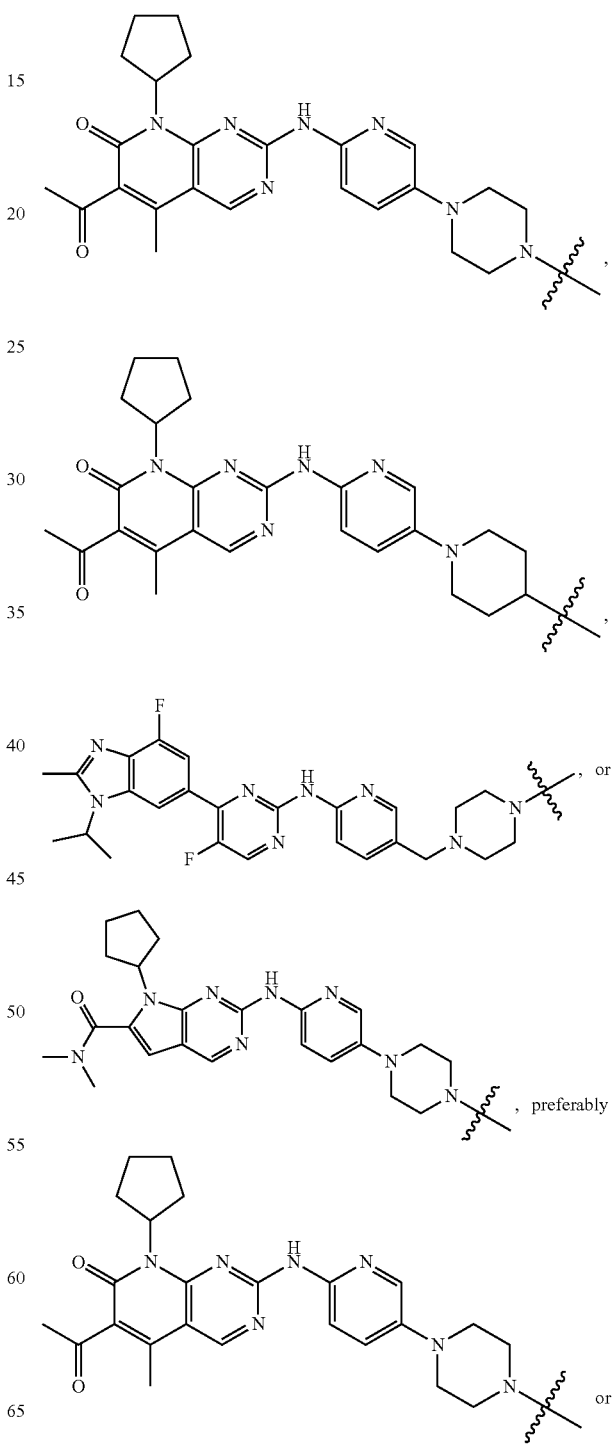

-continued

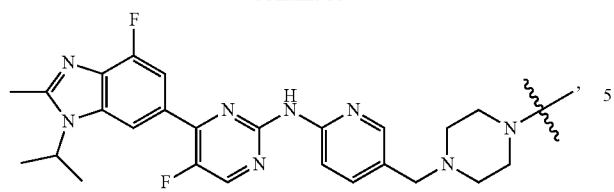

and more preferably

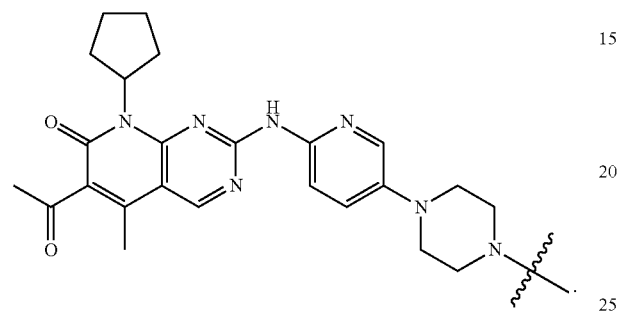

Further, in the above-mentioned compound of formula (I), said L is

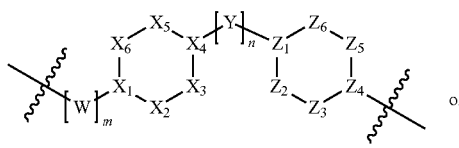  or

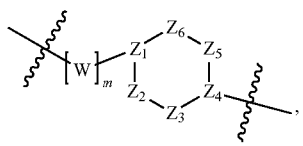

wherein each of W and Y is independently $CH_2$, O, $NHR_1$, $CR_2R_3$, C(=O), C(=S), S(=O), or $S(=O)_2$; if present, each of $R_1$, $R_2$ and $R_3$ is independently hydrogen, linear or branched C1-C6 alkyl optionally substituted with one or more halogens, or C1-C6 alkoxy optionally substituted with one, two or three $R_4$; if present, each $R_4$ is independently hydrogen, halogen, hydroxy, C1-C3 alkyl, or formyl;

each of m and n is independently any integer of 0 to 6; and each of $X_1$, $X_4$, $Z_1$ and $Z_4$ is independently N or CH; each of $X_2$, $X_3$, $X_5$, $X_6$, $Z_2$, $Z_3$, $Z_5$ and $Z_6$ is independently $NR_5$, O, $CR_6R_7$, C(=O), or a covalent bond; if present, each of $R_5$, $R_6$ and $R_7$ is independently hydrogen, linear or branched C1-C6 alkyl optionally substituted with one or more halogens, or C1-C6 alkoxy optionally substituted with one, two or three $R_8$; if present, each $R_8$ is independently hydrogen, halogen, hydroxy, C1-C3 alkyl, or formyl.

Furthermore, in the above-mentioned compound of formula (I), said L is any one of the following structural formulas:

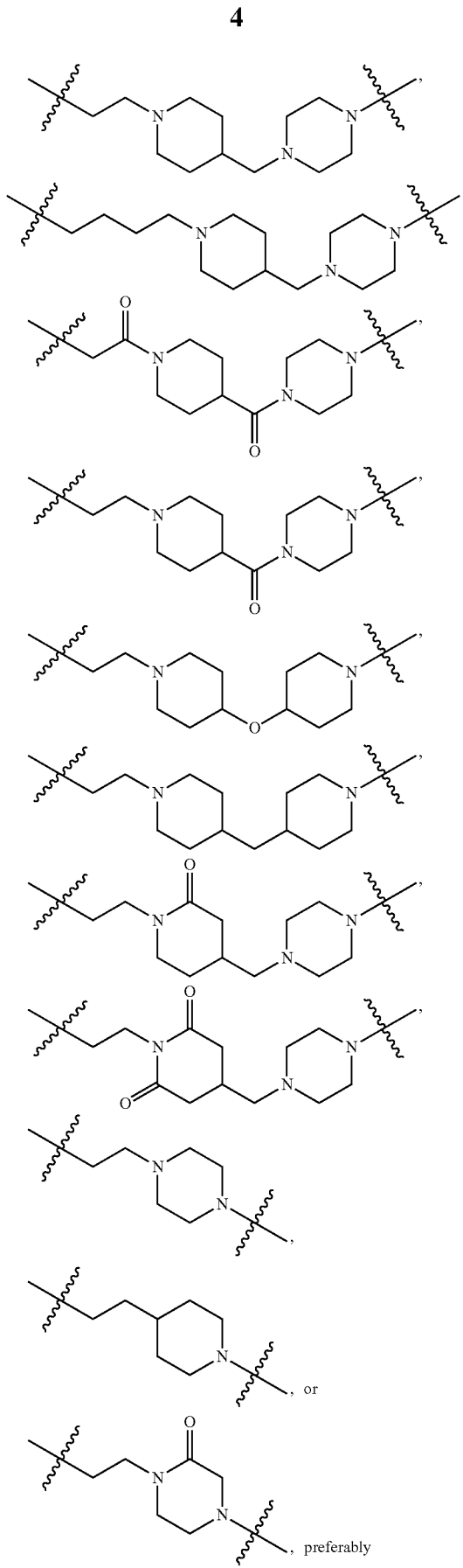

, preferably

-continued

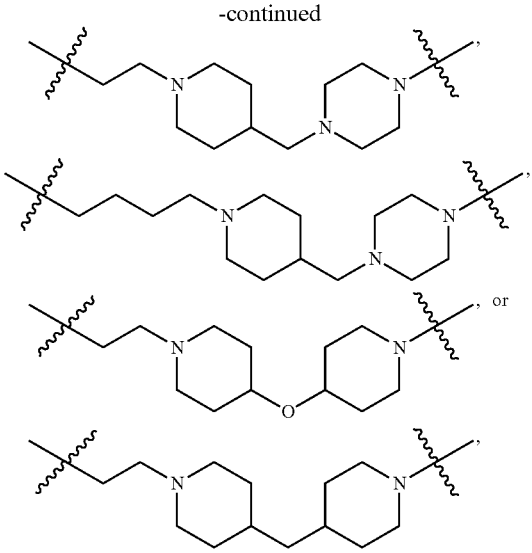

more preferably

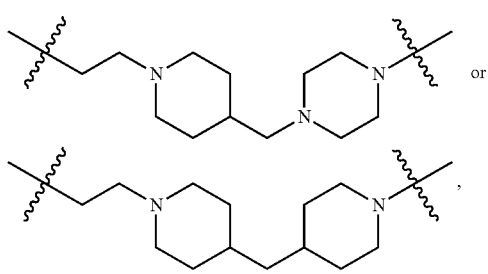

and most preferably

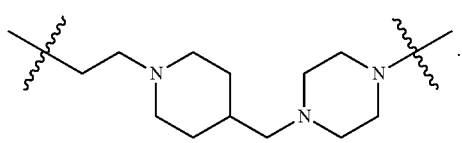 [SMILES: *CCN1CCC(CN2CCN(*)CC2)CC1 ; "."]

Further, in the above-mentioned compound of formula (I), said PDM is

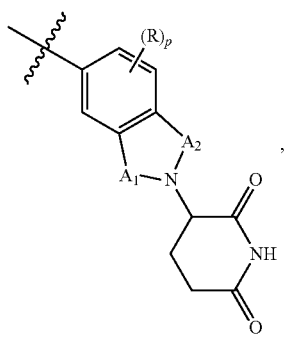

wherein
each R is independently hydrogen, alkyl, haloalkyl, alkoxy, haloalkoxy, cyano, or halogen;
p is 0, 1, 2, or 3; and
each of $A_1$ and $A_2$ is independently $CH_2$ or $C(=O)$.

Furthermore, in the above-mentioned compound of formula (I), said PDM is any one of the following structural formulas:

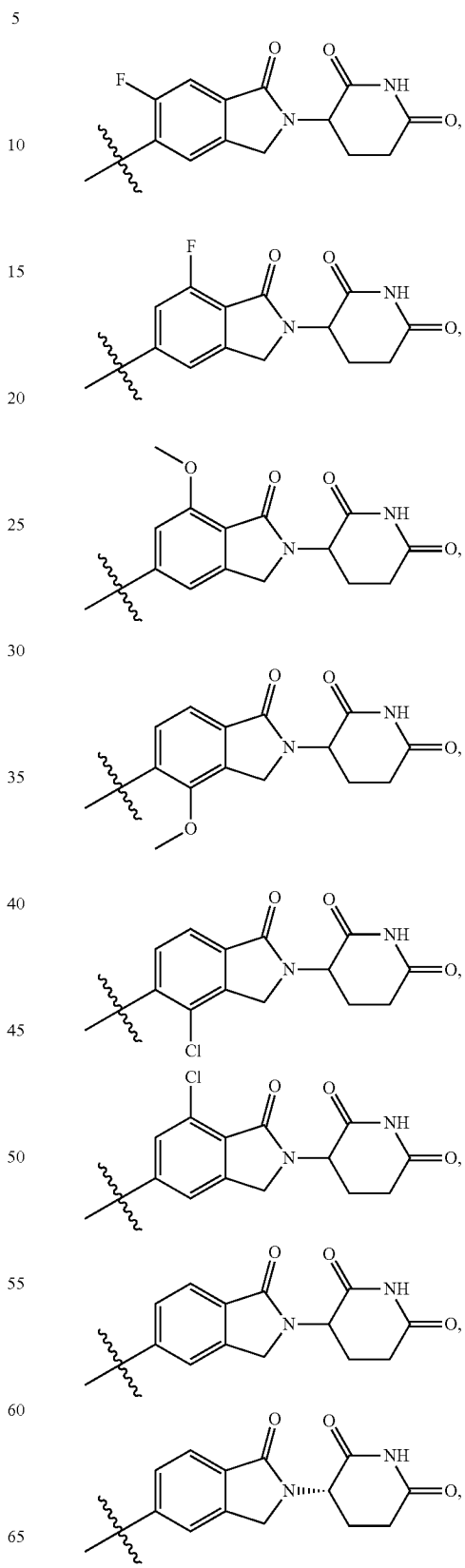

-continued
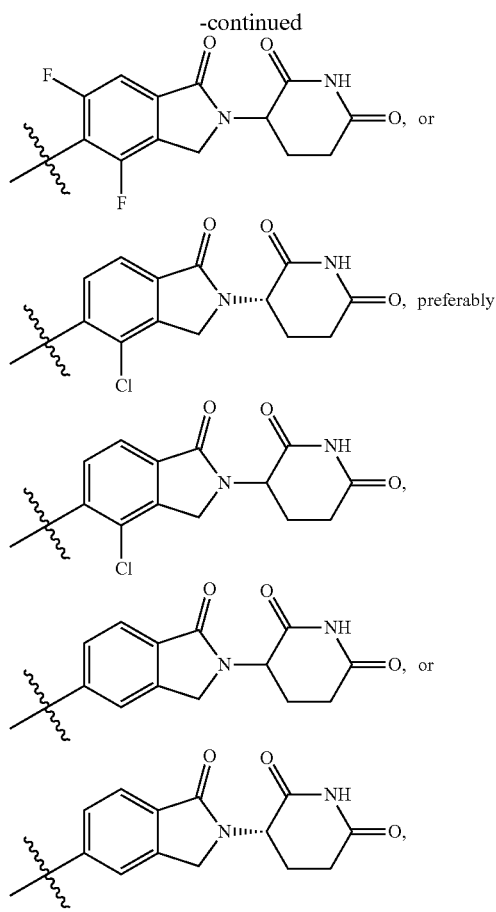
O, or
O, preferably
O,
O, or
O.
and more preferably
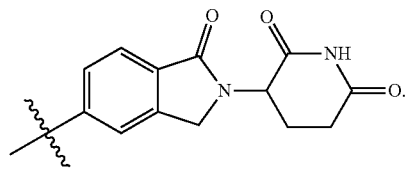 [SMILES: *c1ccc2c(c1)CN(C1CCC(=O)NC1=O)C2=O]
O.
Further, the above-mentioned compound of formula (I) has a structure as represented by formula (I')
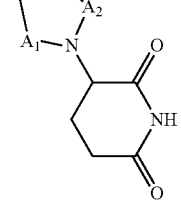 I'
wherein said PBM is
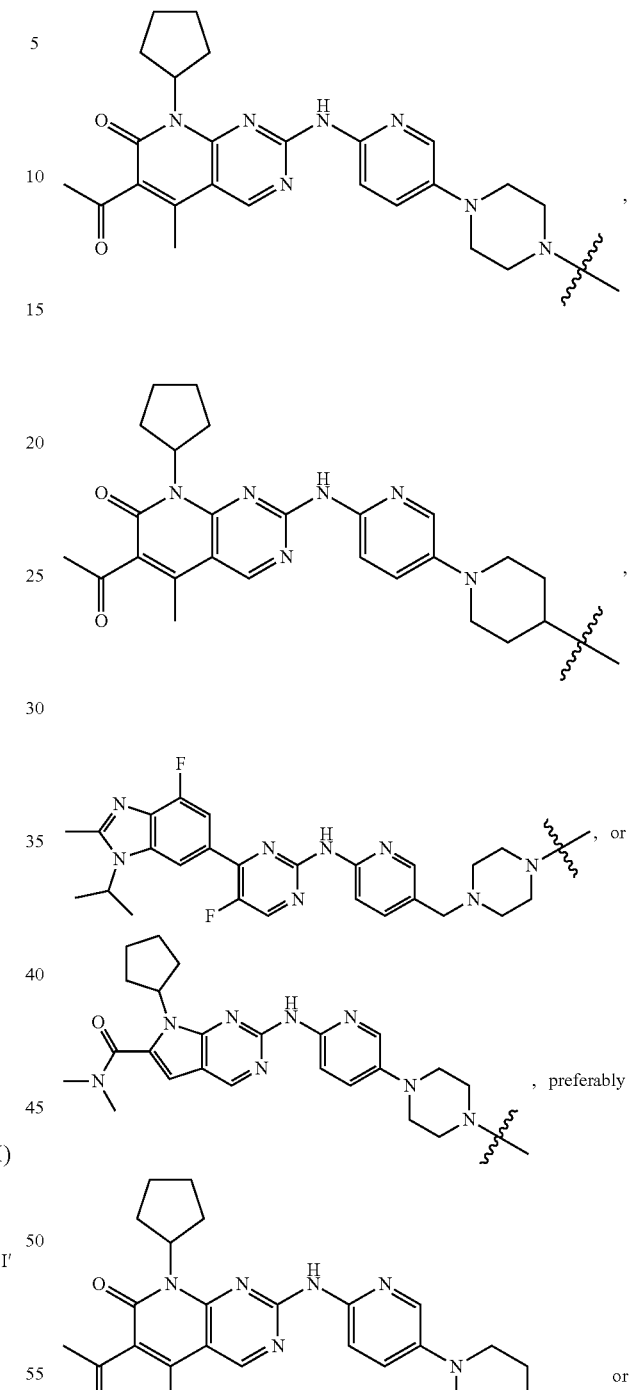
,
,
, or
, preferably
or
, and more preferably

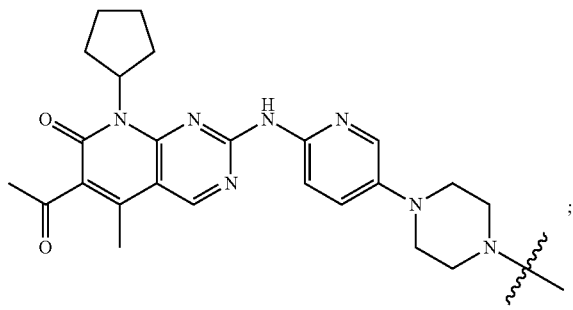 [SMILES: *N1CCN(c2ccc(Nc3ncc4c(C)c(C(C)=O)c(=O)n(C5CCCC5)c4n3)nc2)CC1]

each of W and Y is independently O, CH$_2$, or C(=O), preferably O or CH$_2$;

each of m and n is independently 0, 1, 2, 3, or 4, preferably 1, 2, or 4;

each of X$_1$, X$_4$, Z$_1$ and Z$_4$ is independently N or CH; each of X$_2$, X$_3$, X$_5$, X$_6$, Z$_2$, Z$_3$, Z$_5$ and Z$_6$ is independently O, CH$_2$, C(=O), or a covalent bond, preferably CH$_2$ or C(=O);

each R is independently hydrogen, halogen, or alkoxy, preferably hydrogen or halogen;

p is 0, 1, or 2, preferably 0 or 1; and each of A$_1$ and A$_2$ is independently CH$_2$ or C(=O), preferably, A$_1$ is CH$_2$ and A$_2$ is C(=O).

Furthermore, the above-mentioned compound of formula (I) has any one of the structures as represented by formula (I-1) to formula (I-12):

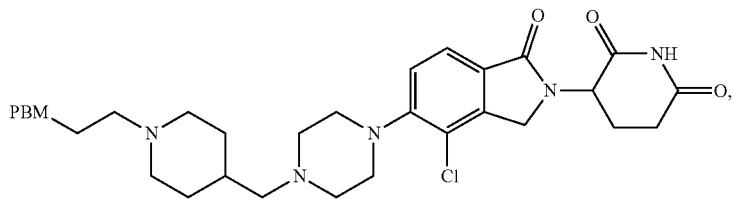

I-1

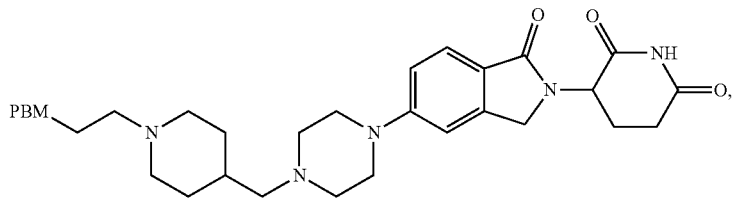

I-2

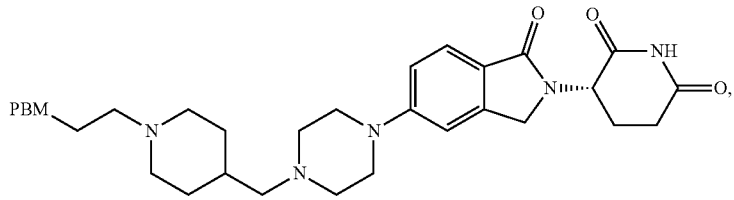

I-3

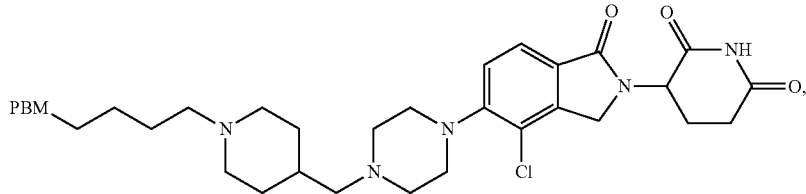

I-4

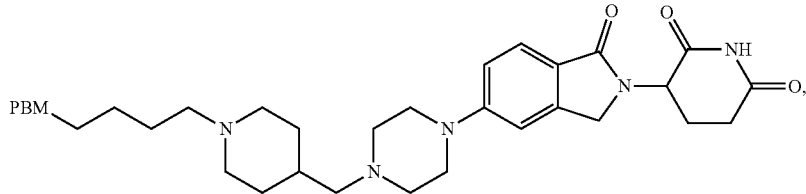

I-5

I-6
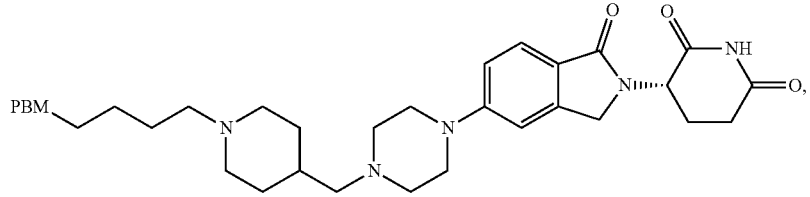

I-7
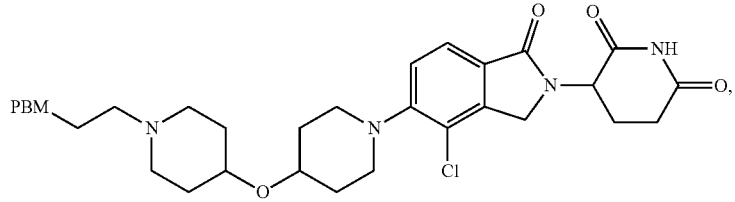

I-8
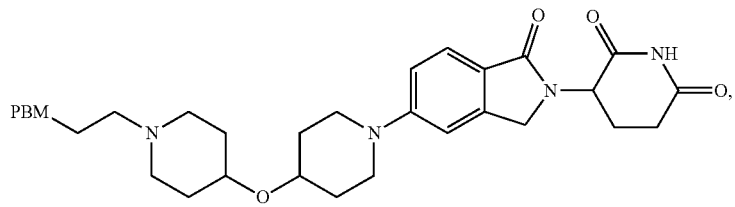

I-9
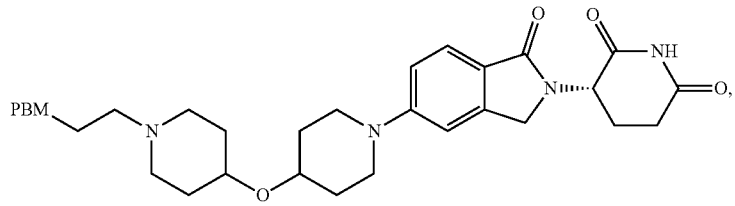

I-10
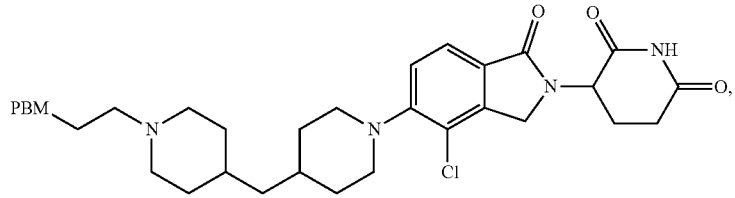

I-11
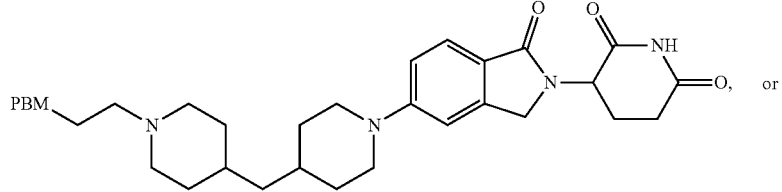
or

I-12
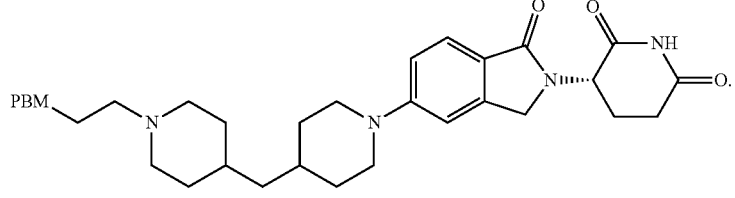

In a second aspect, the present disclosure provides a pharmaceutical composition comprising the above-mentioned compound, or a pharmaceutically acceptable salt, a solvate or an isomer thereof.

In a third aspect, the present disclosure provides a pharmaceutical preparation comprising the above-mentioned compound or a pharmaceutically acceptable salt, a solvate or an isomer thereof, or the above-mentioned pharmaceutical composition, and one or more pharmaceutically acceptable excipients.

In a fourth aspect, the present disclosure provides use of the above-mentioned compound or a pharmaceutically acceptable salt, a solvate or an isomer thereof, or the above-mentioned pharmaceutical composition, in preparation of a pharmaceutical preparation for preventing and/or treating a disease at least partially modulated by CDK4/6.

Further, in the above-mentioned use, the disease at least partially modulated by CDK4/6 includes breast cancer, rectal cancer, colon cancer, lung cancer, multiple myeloma, liver cancer, and ovarian cancer.

In a fifth aspect, the present disclosure provides a method for preventing and/or treating a disease at least partially modulated by CDK4/6, comprising administering a therapeutically and/or prophylactically effective amount of the above-mentioned compound or a pharmaceutically acceptable salt, a solvate or an isomer thereof, or the above-mentioned pharmaceutical composition, or the above-mentioned pharmaceutical preparation, to a subject in need thereof.

Further, in the above-mentioned method, the disease at least partially modulated by CDK4/6 includes breast cancer, rectal cancer, colon cancer, lung cancer, multiple myeloma, liver cancer, and ovarian cancer.

DETAILED DESCRIPTION

The experiment is divided into two main parts: the synthesis and preparation of CDK inhibitors and the verification of activities in in-vitro experiments.

1. Synthesis and Preparation of CDK4/6 Inhibitors

The present disclosure will be further exemplified and illustrated in the following Examples. These Examples are only for the purpose of illustrating the present disclosure, but do not limit the present disclosure in any way. The following synthesis methods are all preferred embodiments.

1) The synthesis route of Compound 3 was illustrated as below:

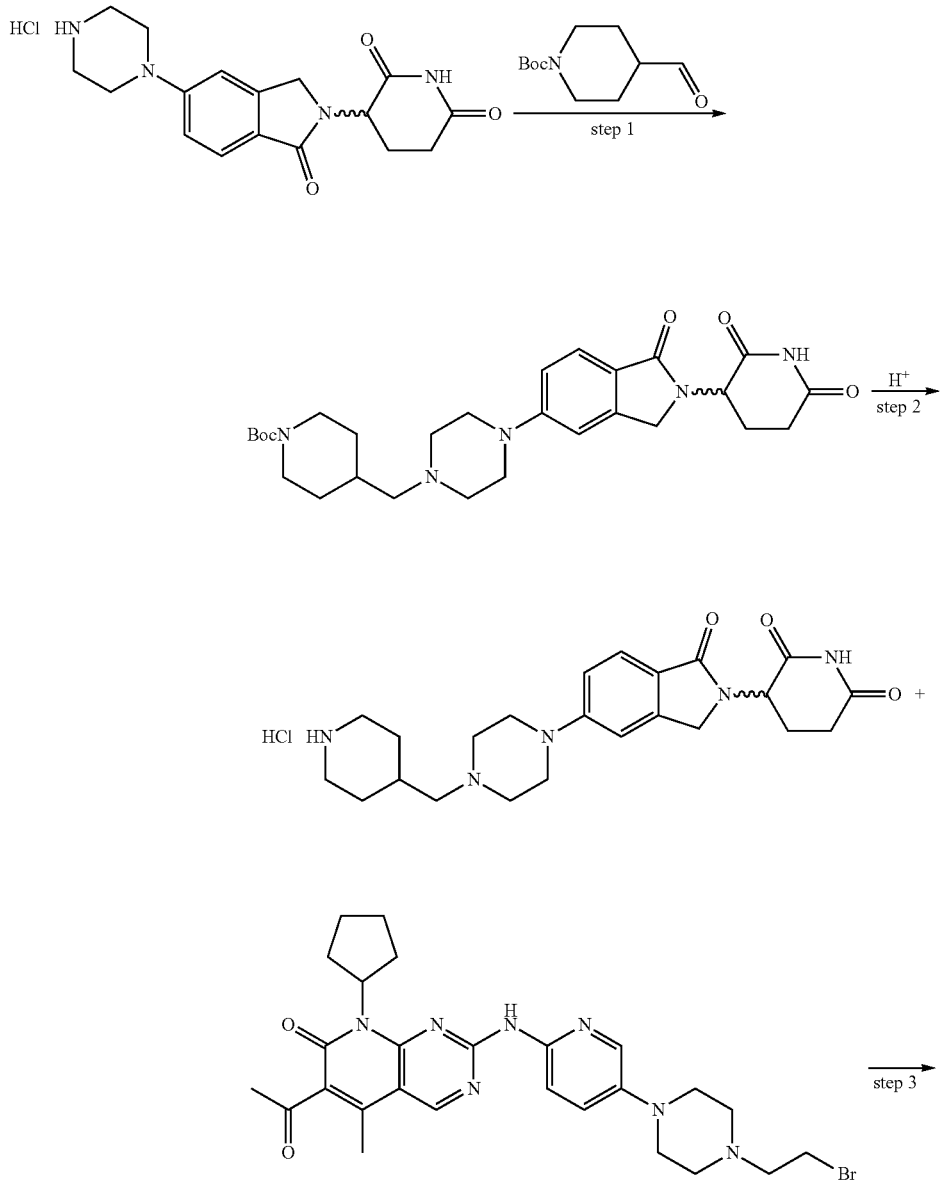

-continued

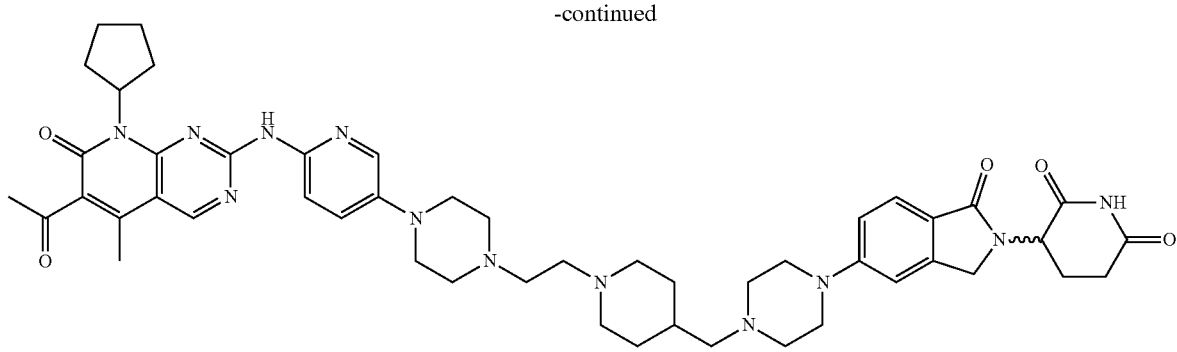

Step 1: Preparation of tert-butyl 4-(4-(2-(2,6-dioxopiperidin-3-yl)-1-oxoisoindolin-5-yl)piperazin-1-yl)methyl)piperidine-1-carboxylate 3-(1-Oxo-5-(piperazin-1-yl)isoindolin-2-yl)piperidine-2,6-dione hydrochloride (100 mg, 0.274 mmol) was dissolved in 1,2-dichloroethane (10 mL) and acetic acid (1 mL). Tert-butyl 4-formylpiperidine-1-carboxylate (117 mg, 0.55 mmol) and sodium triacetoxyborohydride (174 mg, 0.82 mmol) were added to the mixed solution. After being stirred overnight at room temperature, the reaction solution was concentrated and then purified by column chromatography to yield a product of 90 mg. [M+H]$^+$=526.3.

Step 2: Preparation of 3-(1-oxo-5-(4-(piperidin-4-ylmethyl)piperazin-1-yl)isoindolin-2-yl)piperidine-2,6-dione hydrochloride Tert-butyl 4-(4-(2-(2,6-dioxopiperidin-3-yl)-1-oxoisoindolin-5-yl)piperazin-1-yl)methyl)piperidine-1-carboxylate (90 mg, 0.17 mmol) was dissolved in ethyl acetate (2 mL), and a 4 M solution of hydrogen chloride in ethyl acetate (10 mL) was added. After the reaction solution was stirred overnight at room temperature, the solvent of the reaction solution was removed under reduced pressure and then the resultant was directly used in the next step. [M+H]+=426.2.

Step 3: Preparation of 3-(5-(4-((1-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperidin-4-yl)methyl)piperazin-1-yl)-1-oxoisoindolin-2-yl)piperidine-2,6-dione 6-Acetyl-2-((5-(4-(2-bromoethyl)piperazin-1-yl)pyridin-2-yl)amino)-8-cyclopentyl-5-methylpyrido[2,3-d]pyrimidin-7(8H)-one (20 mg, 0.036 mmol) was dissolved in acetonitrile (10 mL). Diisopropylethylamine (18.6 mg, 0.144 mmol), potassium iodide (3.3 mg, 0.02 mmol) and 3-(1-oxo-5-(4-(piperidin-4-ylmethyl)piperazin-1-yl)isoindolin-2-yl)piperidine-2,6-dione hydrochloride (33 mg, 0.072 mmol) were added to the solution. After being stirred overnight at 85° C., the reaction solution was concentrated and then purified by column chromatography to yield a product of 11 mg. $^1$HNMR (400 MHz, CDCl$_3$) δ 8.82 (s, 1H), 8.15 (d, J=8.8 Hz, 1H), 8.03 (s, 1H), 7.72 (d, J=8.4 Hz, 1H), 7.35-7.32 (m, 1H), 6.98 (d, J=8.8 Hz, 1H), 6.88 (s, 1H), 5.92-5.83 (m, 1H), 5.20-5.15 (m, 1H), 4.43-4.24 (m, 2H), 3.31 (s, 4H), 3.21 (s, 4H), 2.91-2.71 (m, 10H), 2.57-2.55 (m, 7H), 2.37-2.05 (m, 19H), 1.89-1.87 (m, 4H); [M+H]+= 899.5.

W was methylene, the chain length of the unit consisting of the same was variable, and m was equal to 2 or 4; the ring consisting of X1 to X6 was piperidine ring; Y was methylene, n was equal to 1; the ring consisting of Z1 to Z6 was piperazine ring; and R was absent or halogen.

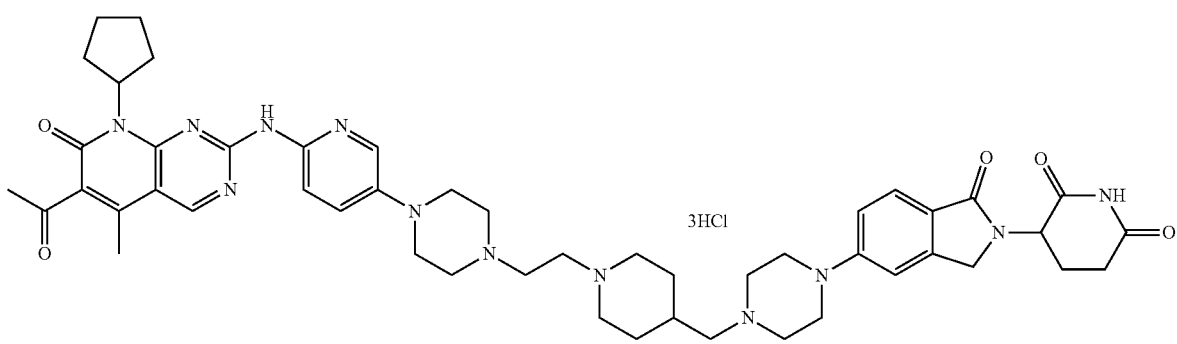 [SMILES: CC(=O)c1c(C)c2cnc(Nc3ccc(N4CCN(CCN5CCC(CN6CCN(c7ccc8c(c7)CN(C7CCC(=O)NC7=O)C8=O)CC6)CC5)CC4)cn3)nc2n(C2CCCC2)c1=O]

5
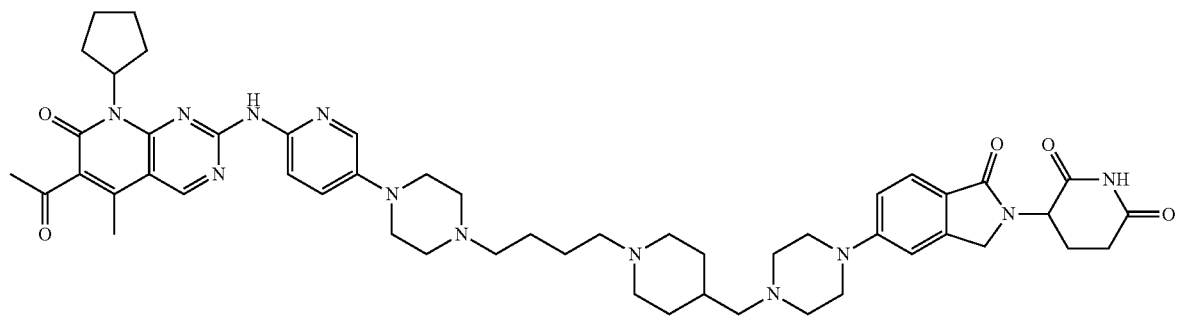 [SMILES: CC(=O)c1c(C)c2cnc(Nc3ccc(N4CCN(CCCCN5CCC(CN6CCN(c7ccc8c(c7)CN(C7CCC(=O)NC7=O)C8=O)CC6)CC5)CC4)cn3)nc2n(C2CCCC2)c1=O]
26
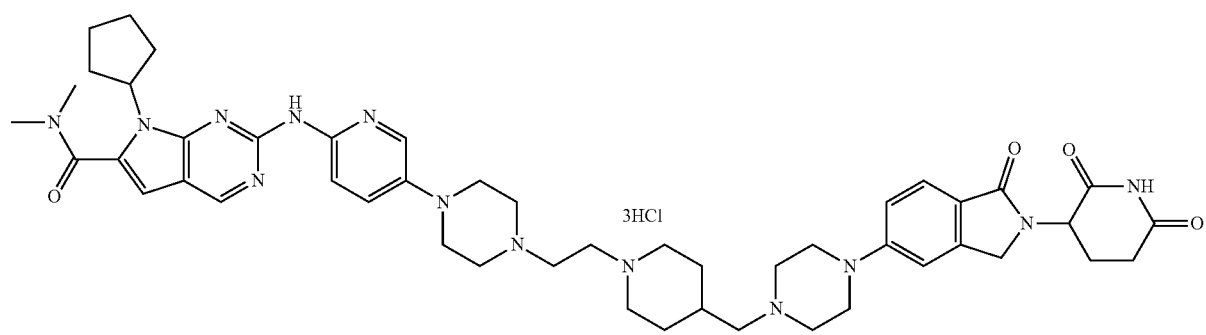
29
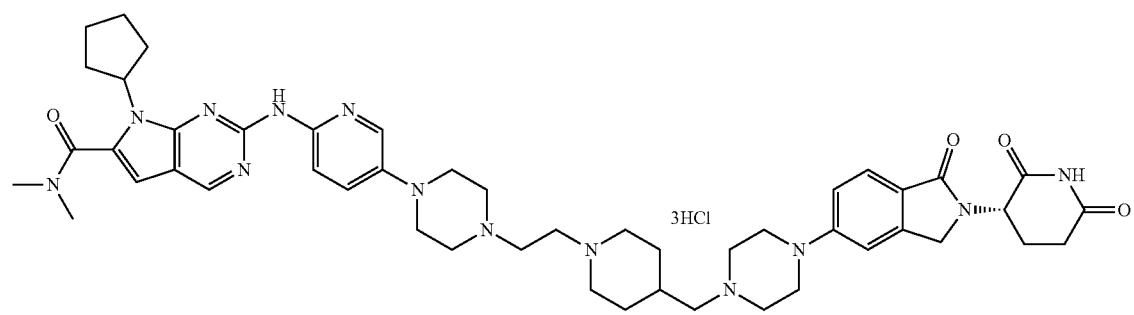
34
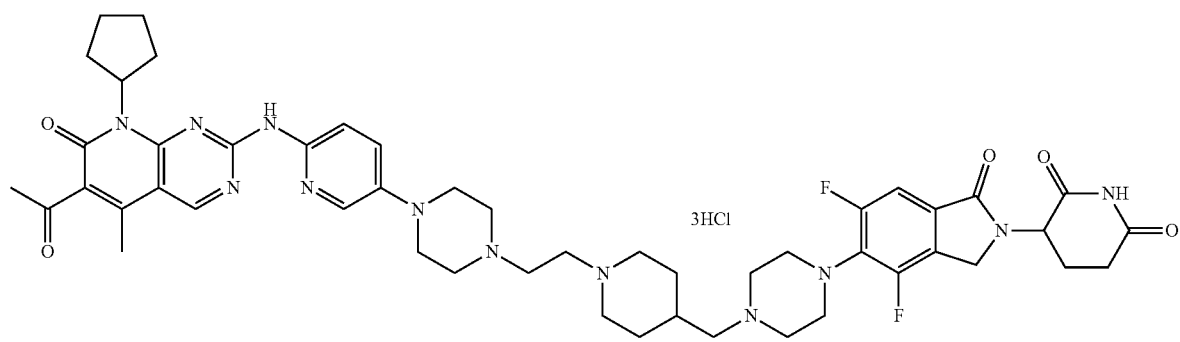

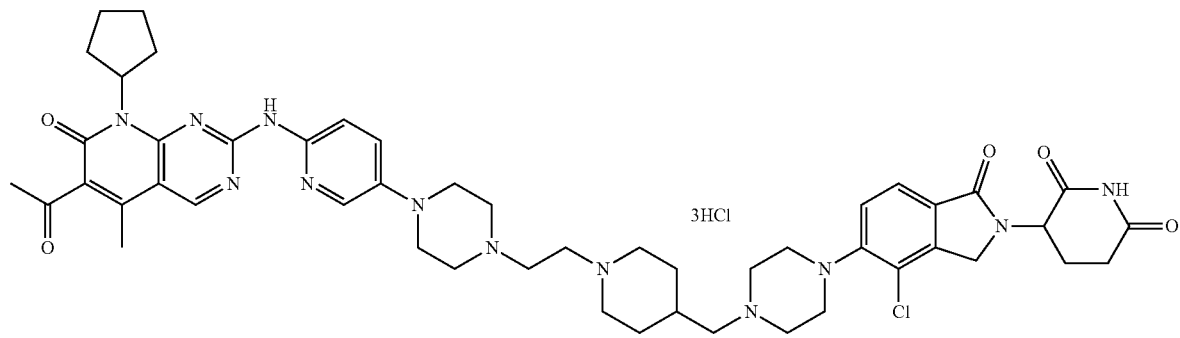
36
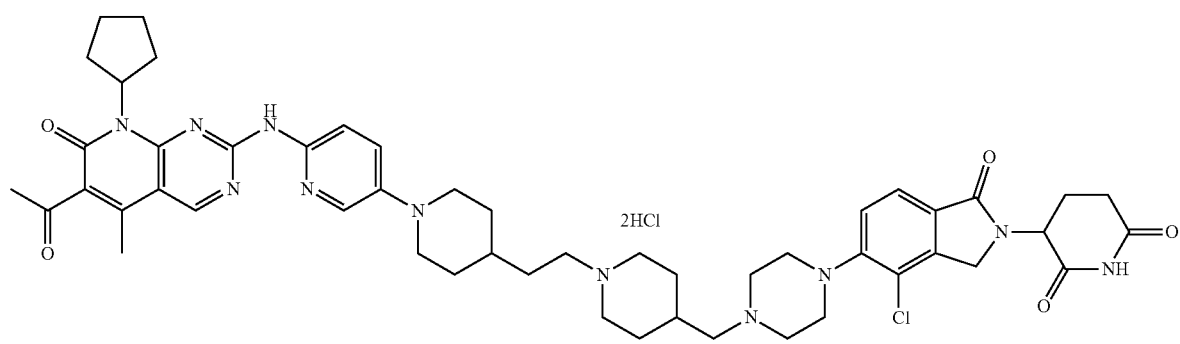
44
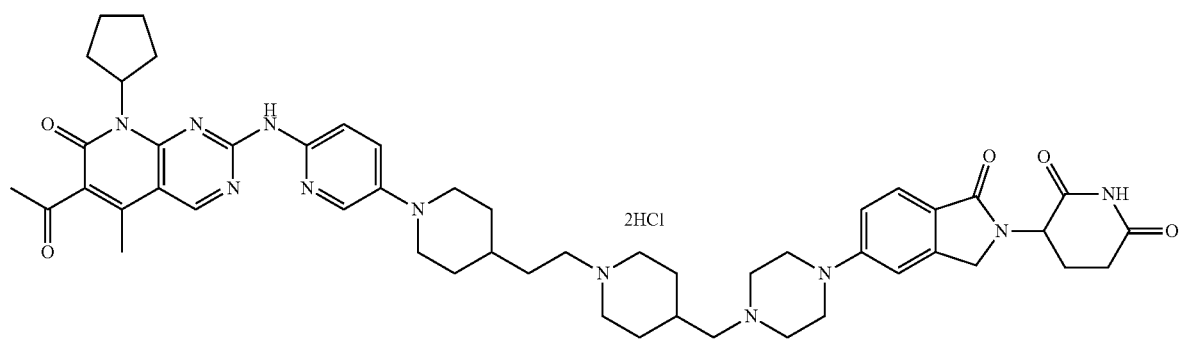
45
2) The synthesis route of Compound 4 was illustrated as below:
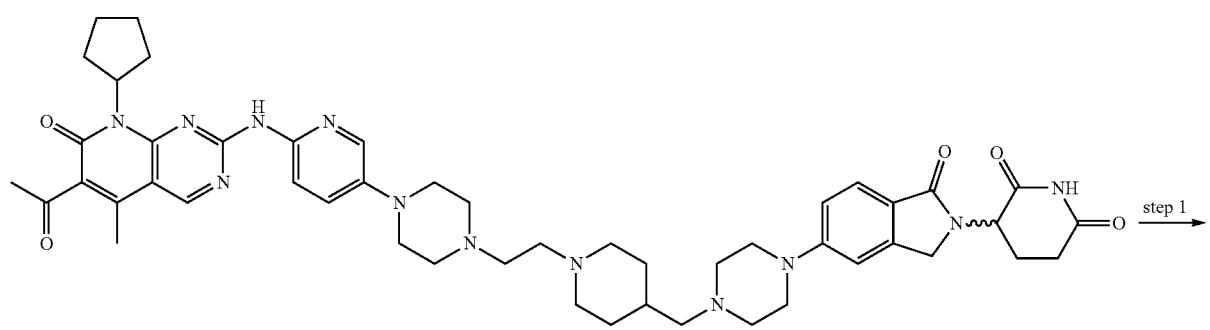

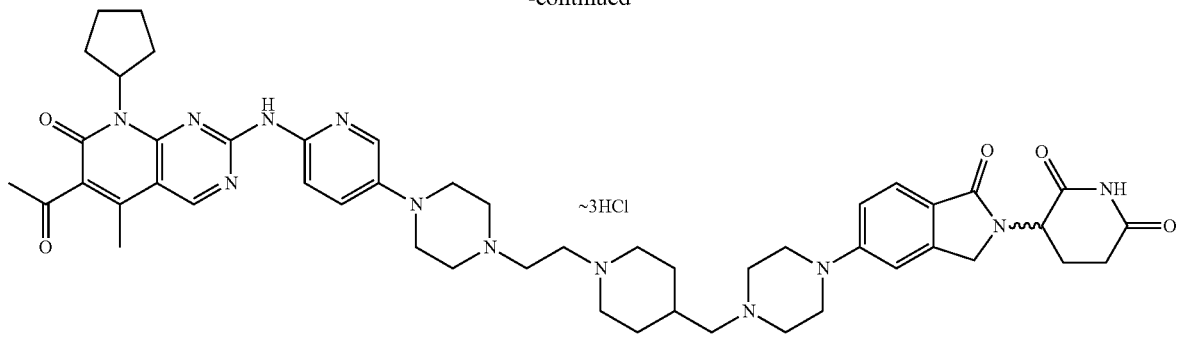

~3HCl

Step 1: Preparation of 3-(5-(4-((1-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperidin-4-yl)methyl)piperazin-1-yl)-1-oxoisoindolin-2-yl)piperidine-2,6-dione trihydrochloride 3-(5-(4-((1-(2-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)ethyl)piperidin-4-yl)methyl)piperazin-1-yl)-1-oxoisoindolin-2-yl)piperidine-2,6-dione (22 mg, 0.024 mmol) was dissolved in methanol (2 mL), and a 4 M solution of hydrogen chloride in methanol (10 mL) was added. After being stirred overnight at room temperature, the reaction solution was concentrated and dried by a rotary evaporator under reduced pressure to yield a product of 23 mg. $^1$HNMR (400 MHz, CDCl$_3$) δ 11.18-11.02 (m, 3H), 10.97 (s, 1H), 9.03 (s, 1H), 8.15-8.14 (m, 1H), 7.94-7.88 (m, 2H), 7.61 (d, J=8.4 Hz, 1H), 7.20-7.16 (m, 2H), 5.88-5.84 (m, 1H), 5.10-5.05 (m, 1H), 4.40-4.23 (m, 2H), 4.01-3.98 (m, 4H), 3.30-2.89 (m, 16H), 2.68-2.58 (m, 2H), 2.45-2.36 (m, 9H), 2.26-2.18 (m, 6H), 2.01-1.81 (m, 8H), 1.64-1.61 (m, 4H). [M+H]$^+$=899.5.

3) The synthesis route of Compound 5 was illustrated as below:

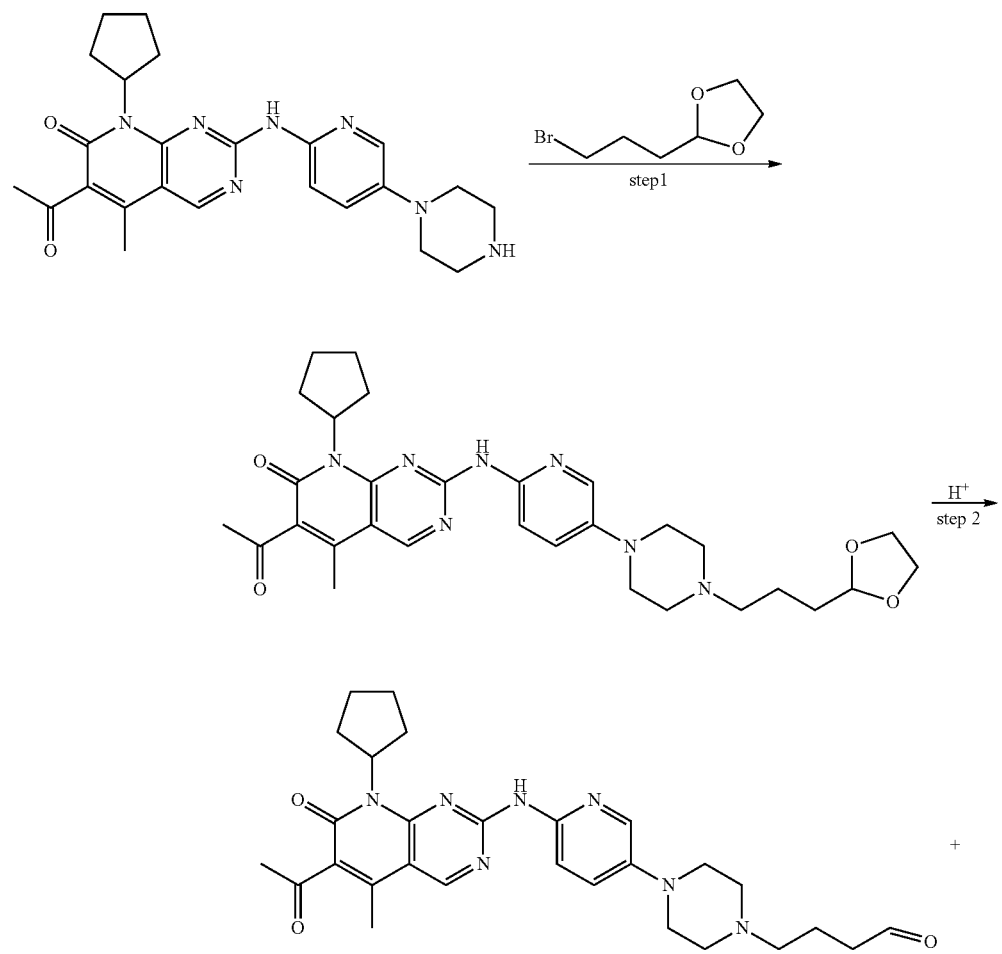

-continued

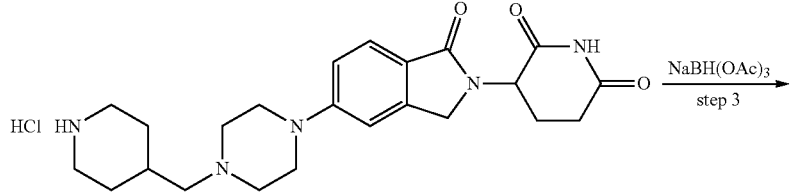

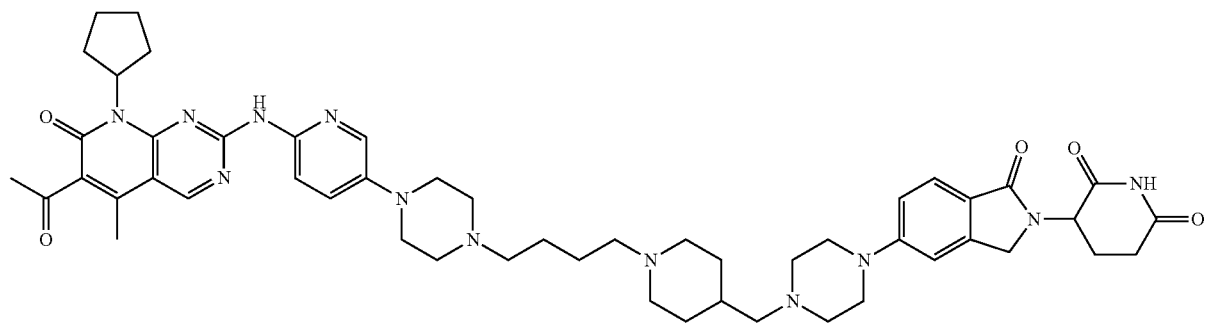

Step 1: Preparation of 2-((5-(4-(3-(1,3-dioxolan-2-yl)propyl)piperazin-1-yl)pyridin-2-yl)amino)-6-acetyl-8-cyclopentyl-5-methylpyrido[2,3-d]pyrimidin-7(8H)-one Palbociclib (1.36 g, 3 mmol) was dissolved in dimethylformamide (50 mL). Diisopropylethylamine (775 mg, 6 mmol) and 2-(3-bromopropyl)-1,3-dioxolane (700 mg, 3.6 mmol) were added to the solution. After being stirred overnight at 60° C., the reaction solution was diluted with ethyl acetate, washed with saline, dried and then purified by column chromatography to yield a product of 1.6 g. [M+H]$^+$=562.3.

Step 2: Preparation of 4-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)butanal 2-((5-(4-(3-(1,3-Dioxolan-2-yl)propyl)piperazin-1-yl)pyridin-2-yl)amino)-6-acetyl-8-cyclopentyl-5-methylpyrido[2,3-d]pyrimidin-7(8H)-one (150 mg, 0.27 mmol) was dissolved in tetrahydrofuran (5 mL). 10% hydrochloric acid solution (5 mL) was added to the solution and the resulting reaction solution was stirred at 60° C. for 3 h. The reaction solution was adjusted to pH 9 and then extracted with dichloromethane. The organic phase was washed with saturated saline, dried and then purified by column chromatography to yield a product of 120 mg. [M+H]$^+$=518.3.

Step 3: Preparation of 3-(5-(4-((1-(4-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)butyl)piperidin-4-yl)methyl)piperazin-1-yl)-1-oxoisoindolin-2-yl)piperidine-2,6-dione 4-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)butanal (120 mg, 0.2 mmol) was dissolved in 1,2-dichloroethane (5 mL) and acetic acid (0.5 mL). 3-(1-Oxo-5-(4-(piperidin-4-ylmethyl)piperazin-1-yl)isoindolin-2-yl)piperidine-2,6-dione hydrochloride (78 mg, 0.17 mmol) and sodium triacetoxyborohydride (127 mg, 0.6 mmol) were added to the mixed solution. After being stirred overnight at room temperature, the solvent of the reaction solution was removed by evaporation. Then, the resultant was purified by column chromatography to yield a product of 5 mg. $^1$HNMR (400 MHz, CDCl$_3$) δ 8.81 (s, 1H), 8.16 (d, J=8.4 Hz, 1H), 8.03 (d, J=2.8 Hz, 1H), 7.73 (d, J=8.4 Hz, 1H), 7.37-7.34 (m, 1H), 7.00-6.97 (m, 1H), 6.88 (s, 1H), 5.92-5.83 (m, 1H), 5.20-5.15 (m, 1H), 4.44-4.25 (m, 2H), 3.30-3.24 (m, 8H), 2.70 (s, 4H), 2.58-2.53 (m, 9H), 2.38-2.33 (m, 9H), 2.05-1.89 (m, 19H), 1.72-1.65 (m, 4H); [M+H]$^+$=927.6.

4) The synthesis route of Compound 26 was illustrated as below:

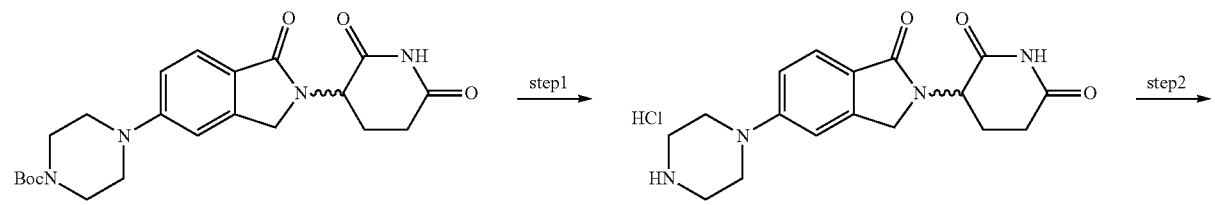

-continued

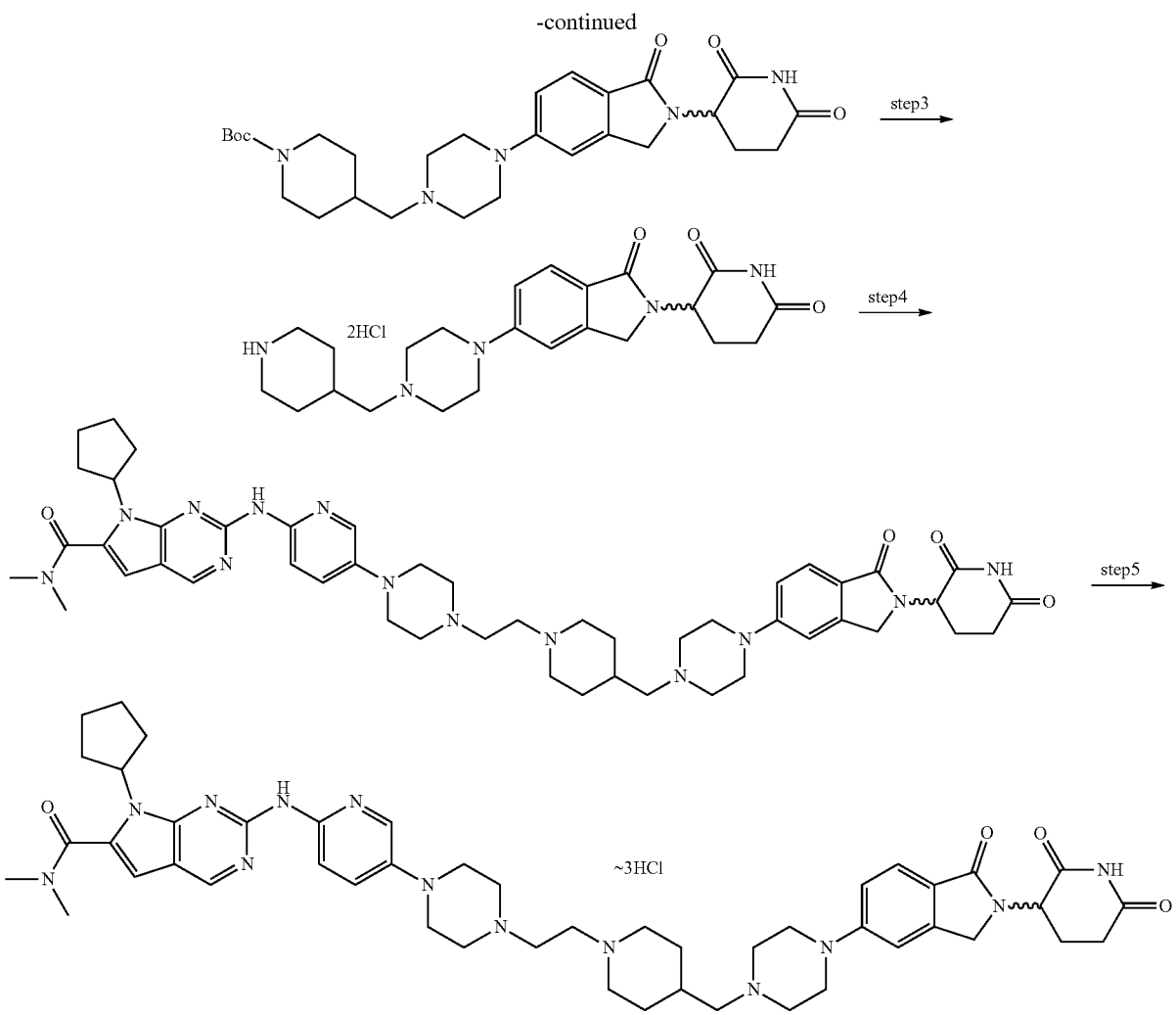

Step 1: Preparation of 3-(1-oxo-5-(piperazin-1-yl)isoindolin-2-yl)piperidine-2,6-dione hydrochloride Tert-butyl 4-(2-(2,6-dioxopiperidin-3-yl)-1-oxoisoindolin-5-yl)piperazin-1-carboxylate (240 mg, 0.56 mmol) was dissolved in methanol (5 mL), and a solution of hydrogen chloride in methanol (20 mL) was added. The mixture was reacted overnight at room temperature and dried by a rotary evaporator to yield a crude product of 200 mg, which was directly used in the next step. [M+H]$^+$=329.2.

Step 2: Preparation of tert-butyl 4-((4-(2-(2,6-dioxopiperidin-3-yl)-1-oxoisoindolin-5-yl)piperazin-1-yl)methyl)piperidine-1-carboxylate 3-(1-Oxo-5-(piperazin-1-yl)isoindolin-2-yl)piperidine-2,6-dione hydrochloride (200 mg, 0.55 mmol) was dissolved in 1,2-dichloroethane (10 mL). A catalytic amount of acetic acid, tert-butyl 4-formylpiperidine-1-carboxylate (117 mg, 0.55 mmol) and sodium triacetoxyborohydride (1.16 g, 5.5 mmol) were added. After the mixture was reacted overnight at room temperature, the reaction solution was concentrated and then purified by column chromatography to yield a product of 100 mg. [M+H]$^+$=526.3.

Step 3: Preparation of 3-(1-oxo-5-(4-(piperidin-4-ylmethyl)piperazin-1-yl)isoindolin-2-yl)piperidine-2,6-dione dihydrochloride Tert-butyl 4-((4-(2-(2,6-dioxopiperidin-3-yl)-1-oxoisoindolin-5-yl)piperazin-1-yl)methyl)piperidine-1-carboxylate (100 mg, 0.19 mmol) was dissolved in methanol (5 mL), and a solution of hydrogen chloride in methanol (10 mL) was added. The mixture was reacted overnight at room temperature and concentrated to yield a crude product of 100 mg, which was directly used in the next step. [M+H]$^+$=426.3.

Step 4: Preparation of 7-cyclopentyl-2-((5-(4-(2-(4-((4-(2-(2,6-dioxopiperidin-3-yl)-1-oxoisoindolin-5-yl)piperazin-1-yl)methyl)piperidin-1-yl)ethyl)piperazin-1-yl)pyridin-2-yl)amino)-N,N-dimethyl-7H-pyrrolo[2,3-d]pyrimidin-6-amide 3-(1-Oxo-5-(4-(piperidin-4-ylmethyl)piperazin-1-yl)isoindolin-2-yl)piperidine-2,6-dione dihydrochloride (100 mg) was dissolved in acetonitrile (10 mL), and 2-((5-(4-(2-bromoethyl)piperazin-1-yl)pyridin-2-yl)amino)-7-cyclopentyl-N,N-dimethyl-7H-pyrrolo[2,3-d]pyrimidin-6-amide (103 mg, 0.19 mmol) and diisopropylethylamine (52 mg, 0.4 mmol) were added. The mixture was reacted overnight at Step 5: Preparation of 7-cyclopentyl-2-((5-(4-(2-(4-((4-(2-(2,6-dioxopiperidin-3-yl)-1-oxoisoindolin-5-yl)piperazin-1-yl)methyl)piperidin-1-yl)ethyl)piperazin-1-yl)pyridin-2-yl)amino)-N,N-dimethyl-7H-pyrrolo[2,3-d]pyrimidin-6-amide trihydrochloride 7-Cyclopentyl-2-((5-(4-(2-(4-((4-(2-(2,6-dioxopiperidin-3-yl)-1-oxoisoindolin-5-yl)piperazin-1-yl)methyl)piperidin-1-yl)ethyl)piperazin-1-yl)pyridin-2-yl)amino)-N,N-dimethyl-7H-pyrrolo[2,3-d]pyrimidin-6-amide (9 mg, 0.01 mmol) was dissolved in methanol (2 mL), and a solution of hydrogen chloride in methanol (5 mL) was added. The mixture was reacted overnight at room temperature and concentrated to yield a product of 9 mg. $^1$HNMR (400 MHz, d$_6$-DMSO) δ 11.42 (brs, 1H), 11.06 (brs, 1H), 10.96 (s, 1H), 9.02 (s, 1H), 8.10-8.02 (m, 2H), 7.68-7.59 (m, 2H), 7.22-7.16 (m, 4H), 6.85 (s, 1H), 5.35-5.32 (m, 1H), 5.10-5.05 (m, 1H), 4.84-4.80 (m, 1H), 4.40-4.23 (m, 2H), 3.18-2.92 (m, 22H), 2.63-2.58 (m, 2H), 2.42-2.17 (m, 12H), 2.04-1.99 (m, 12H). [M+H]$^+$=886.5.

5) The synthesis route of Compound 29 was illustrated as below:

80° C., concentrated and then purified by column chromatography to yield a product of 9 mg. [M+H]$^+$=886.5.

Step 1: Preparation of (S)-7-cyclopentyl-2-((5-(4-(2-(4-((4-(2-(2,6-dioxopiperidin-3-yl)-1-oxoisoindolin-5-yl)piperazin-1-yl)methyl)piperidin-1-yl)ethyl)piperazin-1-yl)pyridin-2-yl)amino)-N,N-dimethyl-7H-pyrrolo[2,3-d]pyrimidin-6-amide (S)-3-(1-oxo-5-(4-(piperidin-4-ylmethyl)piperazin-1-yl)isoindolin-2-yl)piperidine-2,6-dione dihydrochloride (150 mg) was dissolved in acetonitrile (10 mL), and 2-((5-(4-(2-bromoethyl)piperazin-1-yl)pyridin-2-yl)amino)-7-cyclopentyl-N,N-dimethyl-7H-pyrrolo[2,3-d]pyrimidin-6-amide (150 mg, 0.28 mmol) and diisopropylethylamine (77 mg, 0.6 mmol) were added. The mixture was reacted overnight at 80° C., concentrated and then purified by column chromatography to yield a product of 25 mg. [M+H]$^+$=886.5.

Step 2: Preparation of (S)-7-cyclopentyl-2-((5-(4-(2-(4-((4-(2-(2,6-dioxopiperidin-3-yl)-1-oxoisoindolin-5-yl)piperazin-1-yl)methyl)piperidin-1-yl)ethyl)piperazin-1-yl)pyridin-2-yl)amino)-N,N-dimethyl-7H-pyrrolo[2,3-d]pyrimidin-6-amide trihydrochloride (S)-7-cyclopentyl-2-((5-(4-(2-(4-((4-(2-(2,6-dioxopiperidin-3-yl)-1-oxoisoindolin-5-yl)piperazin-1-yl)methyl)pip-

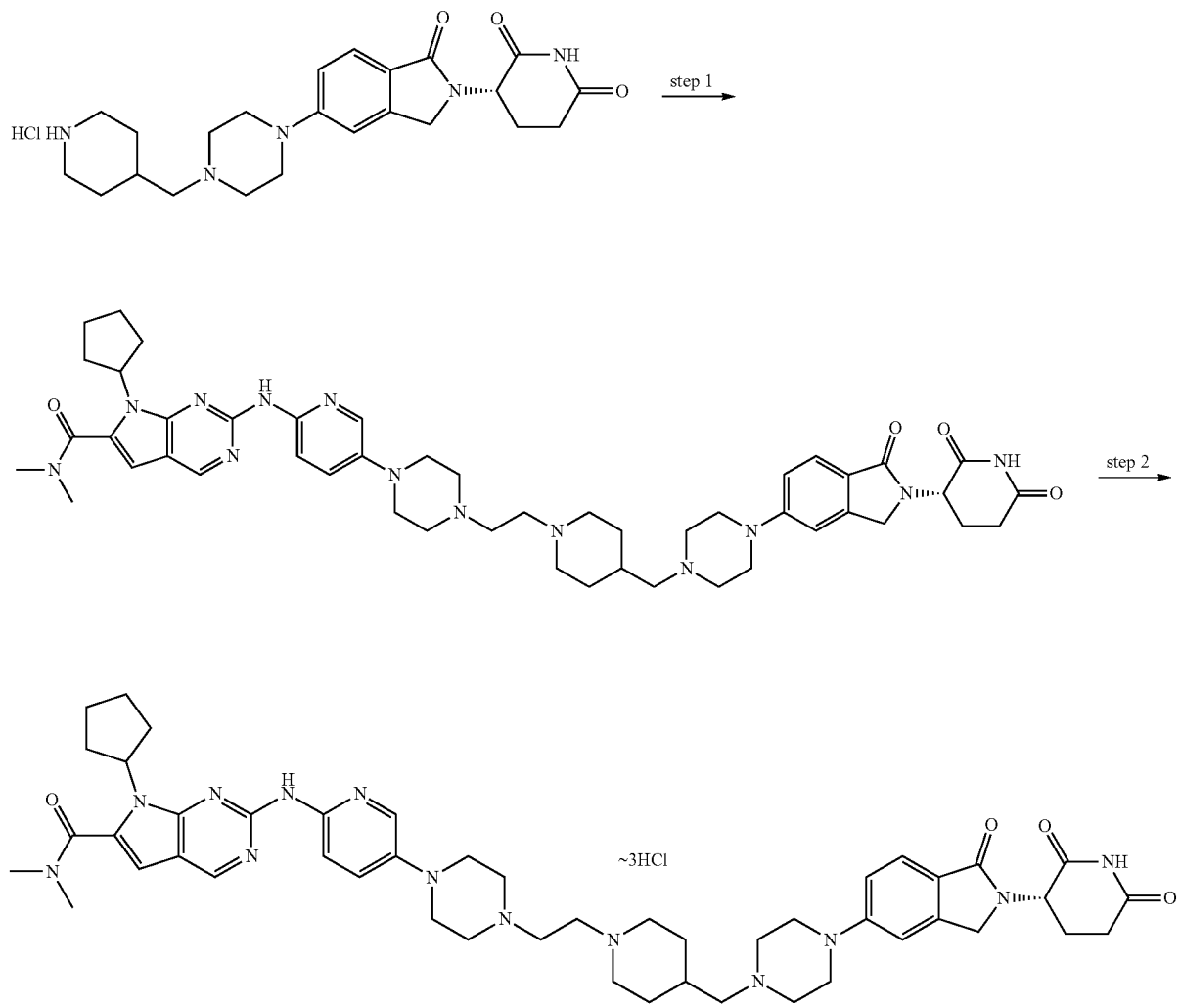

eridin-1-yl)ethyl)piperazin-1-yl)pyridin-2-yl)amino)-N,N-dimethyl-7H-pyrrolo[2,3-d]pyrimidin-6-amide (25 mg, 0.03 mmol) was dissolved in methanol (2 mL), and a solution of hydrogen chloride in methanol (5 mL) was added. The mixture was reacted overnight at room temperature and concentrated to yield a product of 25 mg. $^1$HNMR (400 MHz, d$_6$-DMSO) δ 11.5 (brs, 1H), 11.2 (brs, 1H), 10.96 (s, 1H), 10.7 (brs, 1H), 9.02 (s, 1H), 8.10-8.02 (m, 2H), 7.68-7.59 (m, 2H), 7.22-7.16 (m, 4H), 6.87 (s, 1H), 5.35-5.32 (m, 1H), 5.10-5.05 (m, 1H), 4.84-4.80 (m, 1H), 4.40-4.23 (m, 2H), 3.18-2.92 (m, 22H), 2.63-2.58 (m, 2H), 2.42-2.17 (m, 12H), 2.04-1.99 (m, 12H). [M+H]$^+$=886.5.

6) The synthesis route of Compound 34 was illustrated as below:

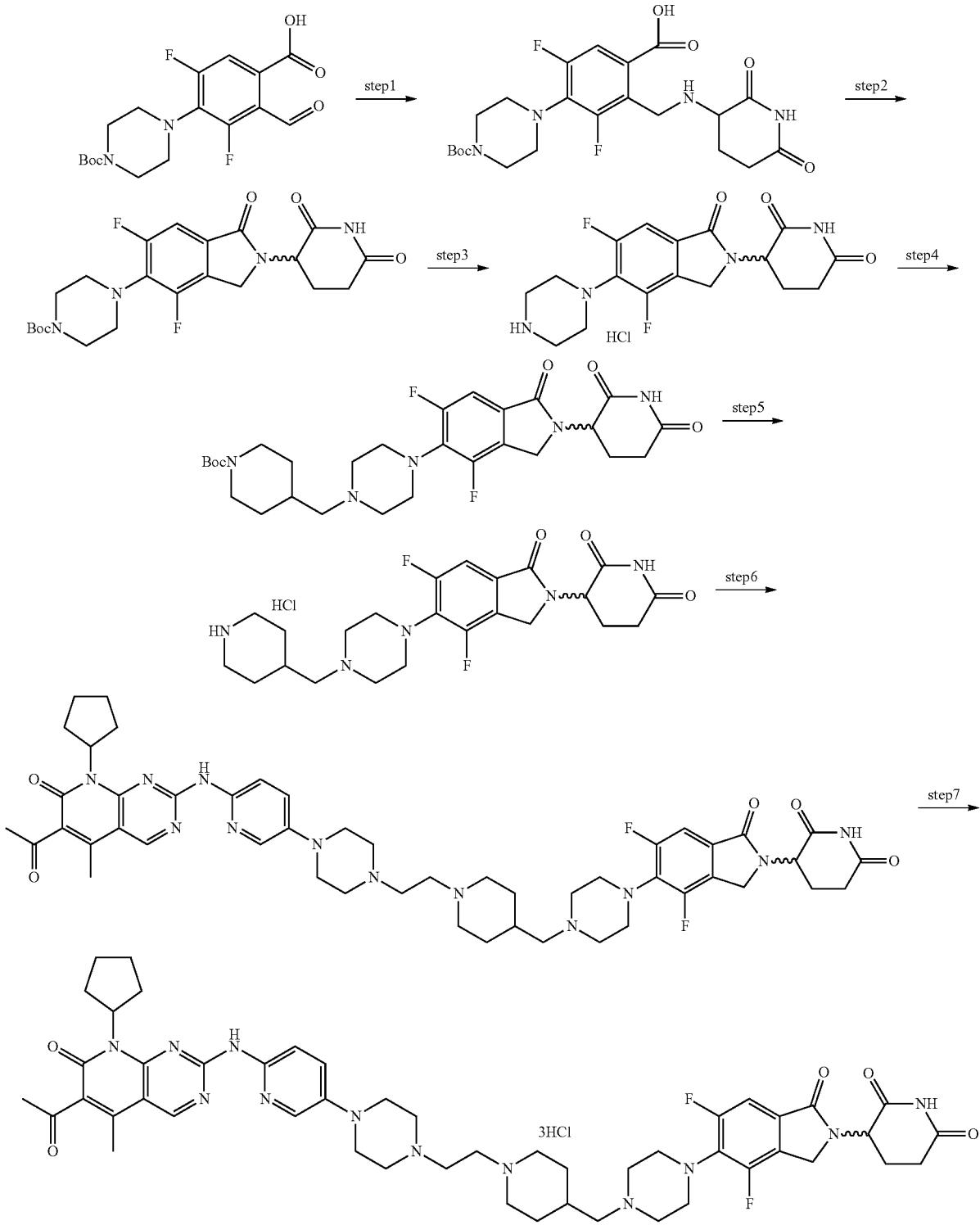

Step 1: Preparation of 4-(4-(tert-butoxycarbonyl) piperazin-1-yl)-2-(((2,6-dioxopiperidin-3-yl)amino) methyl)-3,5-difluorobenzoic acid 4-(4-(Tert-butoxycarbonyl)piperazin-1-yl)-3,5-difluoro-2-formylbenzoic acid (2.5 g, 6.75 mmol) was dissolved in 1,2-dichloroethane (100 mL), and 3-aminopiperidine-2,6-dione hydrochloride (1.15 g, 7 mmol) and sodium triacetoxyborohydride (7.4 g, 35 mmol) were added. The mixture was reacted overnight at room temperature, concentrated and then purified by column chromatography to yield a product of 1.5 g. [M+H]$^+$=483.2.

Step 2: Preparation of tert-butyl 4-(2-(2,6-dioxopiperidin-3-yl)-4,6-difluoro-1-oxoisoindolin-5-yl)piperazine-1-carboxylate 4-(4-(Tert-butoxycarbonyl)piperazin-1-yl)-2-(((2,6-dioxopiperidin-3-yl)amino)methyl)-3, 5-difluorobenzoic acid (1.5 g, 3.1 mmol) was dissolved in dichloromethane (100 mL), and HATU (1.2 g, 3.1 mmol) and triethylamine (400 mg, 4 mmol) were added. The mixture was reacted overnight at room temperature, concentrated and then purified by column chromatography to yield a product of 230 mg. [M+H]$^+$=465.2.

Step 3: Preparation of 3-(4,6-difluoro-1-oxo-5-(piperazin-1-yl)isoindolin-2-yl)piperidine-2,6-dione hydrochloride Tert-butyl 4-(2-(2,6-dioxopiperidin-3-yl)-4,6-difluoro-1-oxoisoindolin-5-yl)piperazine-1-carboxylate (230 mg, 0.5 mmol) was dissolved in methanol (5 mL), and a solution of hydrogen chloride in methanol (20 mL) was added. The mixture was reacted overnight at room temperature and concentrated to yield a product of 200 mg. [M+H]$^+$=365.2.

Step 4: Preparation of tert-butyl 4-((4-(2-(2,6-dioxopiperidin-3-yl)-4,6-difluoro-1-oxoisoindolin-5-yl)piperazin-1-yl)methyl)piperidine-1-carboxylate 3-(4,6-Difluoro-1-oxo-5-(piperazin-1-yl)isoindolin-2-yl)piperidine-2,6-dione hydrochloride (200 mg, 0.5 mmol) was dissolved in 1,2-dichloroethane (10 mL), and tert-butyl 4-formylpiperidine-1-carboxylate (213 mg, 1 mmol) and sodium triacetoxyborohydride (1 g, 5 mmol) were added. The mixture was reacted overnight at room temperature, concentrated and then purified by column chromatography to yield a product of 300 mg. [M+H]$^+$=562.3.

Step 5: Preparation of 3-(4,6-difluoro-1-oxo-5-(4-(piperidin-4-ylmethyl)piperazin-1-yl)isoindolin-2-yl)piperidine-2,6-dione hydrochloride Tert-butyl 4-((4-(2-(2,6-dioxopiperidin-3-yl)-4,6-difluoro-1-oxoisoindolin-5-yl)piperazin-1-yl)methyl)piperidine-1-carboxylate (100 mg, 0.18 mmol) was dissolved in methanol (10 mL), and a solution of hydrogen chloride in methanol (50 mL) was added. The mixture was reacted overnight at room temperature and concentrated to yield a crude product of 100 mg. [M+H]$^+$=462.3.

Step 6: Preparation of 3-(5-(4-((1-(2-(4-(6-((6-acetyl-8-cyclopentyl-5-methyl-7-oxo-7,8-dihydropyrido[2,3-d]pyrimidin-2-yl)amino)pyridin-3-yl) piperazin-1-yl)ethyl)piperidin-4-yl)methyl) piperazin-1-yl)-4,6-difluoro-1-oxoisoindolin-2-yl) piperidine-2,6-dione 3-(4,6-Difluoro-1-oxo-5-(4-(piperidin-4-ylmethyl)piperazin-1-yl)isoindolin-2-yl)piperidine-2,6-dione hydrochloride (100 mg, 0.2 mmol) was dissolved in acetonitrile (30 mL), and 6-acetyl-2-((5-(4-(2-bromoethyl)piperazin-1-yl)pyridin-2-yl)amino)-8-cyclopentyl-5-methylpyrido[2,3-d]pyrimidin-7(8H)-one (222 mg, 0.4 mmol) and diisopropylethylamine (129 mg, 1 mmol) were added. The mixture was reacted overnight at 80° C., concentrated and then purified by column chromatography to yield a product of 12 mg. [M+H]$^+$=935.5.

Step 7: Preparation of 3-(5-(4-((1-(2-(4-(6-((6-acetyl-8-cyclopentyl-5-methyl-7-oxo-7,8-dihydropyrido[2,3-d]pyrimidin-2-yl)amino)pyridin-3-yl) piperazin-1-yl)ethyl)piperidin-4-yl)methyl) piperazin-1-yl)-4,6-difluoro-1-oxoisoindolin-2-yl) piperidine-2,6-dione trihydrochloride 3-(5-(4-((1-(2-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)ethyl)piperidin-4-yl)methyl)piperazin-1-yl)-4,6-difluoro-1-oxoisoindolin-2-yl)piperidine-2,6-dione (12 mg, 0.013 mmol) was dissolved in methanol (2 mL), and a solution of hydrogen chloride in methanol (10 mL) was added. The mixture was reacted overnight at room temperature, concentrated and purified to yield a product of 10 mg. $^1$HNMR (400 MHz, d$_6$-DMSO) δ 11.02 (s, 1H), 10.88 (brs, 1H), 10.67 (brs, 1H), 9.01 (s, 1H), 8.15 (d, J=2.4 Hz, 1H), 7.92-7.89 (m, 1H), 7.81-7.78 (m, 1H), 7.50 (d, J=9.6 Hz, 1H), 5.88-5.84 (m, 1H), 5.35-5.32 (m, 1H), 5.14-5.09 (m, 1H), 4.55-4.34 (m, 2H), 3.82-3.59 (m, 15H), 3.28-2.88 (m, 15H), 2.45 (s, 3H), 2.35 (s, 3H), 2.29-2.17 (m, 5H), 2.04-1.92 (m, 5H), 1.86-1.76 (m, 2H). [M+H]$^+$=935.5.

7) The synthesis route of Compound 36 was illustrated as below:

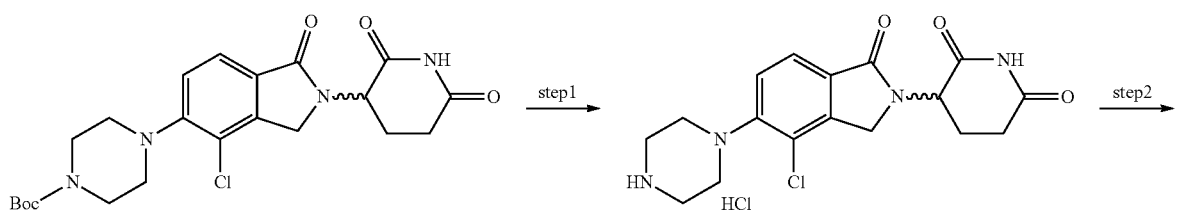

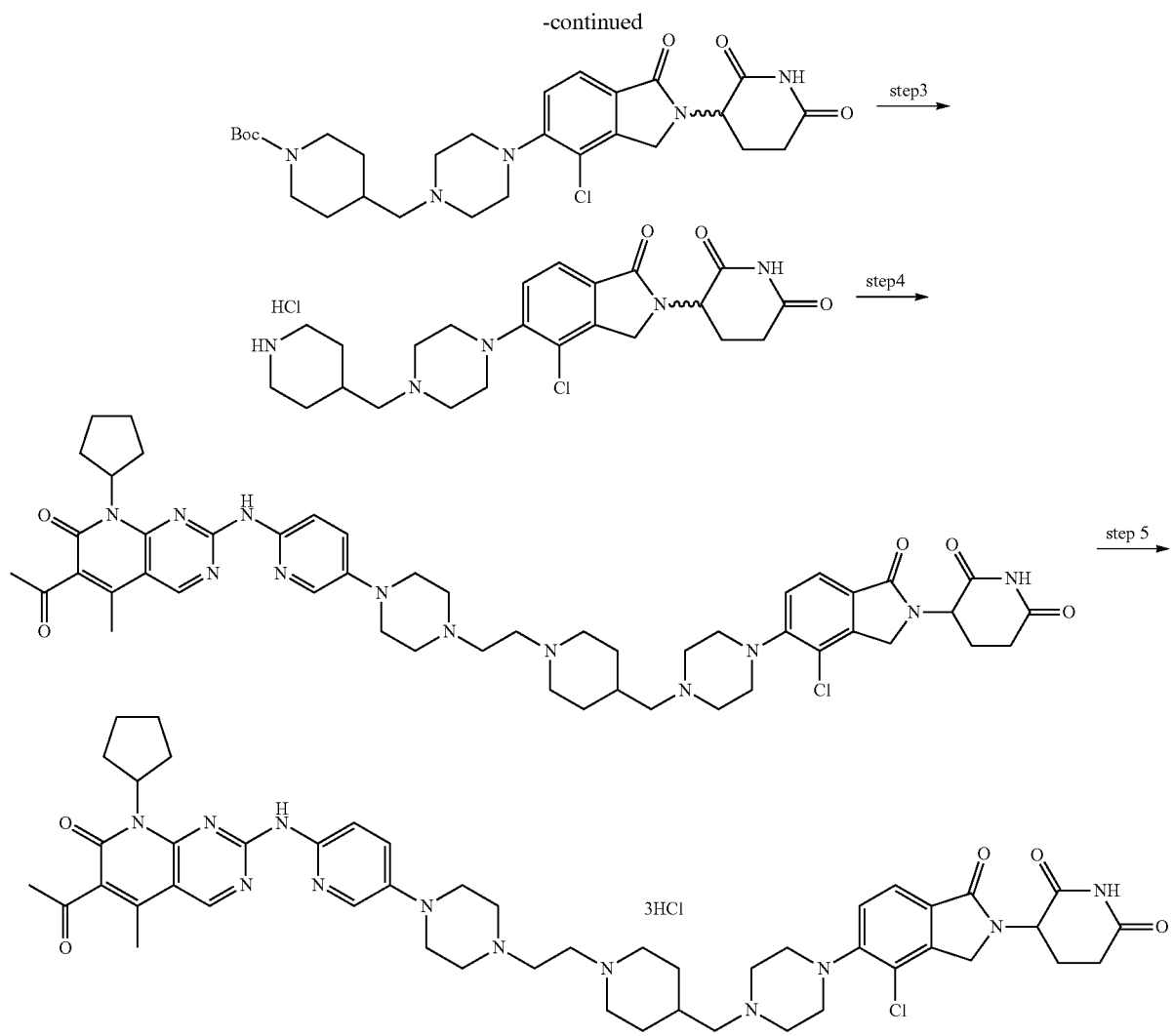

Step 1: Preparation of 3-(4-chloro-1-oxo-5-(piperazin-1-yl)isoindolin-2-yl)piperidine-2,6-dione hydrochloride Tert-butyl 4-(4-chloro-2-(2,6-dioxopiperidin-3-yl)-1-oxoisoindolin-5-yl)piperazine-1-carboxylate (500 mg, 1.08 mmol) was dissolved in ethyl acetate (10 mL), and a solution of hydrogen chloride in ethyl acetate (50 mL) was added. The mixture was reacted overnight at room temperature and concentrated to yield a crude product of 500 mg. [M+H]$^+$= 363.2.

Step 2: Preparation of tert-butyl 4-((4-(4-chloro-2-(2,6-dioxopiperidin-3-yl)-1-oxoisoindolin-5-yl)piperazin-1-yl)methyl)piperidine-1-carboxylate 3-(4-Chloro-1-oxo-5-(piperazin-1-yl)isoindolin-2-yl)piperidine-2,6-dione hydrochloride (500 mg) was dissolved in 1,2-dichloroethane (50 mL), and tert-butyl 4-formylpiperidine-1-carboxylate (213 mg, 1 mmol) and sodium triacetoxyborohydride (1.06 g, 5 mmol) were added. The mixture was reacted overnight at room temperature, concentrated and then purified by column chromatography to yield a product of 400 mg. [M+H]$^+$=560.3.

Step 3: Preparation of 3-(4-chloro-1-oxo-5-(4-(piperidin-4-ylmethyl)piperazin-1-yl)isoindolin-2-yl)piperidine-2,6-dione hydrochloride Tert-butyl 4-((4-(4-chloro-2-(2,6-dioxopiperidin-3-yl)-1-oxoisoindolin-5-yl)piperazin-1-yl)methyl)piperidine-1-carboxylate (200 mg, 0.36 mmol) was dissolved in methanol (5 mL), and a solution of hydrogen chloride in methanol (20 mL) was added. The mixture was reacted overnight at room temperature and concentrated to yield a crude product of 200 mg. [M+H]$^+$=460.3.

Step 4: Preparation of 3-(5-(4-((1-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperidin-4-yl)methyl)piperazin-1-yl)-4-chloro-1-oxoisoindolin-2-yl)piperidine-2,6-dione 3-(4-Chloro-1-oxo-5-(4-(piperidin-4-ylmethyl)piperazin-1-yl)isoindolin-2-yl)piperidine-2,6-dione hydrochloride (200 mg) was dissolved in acetonitrile (20 mL). 6-Acetyl-2-((5-(4-(2-bromoethyl)piperazin-1-yl)pyridin-2-yl)amino)-8-cyclopentyl-5-methylpyrido[2,3-d]pyrimidin-7(8H)-one (277 mg, 0.5 mmol), diisopropylethylamine (194 mg, 1.5 mmol) and a catalytic amount of potassium iodide were added. The mixture was reacted overnight at 80° C., concentrated and then purified by column chromatography to yield a product of 25 mg. [M+H]$^+$=933.5.

Step 5: Preparation of 3-(5-(4-((1-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperidin-4-yl)methyl)piperazin-1-yl)-4-chloro-1-oxoisoindolin-2-yl)piperidine-2,6-dione trihydrochloride 3-(5-(4-((1-(2-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)ethyl)piperidin-4-yl)methyl)piperazin-1-yl)-4-chloro-1-oxoisoindolin-2-yl)piperidine-2,6-dione (25 mg, 0.027 mmol) was dissolved in methanol (2 mL), and a solution of hydrogen chloride in methanol (5 mL) was added. The mixture was reacted overnight at room temperature, concentrated and then purified by a preparative TLC plate to yield a product of 12 mg. $^1$HNMR (400 MHz, d$_6$-DMSO) δ 11.16 (brs, 1H), 11.01 (s, 1H), 10.94 (brs, 1H), 9.03 (brs, 1H), 8.15 (s, 1H), 7.90 (s, 2H), 7.73 (d, J=8 Hz, 1H), 7.36 (d, J=8 Hz, 1H), 5.88-5.84 (m, 1H), 5.15-5.10 (m, 1H), 4.48-4.28 (m, 2H), 3.98-3.67 (m, 17H), 3.28-2.88 (m, 13H), 2.45 (s, 3H), 2.36 (s, 3H), 2.27-2.19 (m, 4H), 2.04-1.92 (m, 4H), 1.86-1.77 (m, 2H), 1.70-1.61 (m, 2H). [M+H]$^+$= 933.5.

8) The synthesis route of Compound 44 was illustrated as below:

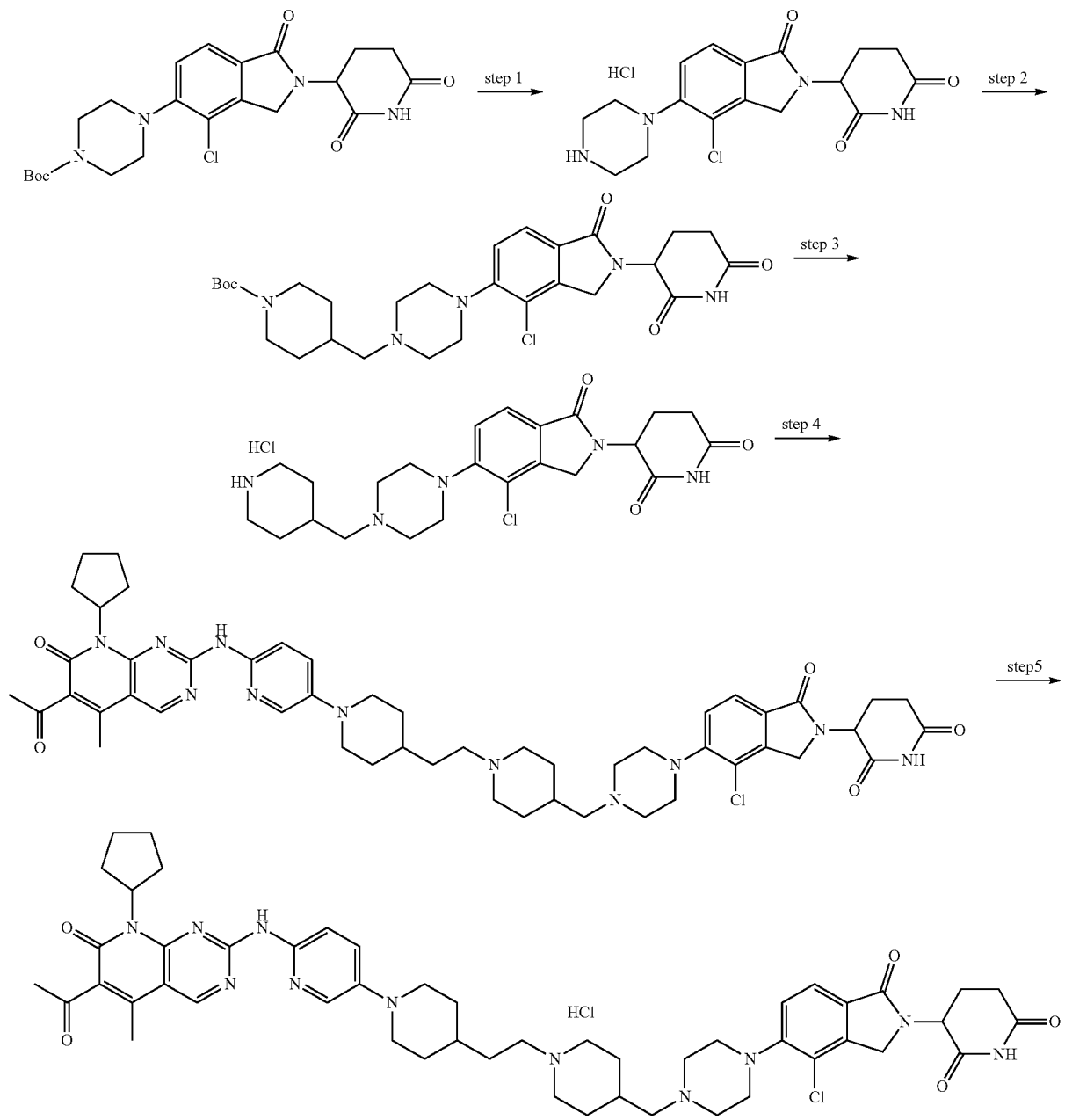

Step 1: Preparation of 3-(4-chloro-1-oxo-5-(piperazin-1-yl)isoindolin-2-yl)piperidine-2,6-dione hydrochloride Tert-butyl 4-(4-chloro-2-(2,6-dioxopiperidin-3-yl)-1-oxoisoindolin-5-yl)piperazine-1-carboxylate (200 mg, 0.43 mmol) was dissolved in methanol (10 mL), and a solution of hydrogen chloride in methanol (50 mL) was added. The mixture was reacted overnight at room temperature and concentrated to yield a crude product of 200 mg. [M+H]$^+$=363.1.

Step 2: Preparation of tert-butyl 4-((4-(4-chloro-2-(2,6-dioxopiperidin-3-yl)-1-oxoisoindolin-5-yl)piperazin-1-yl)methyl)piperidine-1-carboxylate 3-(4-Chloro-1-oxo-5-(piperazin-1-yl)isoindolin-2-yl)piperidine-2,6-dione hydrochloride (200 mg) was dissolved in 1,2-dichloroethane (50 mL), and tert-butyl 4-formylpiperidine-1-carboxylate (107 mg, 0.5 mmol) and sodium triacetoxyborohydride (530 mg, 2.5 mmol) were added. The mixture was reacted overnight at room temperature, concentrated and then purified by column chromatography to yield a product of 150 mg. [M+H]$^+$=560.3.

Step 3: Preparation of 3-(4-chloro-1-oxo-5-(4-(piperidin-4-ylmethyl)piperazin-1-yl)isoindolin-2-yl)piperidine-2,6-dione hydrochloride Tert-butyl 4-((4-(4-chloro-2-(2,6-dioxopiperidin-3-yl)-1-oxoisoindolin-5-yl)piperazin-1-yl)methyl)piperidine-1-carboxylate (110 mg, 0.2 mmol) was dissolved in methanol (5 mL), and a solution of hydrogen chloride in methanol (20 mL) was added. The mixture was reacted overnight at room temperature and concentrated to yield a crude product of 100 mg. [M+H]$^+$=460.3.

Step 4: Preparation of 3-(5-(4-((1-(2-(1-(6-((6-acetyl-8-cyclopentyl-5-methyl-7-oxo-7,8-dihydropyrido[2,3-d]pyrimidin-2-yl)amino)pyridin-3-yl)piperidin-4-yl)ethyl)piperidin-4-yl)methyl)piperazin-1-yl)-4-chloro-1-oxoisoindolin-2-yl)piperidine-2,6-dione 3-(4-Chloro-1-oxo-5-(4-(piperidin-4-ylmethyl)piperazin-1-yl)isoindolin-2-yl)piperidine-2,6-dione hydrochloride (100 mg) was dissolved in acetonitrile (50 mL). 6-Acetyl-2-((5-(4-(2-chloroethyl)piperidin-1-yl)pyridin-2-yl)amino)-8-cyclopentyl-5-methylpyrido[2,3-d]pyrimidin-7(8H)-one (166 mg, 0.3 mmol), diisopropylethylamine (129 mg, 1 mmol) and a catalytic amount of potassium iodide were added. The mixture was reacted overnight at 80° C., concentrated and then purified by column chromatography to yield a product of 10 mg. [M+H]$^+$=932.5.

Step 5: Preparation of 3-(5-(4-((1-(2-(1-(6-((6-acetyl-8-cyclopentyl-5-methyl-7-oxo-7,8-dihydropyrido[2,3-d]pyrimidin-2-yl)amino)pyridin-3-yl)piperidin-4-yl)ethyl)piperidin-4-yl)methyl)piperazin-1-yl)-4-chloro-1-oxoisoindolin-2-yl)piperidine-2,6-dione dihydrochloride 3-(5-(4-((1-(2-(1-(6-((6-Acetyl-8-cyclopentyl-5-methyl-7-oxo-7,8-dihydropyrido[2,3-d]pyrimidin-2-yl)amino)pyridin-3-yl)piperidin-4-yl)ethyl)piperidin-4-yl)methyl)piperazin-1-yl)-4-chloro-1-oxoisoindolin-2-yl)piperidine-2,6-dione (8 mg, 0.0086 mmol) was dissolved in methanol (2 mL), and a solution of hydrogen chloride in methanol (5 mL) was added. The mixture was reacted overnight at room temperature, concentrated and then purified by a preparative TLC plate to yield a product of 7.1 mg. $^1$HNMR (400 MHz, CDCl$_3$) δ 8.84 (s, 1H), 8.28 (brs, 1H), 8.13-8.05 (m, 2H), 7.76 (d, J=8 Hz, 1H), 7.36-7.34 (m, 1H), 7.16 (d, J=8 Hz, 1H), 5.94-5.85 (m, 1H), 5.20-5.16 (m, 1H), 4.42-4.30 (m, 2H), 3.88 (s, 2H), 3.64-3.55 (m, 4H), 3.17-2.89 (m, 7H), 2.77-2.65 (m, 5H), 2.57 (s, 3H), 2.39-2.23 (m, 10H), 2.07-2.04 (m, 5H), 1.90-1.65 (m, 14H). [M+H]$^+$=932.5.

9) The synthesis route of Compound 45 was illustrated as below:

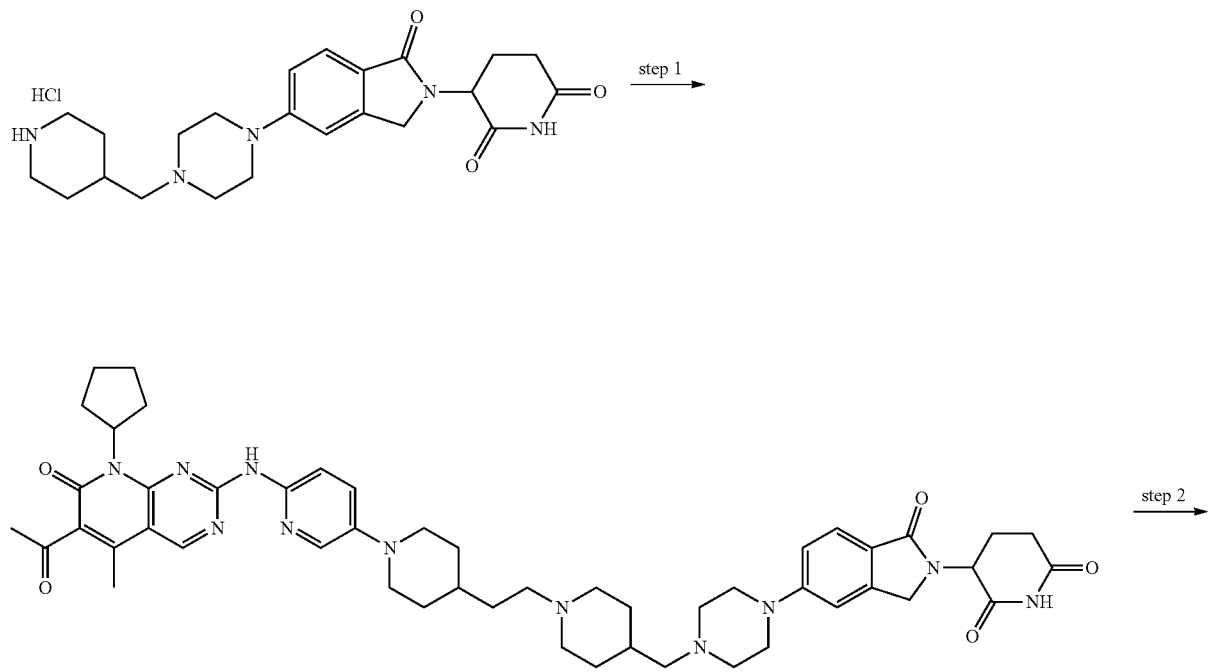

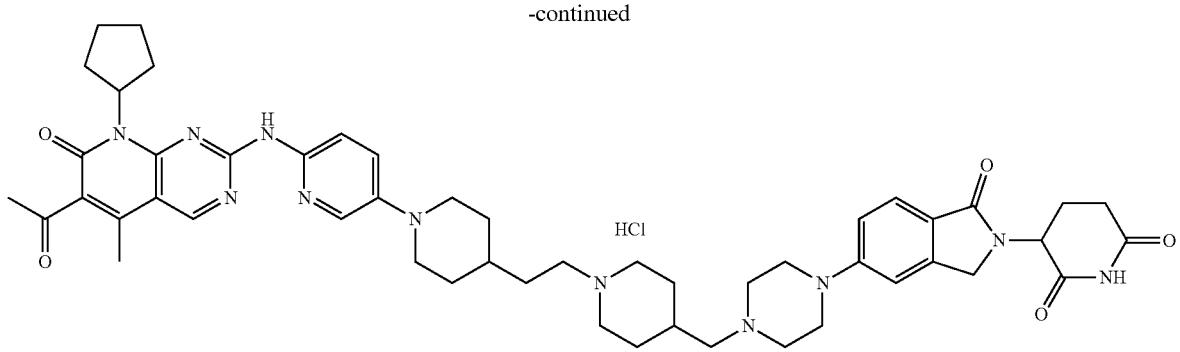

Step 1: Preparation of 3-(5-(4-((1-(2-(1-(6-((6-acetyl-8-cyclopentyl-5-methyl-7-oxo-7,8-dihydropyrido[2,3-d]pyrimidin-2-yl)amino)pyridin-3-yl)piperidin-4-yl)ethyl)piperidin-4-yl)methyl)piperazin-1-yl)-1-oxoisoindolin-2-yl)piperidine-2,6-dione 3-(1-Oxo-5-(4-(piperidin-4-ylmethyl)piperazin-1-yl)isoindolin-2-yl)piperidine-2,6-dione hydrochloride (100 mg, 0.2 mmol) was dissolved in acetonitrile (20 mL). 6-Acetyl-2-((5-(4-(2-chloroethyl)piperidin-1-yl)pyridin-2-yl)amino)-8-cyclopentyl-5-methylpyrido[2,3-d]pyrimidin-7(8H)-one (166 mg, 0.3 mmol), diisopropylethylamine (129 mg, 1 mmol) and a catalytic amount of potassium iodide were added. The mixture was reacted overnight at 80° C., concentrated and then purified by column chromatography to yield a product of 3.5 mg. [M+H]$^+$=898.5.

Step 2: Preparation of 3-(5-(4-((1-(2-(1-(6-((6-acetyl-8-cyclopentyl-5-methyl-7-oxo-7,8-dihydropyrido[2,3-d]pyrimidin-2-yl)amino)pyridin-3-yl)piperidin-4-yl)ethyl)piperidin-4-yl)methyl)piperazin-1-yl)-1-oxoisoindolin-2-yl)piperidine-2,6-dione dihydrochloride 3-(5-(4-((1-(2-(1-(6-((6-Acetyl-8-cyclopentyl-5-methyl-7-oxo-7,8-dihydropyrido[2,3-d]pyrimidin-2-yl)amino)pyridin-3-yl)piperidin-4-yl)ethyl)piperidin-4-yl)methyl)piperazin-1-yl)-1-oxoisoindolin-2-yl)piperidine-2,6-dione (3.5 mg, 0.004 mmol) was dissolved in methanol (2 m), and a solution of hydrogen chloride in meth added. The mixture was reacted overnight at room temperature and concentrated to yield a product of 3.4 mg. $^1$HNMR (400 MHz, CDCl$_3$) 8.80 (s, 1H), 8.13 (brs, 1H), 8.01-8.00 (m, 1H), 7.74 (d, J=8.8 Hz, 1H), 7.38-7.36 (m, 1H), 7.03-6.99 (m, 1H), 6.89 (s, 1H), 5.90-5.86 (m, 1H), 5.21-5.16 (m, 1H), 4.44-4.26 (m, 2H), 3.63 (d, J=12 Hz, 2H), 3.43 (s, 1H), 3.31 (s, 3H), 2.93-2.84 (m, 3H), 2.78-2.72 (m, 2H), 2.58-2.56 (m, 6H), 2.33-2.21 (m, 16H), 2.07-1.69 (m, 15H). [M+H]$^+$=898.5.

W was methylene, m was equal to 2; the ring consisting of Z1 to Z6 was piperazine ring or piperidine ring; and R was absent, halogen or alkoxy.

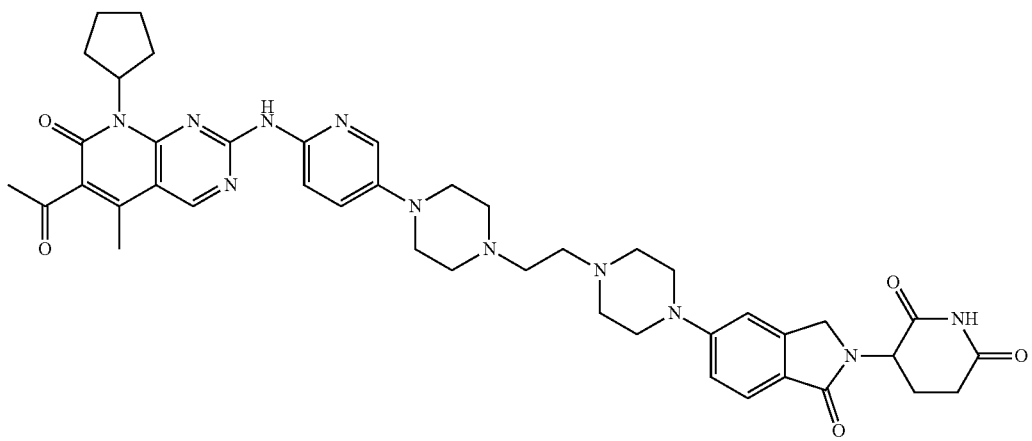

1

-continued
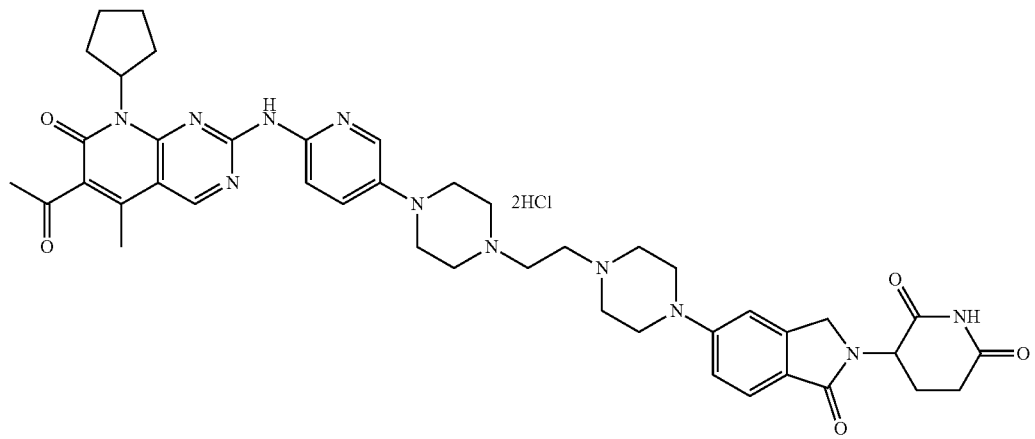
2
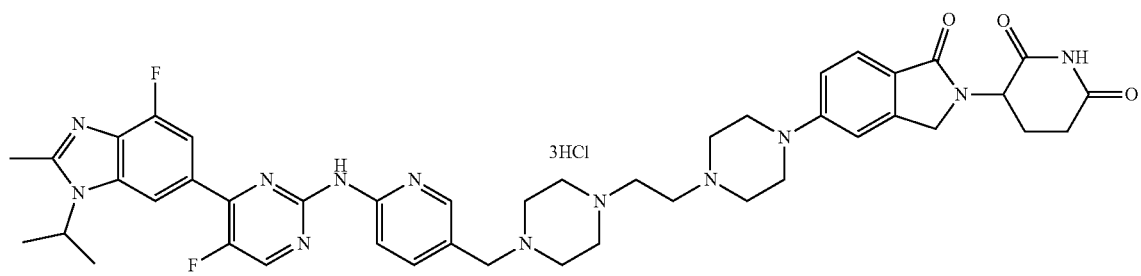
12
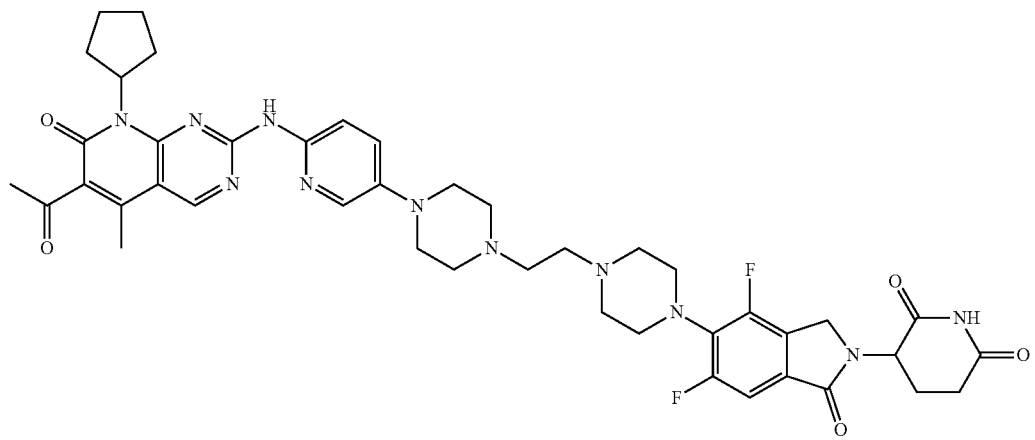
22
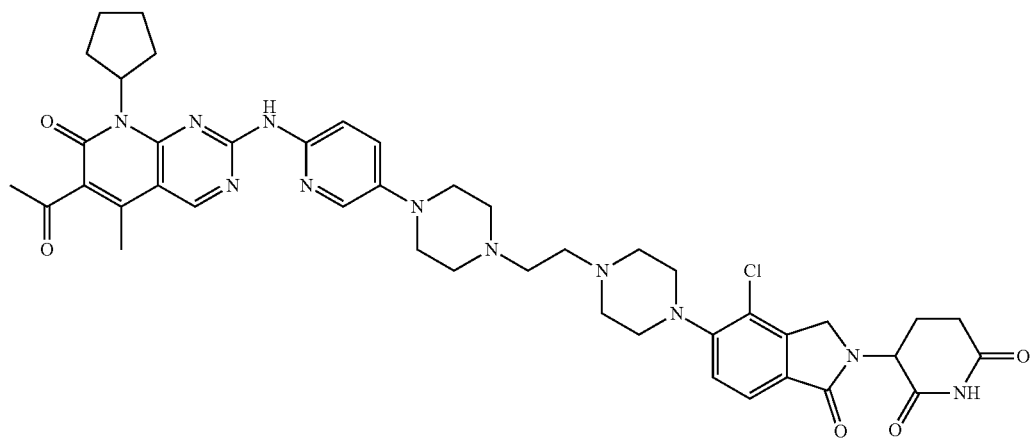
20

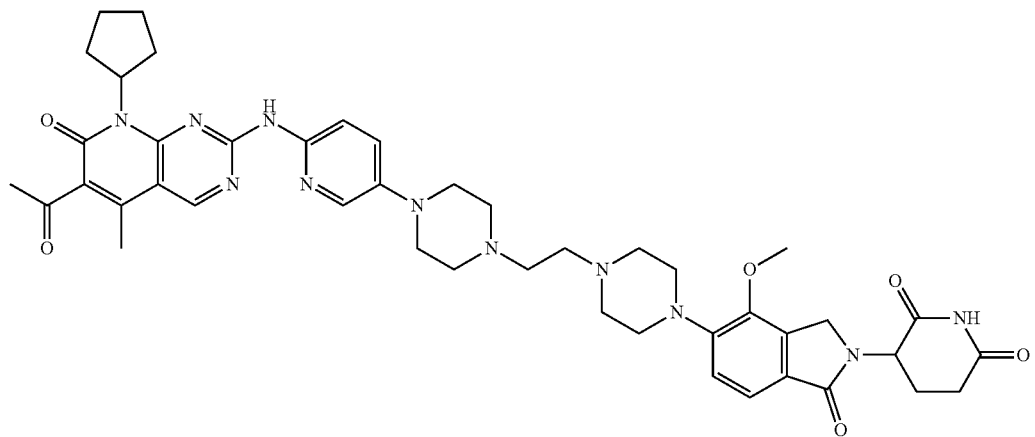 [SMILES: COc1c(N2CCN(CCN3CCN(c4ccc(Nc5ncc6c(C)c(C(C)=O)c(=O)n(C7CCCC7)c6n5)nc4)CC3)CC2)ccc2c1CN(C1CCC(=O)NC1=O)C2=O]
18
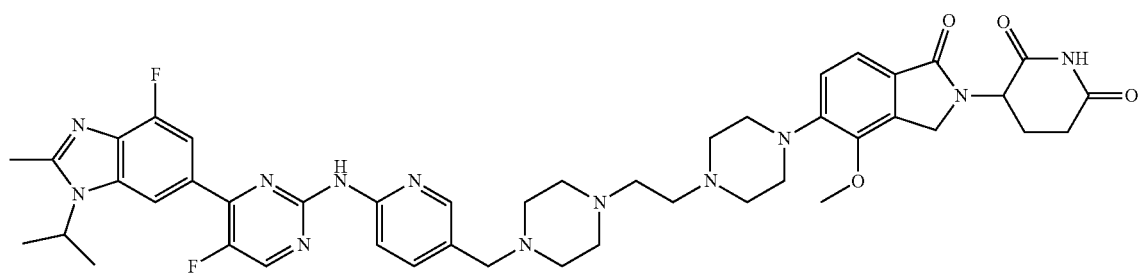 [SMILES: COc1c(N2CCN(CCN3CCN(Cc4ccc(Nc5ncc(F)c(-c6cc(F)c7nc(C)n(C(C)C)c7c6)n5)nc4)CC3)CC2)ccc2c1CN(C1CCC(=O)NC1=O)C2=O]
24
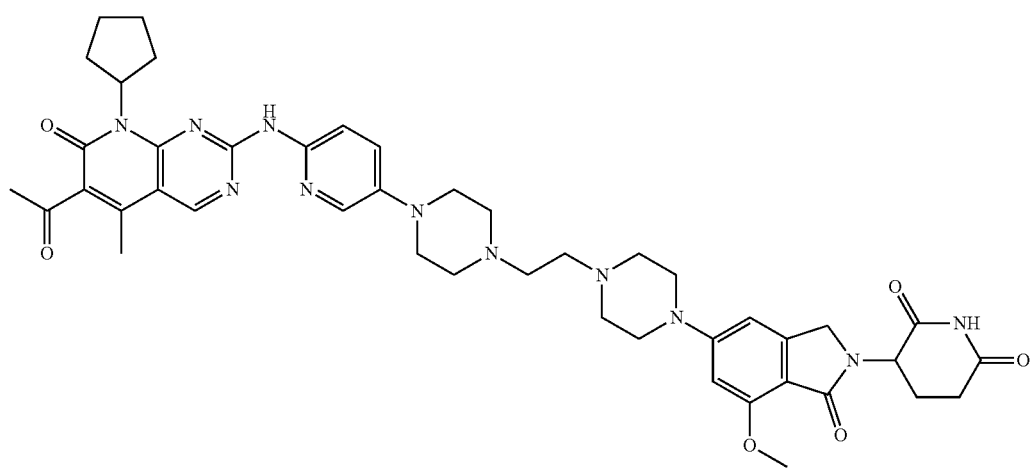
16

17
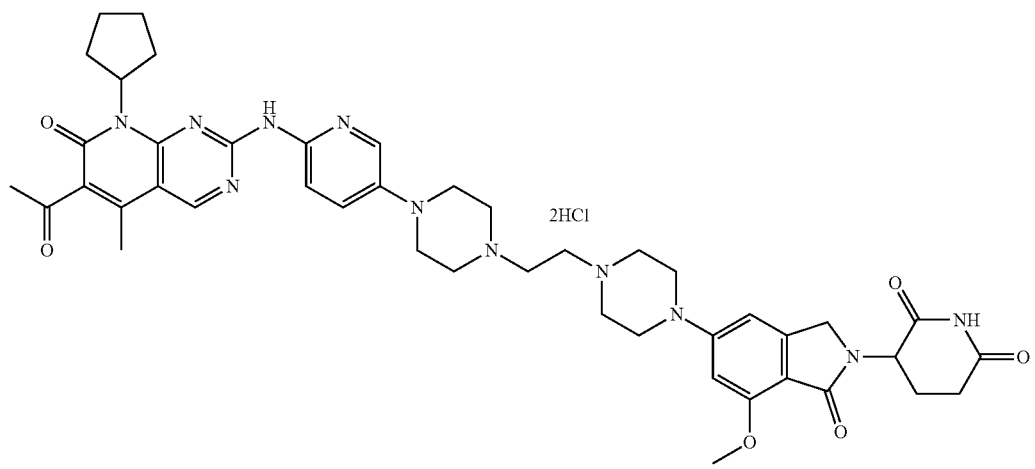
21
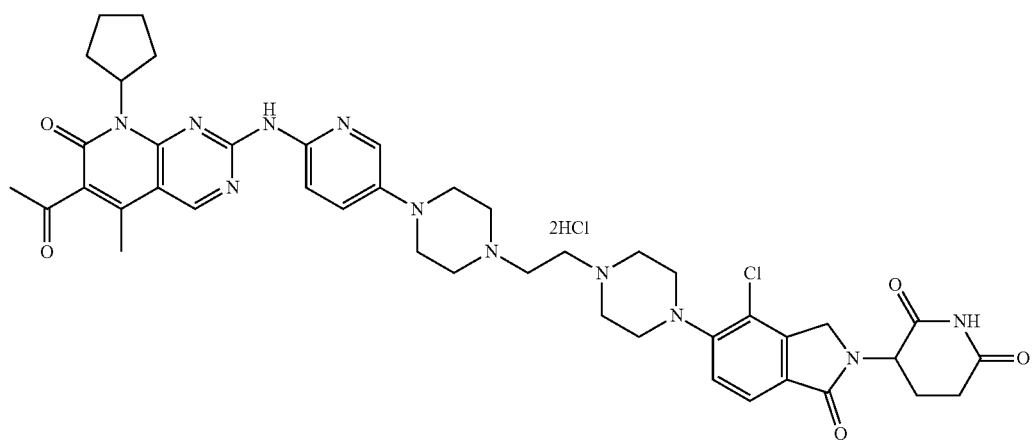
25
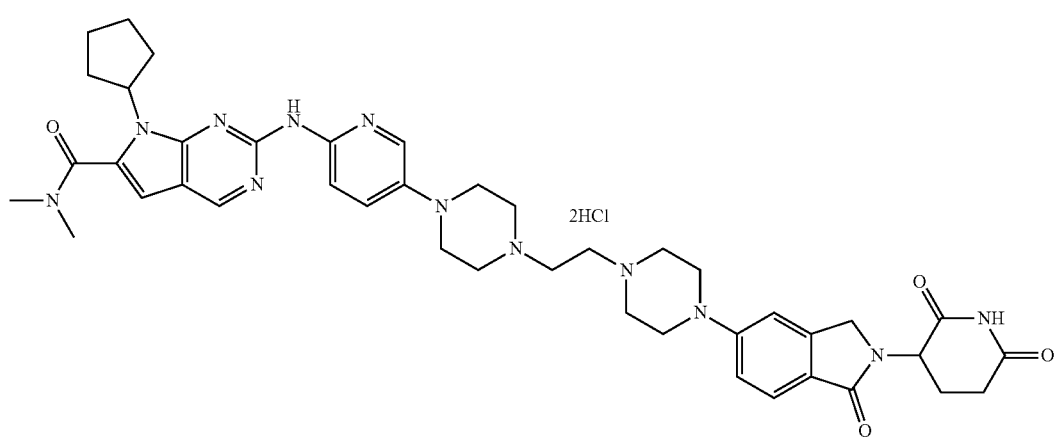

-continued
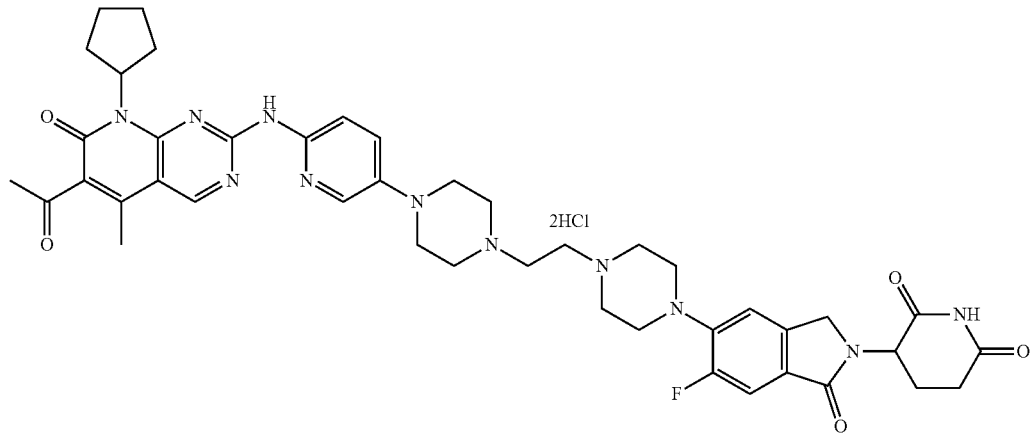 [SMILES: CC(=O)c1c(C)c2cnc(Nc3ccc(N4CCN(CCN5CCN(c6cc7c(cc6F)C(=O)N(C6CCC(=O)NC6=O)C7)CC5)CC4)cn3)nc2n(C2CCCC2)c1=O]
27
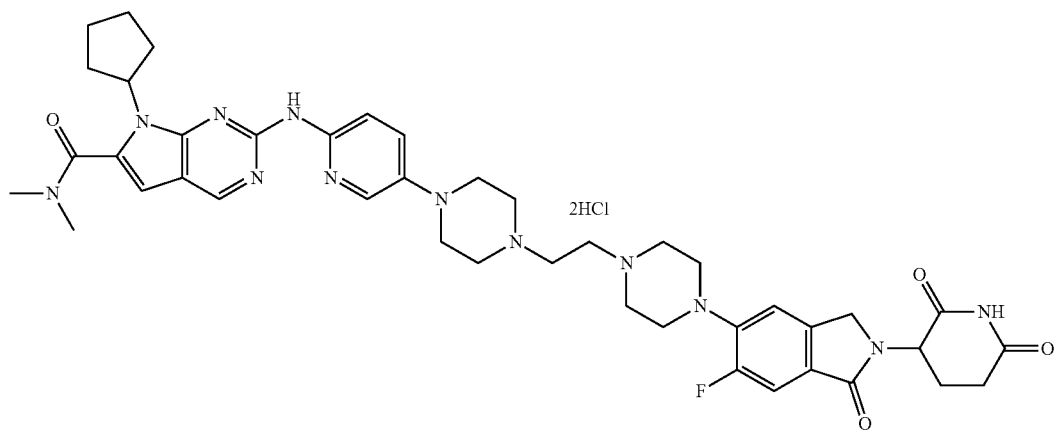
28
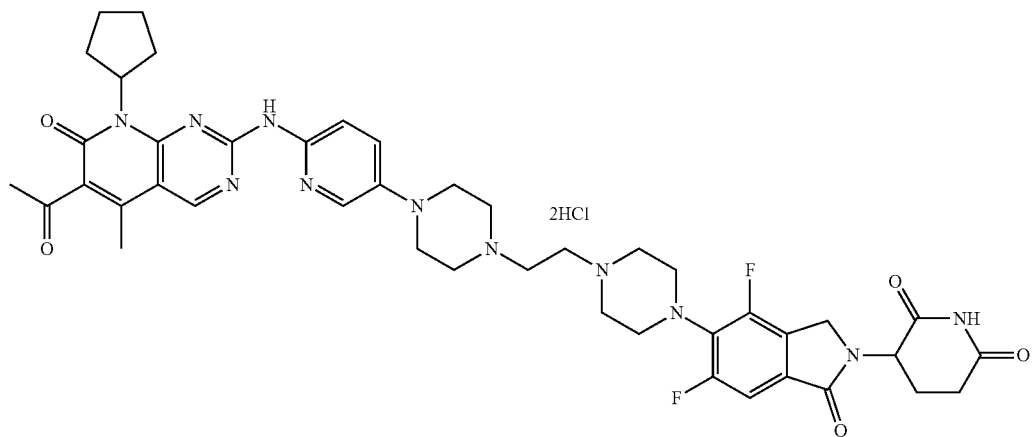
23

32
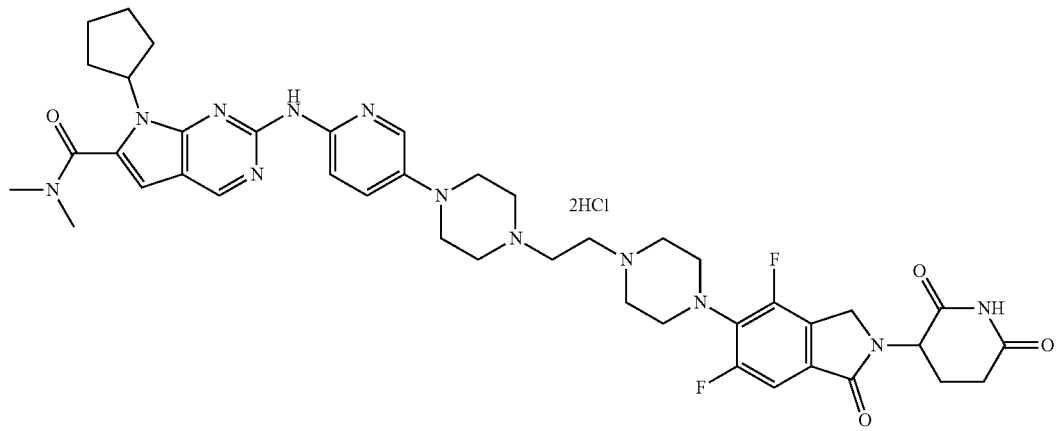
33
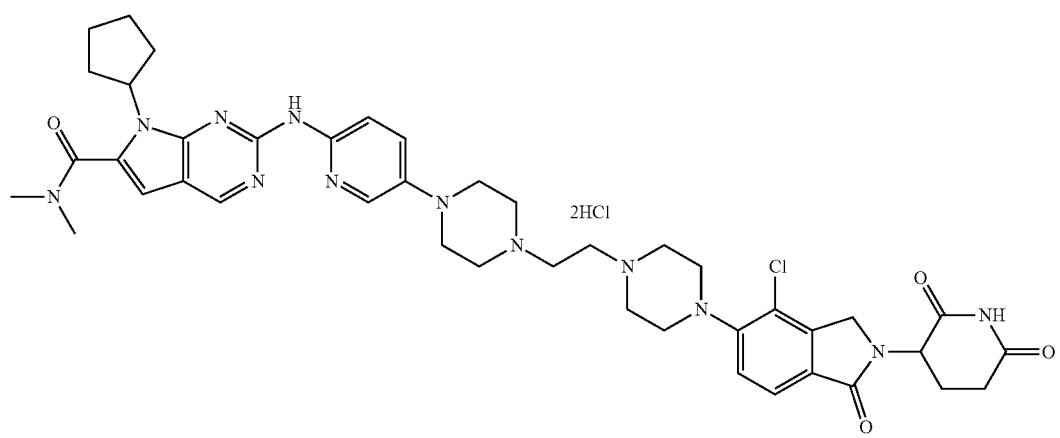
19
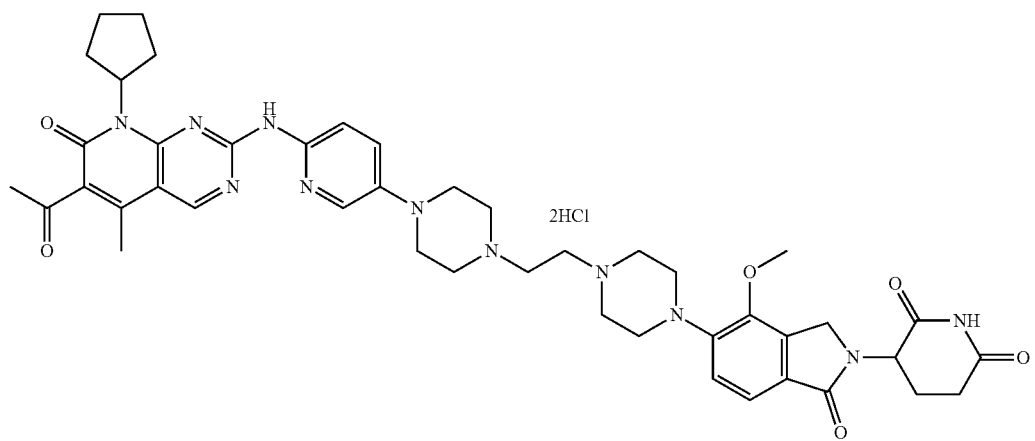

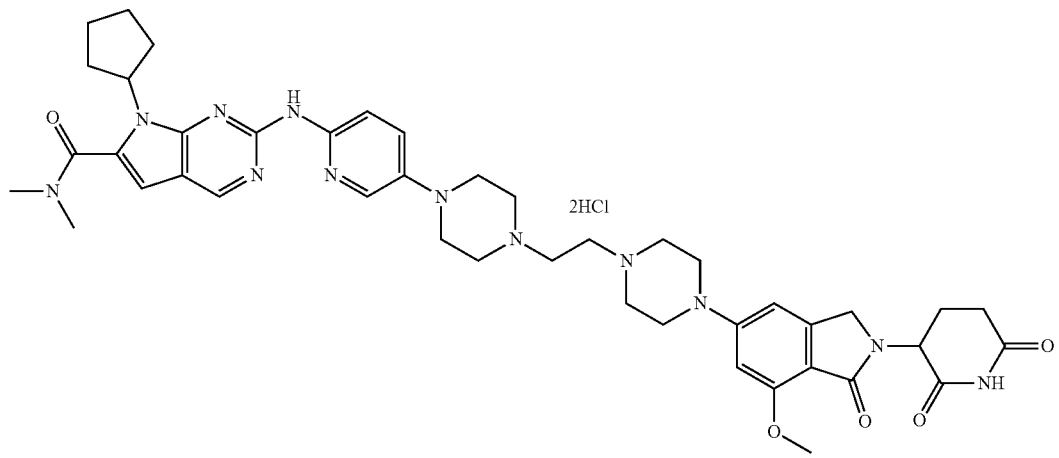
30
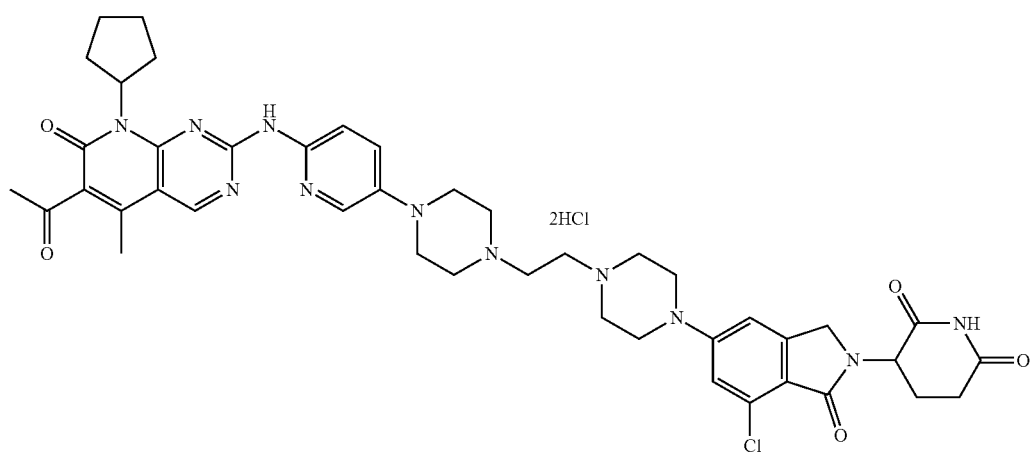 [SMILES: CC(=O)c1c(C)c2cnc(Nc3ccc(N4CCN(CCN5CCN(c6cc(Cl)c7c(c6)CN(C6CCC(=O)NC6=O)C7=O)CC5)CC4)cn3)nc2n(C2CCCC2)c1=O]
31
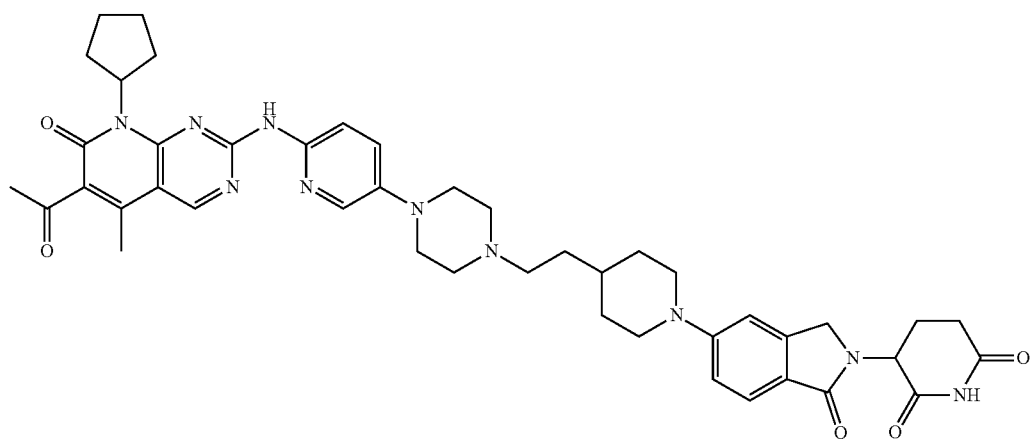
13

-continued
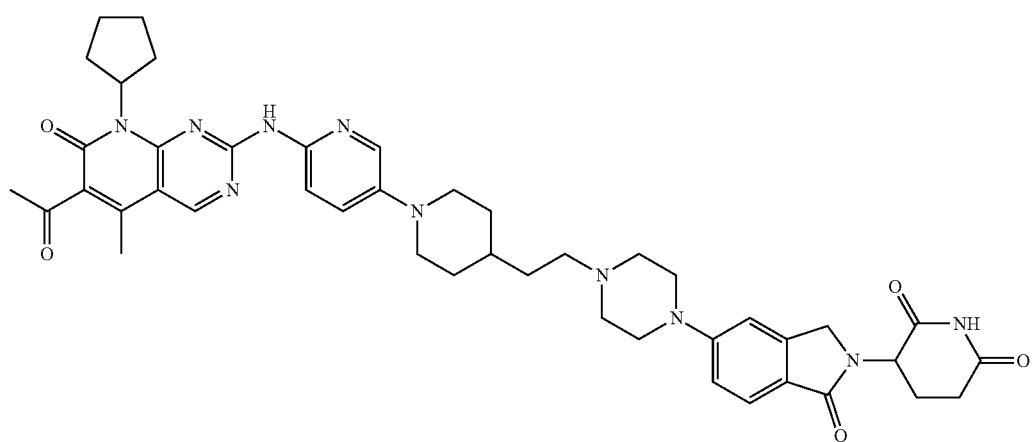
41
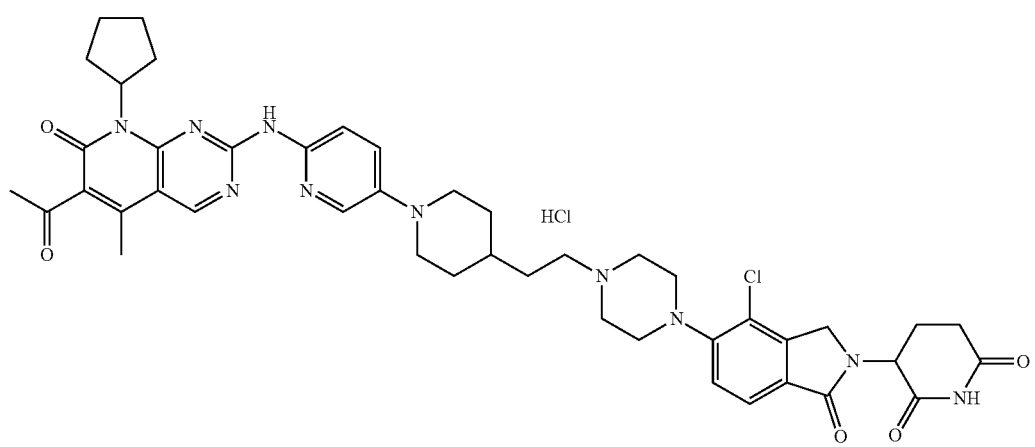
43
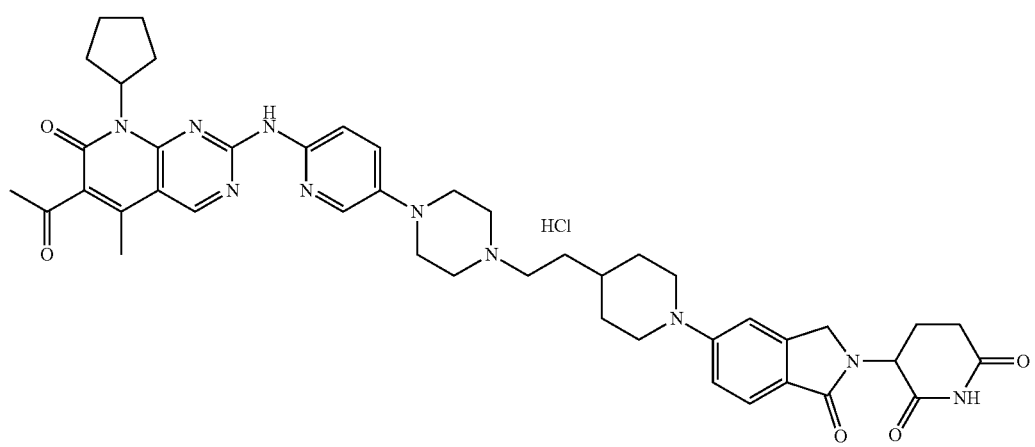
14

10) The synthesis route of Compound 1 was illustrated as below:

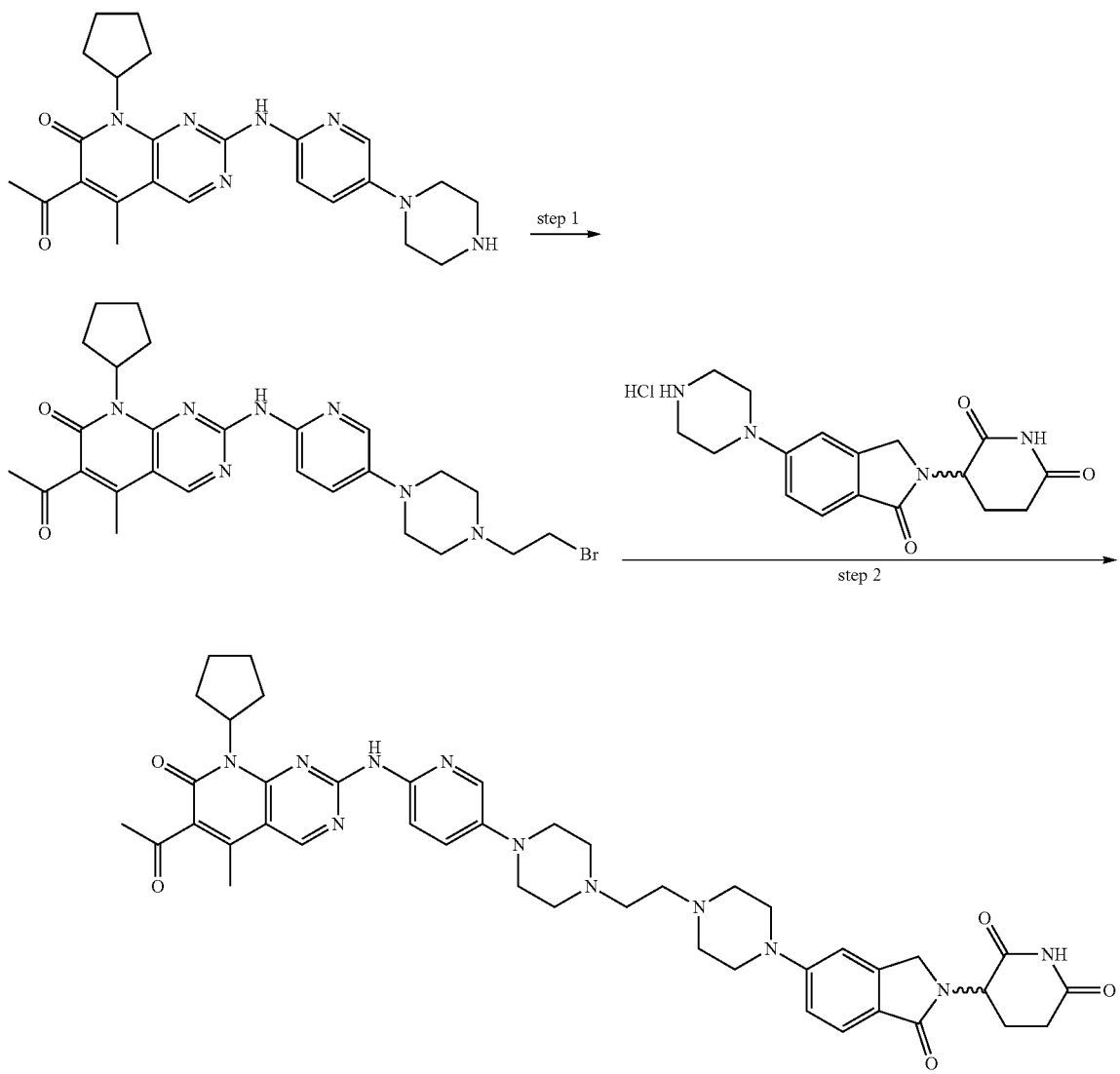

Step 1: Preparation of 6-acetyl-2-((5-(4-(2-bromo-ethyl)piperazin-1-yl)pyridin-2-yl)amino)-8-cyclopentyl-5-methylpyrido[2,3-d]pyrimidin-7(8H)-one Palbociclib (500 mg, 1.12 mmol) was dissolved in dimethylformamide (20 mL). Diisopropylethylamine (724 mg, 5.6 mmol) and 1,2-dibromoethane (2.1 g, 11.2 mmol) were added. After being stirred overnight at 60° C., the reaction solution was diluted with water and then filtered. The filter cake was purified by column chromatography to yield a product of 80 mg. [M+H]$^+$=554.2.

Step 2: Preparation of 3-(5-(4-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperazin-1-yl)-1-oxoisoindolin-2-yl)piperidine-2,6-dione 6-Acetyl-2-((5-(4-(2-bromoethyl)piperazin-1-yl)pyridin-2-yl)amino)-8-cyclopentyl-5-methylpyrido[2,3-d]pyrimi-din-7(8H)-one (10 mg, 0.018 mmol) was dissolved in acetonitrile (5 mL). Diisopropylethylamine (9.3 mg, 0.072 mmol), potassium iodide (1.7 mg, 0.01 mmol) and 3-(1-oxo-5-methylpiperazin-1-yl)isoindolin-2-yl)piperidine-2,6-dione hydrochloride (13 mg, 0.036 mmol) were added. After being stirred overnight at 85° C., the reaction solution was concentrated and then purified by column chromatography to yield a product of 8 mg. 1HNMR (400 MHz, CDCl$_3$) δ 8.83 (m, 1H), 8.21-8.17 (m, 1H), 8.08 (s, 1H), 7.75 (d, J=8 Hz, 1H), 7.37-7.34 (m, 1H), 7.02-7.00 (m, 1H), 6.92 (s, 1H), 5.91-5.87 (m, 1H), 5.20-5.16 (m, 1H), 4.45-4.26 (m, 2H), 3.80-3.44 (m, 10H), 2.95-2.67 (m, 10H), 2.56 (s, 3H), 2.38-2.07 (m, 11H), 1.58-1.46 (m, 4H); [M+H]$^+$=802.4.

11) The synthesis route of Compound 2 was illustrated as below:

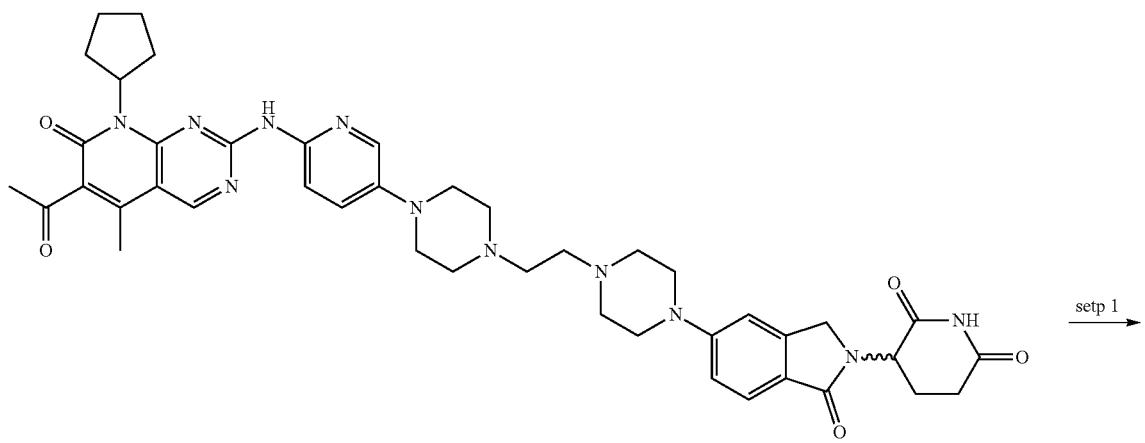

→ setp 1

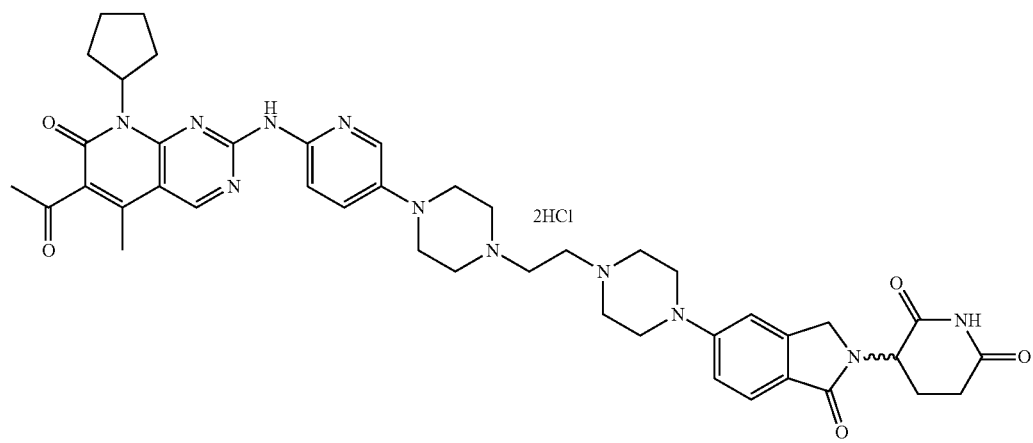

2HCl

Step 1: Preparation of 3-(5-(4-(2-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperazin-1-yl)-1-oxoisoindolin-2-yl)piperidine-2,6-dione dihydrochloride 3-(5-(4-(2-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)ethyl)piperazin-1-yl)-1-oxoisoindolin-2-yl)piperidine-2,6-dione (220 mg, 0.27 mmol) was dissolved in methanol (5 mL), and a solution of hydrogen chloride in methanol (4 M, 20 mL) was added. After being stirred overnight at room temperature, the reaction solution was dried by a rotary evaporator under reduced pressure to yield a product of 220 mg. $^1$HNMR (400 MHz, d$_6$-DMSO) δ 11.28 (brs, 3H), 11.00 (s, 1H), 9.05 (s, 1H), 8.14 (d, J=2 Hz, 1H), 8.06-8.03 (m, 1H), 7.88 (d, J=9.2 Hz, 1H), 7.62 (d, J=8.4 Hz, 1H), 7.23-7.19 (m, 2H), 5.89-5.85 (m, 1H), 5.11-5.06 (m, 1H), 4.40-4.23 (m, 2H), 3.77-3.68 (m, 8H), 3.30-3.17 (m, 8H), 2.46-2.24 (m, 12H), 1.98-1.62 (m, 10H); [M+H]$^+$=802.4.

12) The synthesis route of Compound 12 was illustrated as below:

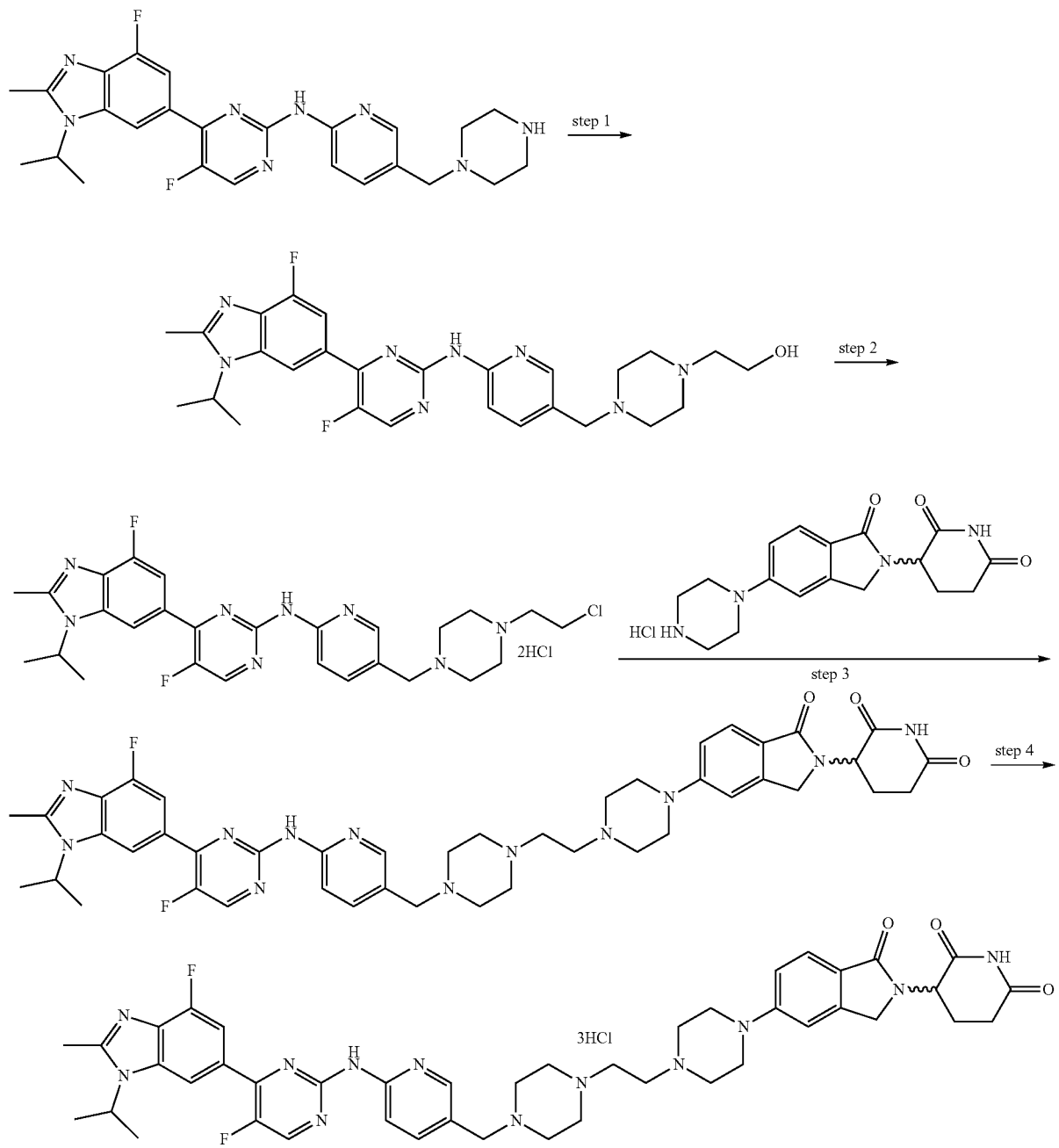

Step 1: Preparation of 2-(4-(((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)ethanol 5-Fluoro-4-(4-fluoro-1-isopropyl-2-methyl-1H-benzo[d]imidazol-6-yl)-N-(5-(piperazin-1-ylmethyl)pyridin-2-yl)pyrimidin-2-amine (1 g, 2.1 mmol) was dissolved in dimethylformamide (10 mL), and diisopropylethylamine (814 mg, 6.3 mmol) and 2-bromoethanol (525 mg, 4.2 mmol) were added. After being heated to 40° C. and stirred overnight, the reaction solution was concentrated and then purified by column chromatography to yield a product of 500 mg. [M+H]$^+$=523.3.

Step 2: Preparation of N-(5-((4-(2-chloroethyl)piperazin-1-yl)methyl)pyridin-2-yl)-5-fluoro-4-(4-fluoro-1-isopropyl-2-methyl-1H-benzo[d]imidazol-6-yl)pyrimidin-2-amine dihydrochloride 2-(4-(((6-((5-Fluoro-4-(4-fluoro-1-isopropyl-2-methyl-1H-benzo[d]imidazol-6-yl)pyrimidin-2-yl)amino)pyridin-3-yl)methyl)piperazin-1-yl)ethanol (200 mg, 0.38 mmol) was dissolved in thionyl chloride (10 mL). The mixture was heated to reflux and reacted for 2 hours, and then the reaction was terminated. The reaction solution was concentrated and then purified by column chromatography to yield a product of 150 mg. [M+H]$^+$=541.2.

Step 3: Preparation of 3-(5-(4-(2-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)ethyl)piperazin-1-yl)-1-oxoisoindolin-2-yl) piperidine-2,6-dione N-(5-((4-(2-chloroethyl)piperazin-1-yl)methyl)pyridin-2-yl)-5-fluoro-4-(4-fluoro-1-isopropyl-2-methyl-1H-benzo[d]imidazol-6-yl)pyrimidin-2-amine dihydrochloride (50 mg, 0.08 mmol) was dissolved in dimethylformamide (5 mL). Sodium bicarbonate (67 mg, 0.8 mmol), potassium iodide (13 mg, 0.08 mmol) and 3-(1-oxo-5-(piperazin-1-yl)isoindolin-2-yl)piperidine-2,6-dione hydrochloride (29 mg, 0.08 mmol) were added. After being heated to 50° C. and reacted overnight, the reaction solution was concentrated and then purified by column chromatography to yield a product of 10 mg. [M+H]⁺=833.4.

Step 4: Preparation of 3-(5-(4-(2-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)ethyl)piperazin-1-yl)-1-oxoisoindolin-2-yl) piperidine-2,6-dione trihydrochloride 3-(5-(4-(2-(4-((6-((5-Fluoro-4-(4-fluoro-1-isopropyl-2-methyl-1H-benzo[d]imidazol-6-yl)pyrimidin-2-yl)amino)pyridin-3-yl)methyl)piperazin-1-yl)ethyl)piperazin-1-yl)-1-oxoisoindolin-2-yl)piperidine-2,6-dione (7 mg, 0.0084 mmol) was dissolved in methanol (1 mL), and a solution of hydrogen chloride in methanol (4 M, 5 mL) was added. After being stirred overnight at room temperature, the reaction solution was dried by a rotary evaporator under reduced pressure to yield a product of 7 mg. ¹HNMR (400 MHz, d₆-DMSO) δ 11.92 (brs, 1H), 10.97 (s, 1H), 8.93 (d, J=3.2 Hz, 1H), 8.69 (s, 1H), 8.5-8.47 (m, 2H), 8.14 (d, J=8.8 Hz, 1H), 7.97 (d, J=11.2 Hz, 1H), 7.60-7.55 (m, 1H), 7.20-7.16 (m, 2H), 5.09-5.00 (m, 2H), 4.56 (s, 2H), 4.39-4.23 (m, 2H), 3.65-3.42 (m, 20H), 2.95-2.89 (m, 4H), 2.62-2.58 (m, 1H), 2.45-2.34 (m, 1H), 1.99-1.98 (m, 1H), 1.71 (d, J=7.2 Hz, 6H); [M+H]⁺=833.4.

13) The synthesis route of Compound 22 was illustrated as below:

Step 1: Preparation of 3-(4,6-difluoro-1-oxo-5-(piperazin-1-yl)isoindolin-2-yl)piperidine-2,6-dione hydrochloride Tert-butyl 4-(2-(2,6-dioxopiperidin-3-yl)-4,6-difluoro-1-oxoisoindolin-5-yl)piperazine-1-carboxylate (13 mg, 0.028 mmol) was dissolved in methanol (2 mL), and a solution of hydrogen chloride in methanol (10 mL) was added. The mixture was reacted overnight at room temperature and concentrated to yield a crude product of 13 mg, which was directly used in the next step. [M+H]⁺=365.2.

Step 2: Preparation of 3-(5-(4-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperazin-1-yl)-4,6-difluoro-1-oxoisoindolin-2-yl) piperidine-2,6-dione 3-(4,6-Difluoro-1-oxo-5-(piperazin-1-yl)isoindolin-2-yl)piperidine-2,6-dione hydrochloride (13 mg) was dissolved in acetonitrile (10 mL). 6-Acetyl-2-((5-(4-(2-bromoethyl)piperazin-1-yl)pyridin-2-yl)amino)-8-cyclopentyl-5-methylpyrido[2,3-d]pyrimidin-7(8H)-one (22 mg, 0.04 mmol), diisopropylethylamine (52 mg, 0.4 mmol) and a catalytic amount of potassium iodide were added. The mixture was heated to 80° C. and reacted overnight, concentrated and then purified by a preparative TLC plate to yield a product of 7 mg. ¹HNMR (400 MHz, CDCl₃) δ 8.84 (s, 1H), 8.20 (d, J=8.4 Hz, 1H), 8.10 (s, 1H), 7.40-7.35 (m, 2H), 5.92-5.87 (m, 1H), 5.18-5.13 (m, 1H), 4.49-4.32 (m, 2H), 3.97-3.88 (m, 2H), 3.61-3.52 (m, 7H), 3.44-3.38 (m, 3H), 2.95-2.79 (m, 6H), 2.74-2.64 (m, 5H), 2.56 (s, 3H), 2.39-2.32 (m, 7H), 2.25-2.20 (m, 2H), 2.13-2.00 (m, 3H). [M+H]⁺=838.4.

14) The synthesis route of Compound 20 was illustrated as below:

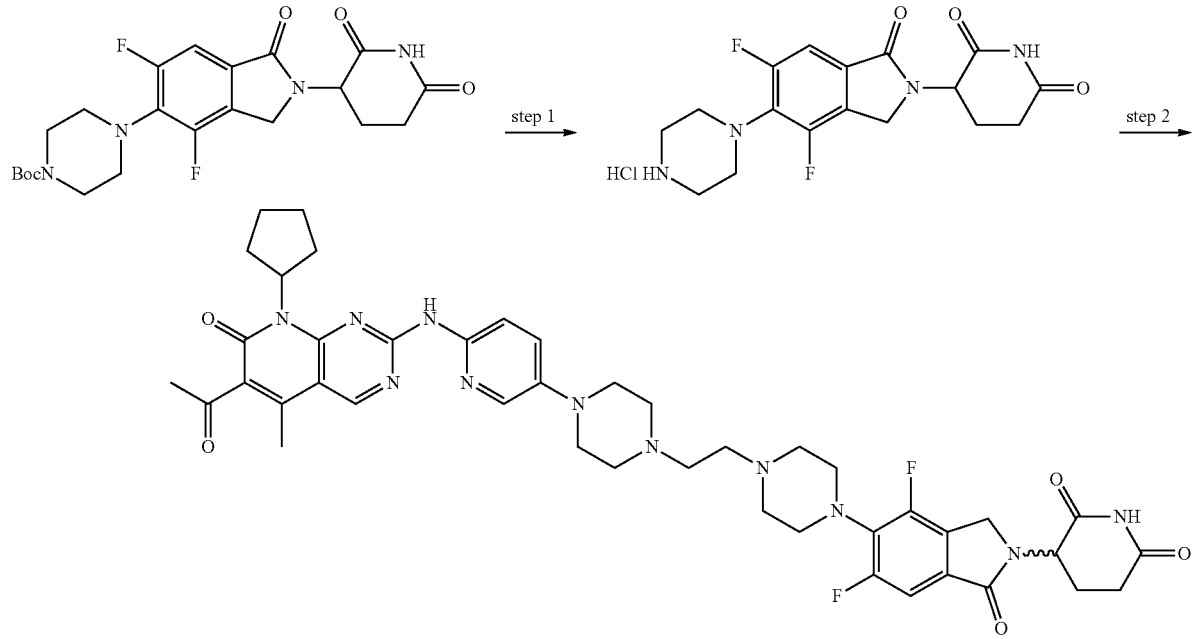

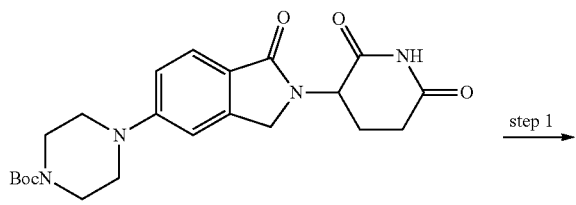 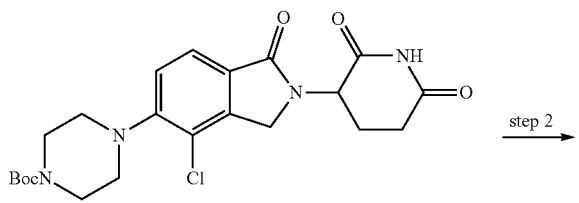

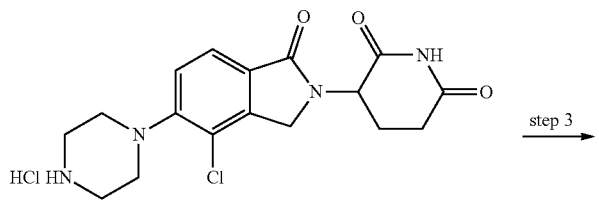

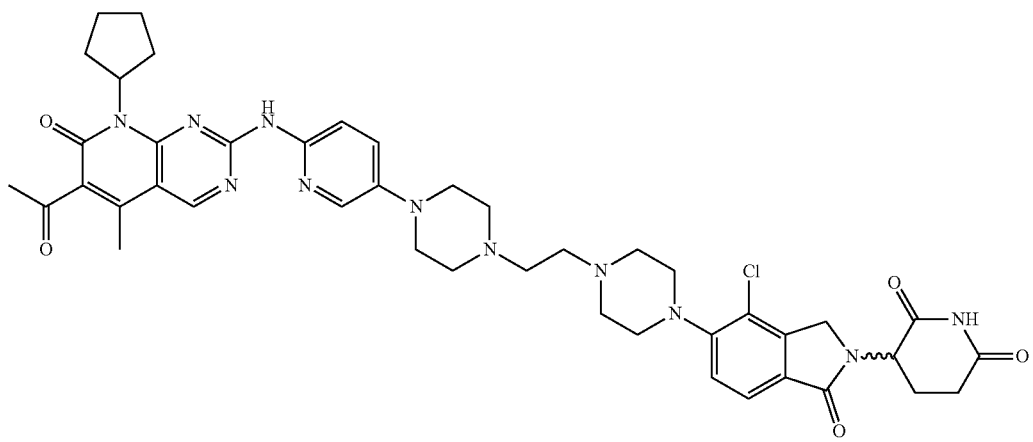

Step 1: Preparation of tert-butyl 4-(4-chloro-2-(2,6-dioxopiperidin-3-yl)-1-oxoisoindolin-5-yl)piperazine-1-carboxylate Tert-butyl 4-(2-(2,6-dioxopiperidin-3-yl)-1-oxoisoindolin-5-yl)piperazine-1-carboxylate (200 mg, 0.47 mmol) was dissolved in a mixed solution (50 mL) of dichloromethane and methanol (dichloromethane:methanol=10:1), and trifluoroacetic acid (97 mg, 1 mmol) and N-chlorosuccinimide (80 mg, 0.6 mmol) were added. The mixture was reacted overnight at room temperature, concentrated and then purified by a preparative TLC plate to yield a product of 130 mg. [M+H]$^+$=463.2.

Step 2: Preparation of 3-(4-chloro-1-oxo-5-(piperazin-1-yl)isoindolin-2-yl)piperidine-2,6-dione hydrochloride Tert-butyl 4-(4-chloro-2-(2,6-dioxopiperidin-3-yl)-1-oxoisoindolin-5-yl)piperazine-1-carboxylate (130 mg, 0.28 mmol) was dissolved in methanol (10 mL), and a solution of hydrogen chloride in methanol (50 mL) was added. The mixture was reacted overnight at room temperature and concentrated to yield a crude product of 130 mg, which was directly used in the next step. [M+H]$^+$=363.2.

Step 3: Preparation of 3-(5-(4-(2-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperazin-1-yl)-4-chloro-1-oxoisoindolin-2-yl)piperidine-2,6-dione 3-(4-Chloro-1-oxo-5-(piperazin-1-yl)isoindolin-2-yl)piperidine-2,6-dione hydrochloride (130 mg) was dissolved in acetonitrile (20 mL). 6-Acetyl-2-((5-(4-(2-bromoethyl)piperazin-1-yl)pyridin-2-yl)amino)-8-cyclopentyl-5-methylpyrido[2,3-d]pyrimidin-7(8H)-one (166 mg, 0.3 mmol), diisopropylethylamine (129 mg, 1 mmol) and a catalytic amount of potassium iodide were added. The mixture was heated to 80° C. and reacted overnight, concentrated and then purified by a preparative TLC plate to yield a product of 26 mg. $^1$HNMR (400 MHz, d$_6$-DMSO) δ 11.01 (s, 1H), 10.14 (s, 1H), 8.97 (s, 1H), 8.09 (d, J=2.4 Hz, 1H), 7.88 (d, J=9.2 Hz, 1H), 7.68 (d, J=8 Hz, 1H), 7.52-7.49 (m, 1H), 7.28 (d, J=8 Hz, 1H), 5.88-5.79 (m, 1H), 5.14-5.10 (m, 1H), 4.46-4.25 (m, 2H), 3.28-3.15 (m, 7H), 2.97-2.58 (m, 11H), 2.48-2.47 (m, 1H), 2.44 (s, 4H), 2.32-2.21 (m, 6H), 2.03-1.99 (m, 1H), 1.90 (brs, 2H), 1.82-1.78 (m, 2H), 1.62-1.59 (m, 2H). [M+H]$^+$=836.4.

15) The synthesis route of Compound 18 was illustrated as below:

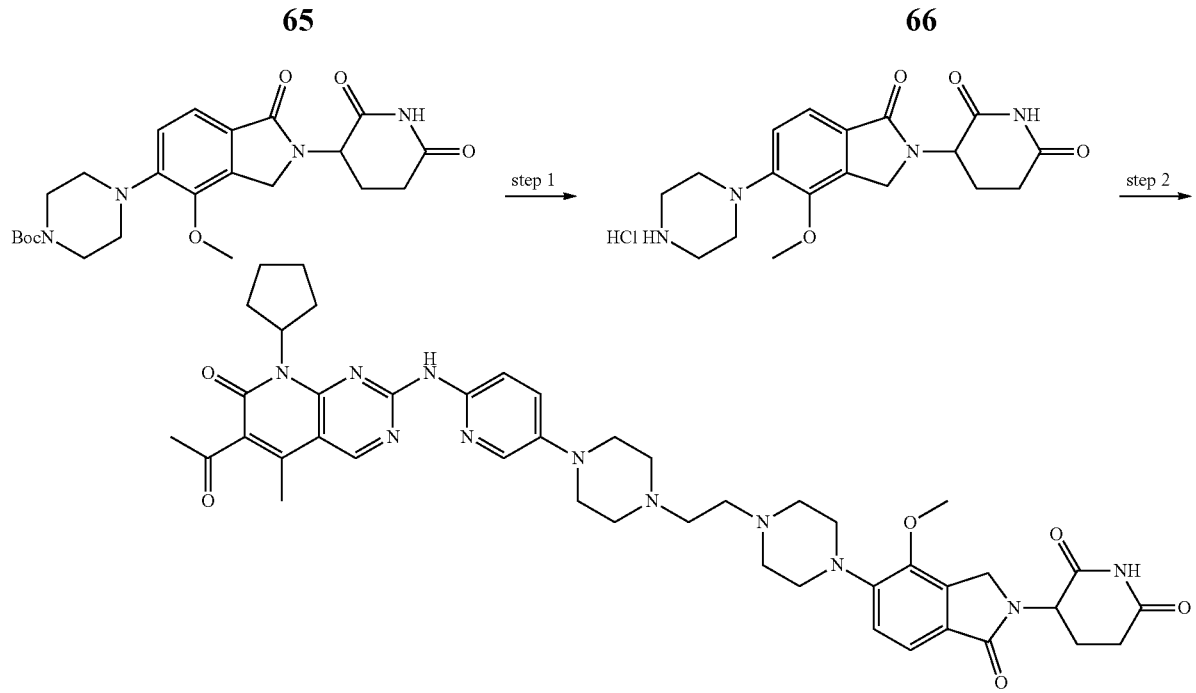

Step 1: Preparation of 3-(4-methoxy-1-oxo-5-(piperazin-1-yl)isoindolin-2-yl)piperidine-2,6-dione hydrochloride Tert-butyl 4-(2-(2,6-dioxopiperidin-3-yl)-4-methoxy-1-oxoisoindolin-5-yl)piperazine-1-carboxylate (150 mg, 0.33 mmol) was dissolved in methanol (10 mL), and a solution of hydrogen chloride in methanol (50 mL) was added. The mixture was reacted overnight at room temperature, concentrated and then purified by a preparative TLC plate to yield a product of 80 mg. [M+H]+=358.2.

Step 2: Preparation of 3-(5-(4-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperazin-1-yl)-4-methoxy-1-oxoisoindolin-2-yl)piperidine-2,6-dione 3-(4-Methoxy-1-oxo-5-(piperazin-1-yl)isoindolin-2-yl)piperidine-2,6-dione hydrochloride (40 mg, 0.1 mmol) was dissolved in acetonitrile (20 mL). 6-Acetyl-2-((5-(4-(2-bromoethyl)piperazin-1-yl)pyridin-2-yl)amino)-8-cyclopentyl-5-methylpyrido[2,3-d]pyrimidin-7(8H)-one (55 mg, 0.1 mmol), diisopropylethylamine (129 mg, 1 mmol) and a catalytic amount of potassium iodide were added. The mixture was heated to 80° C. and reacted overnight, concentrated and then purified by a preparative TLC plate to yield a product of 8.4 mg. $^1$HNMR (400 MHz, CDCl$_3$) δ 8.82 (s, 1H), 8.27-8.23 (brs, 1H), 8.19 (d, J=9.2 Hz, 1H), 8.07-8.03 (m, 2H), 7.59 (d, J=8 Hz, 1H), 7.38-7.35 (m, 1H), 7.06 (d, J=8.4 Hz, 1H), 5.92-5.88 (m, 1H), 5.25-5.21 (m, 1H), 4.49-4.31 (m, 2H), 3.93 (s, 3H), 3.83-3.68 (m, 2H), 3.27-3.25 (m, 7H), 2.99-2.86 (m, 2H), 2.76 (s, 6H), 2.69 (s, 4H), 2.58 (s, 3H), 2.40-2.34 (m, 6H), 2.29-2.19 (m, 2H), 2.12-2.07 (m, 3H), 1.95-1.87 (m, 3H). [M+H]+=832.4.

16) The synthesis route of Compound 24 was illustrated as below:

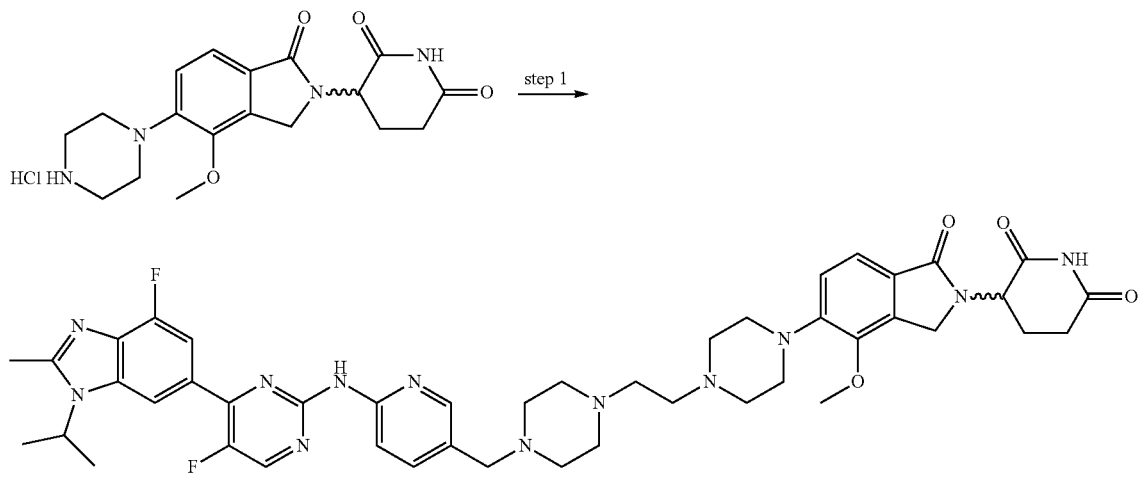

Step 1: Preparation of 3-(5-(4-(2-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)ethyl)piperazin-1-yl)-4-methoxy-1-oxoisoindolin-2-yl)piperidine-2,6-dione 3-(4-Methoxy-1-oxo-5-(piperazin-1-yl)isoindolin-2-yl)piperidine-2,6-dione hydrochloride (40 mg, 0.1 mmol) was dissolved in acetonitrile (10 mL). N-(5-(((4-(2-chloroethyl)piperazin-1-yl)methyl)pyridin-2-yl)-5-fluoro-4-(4-fluoro-1-isopropyl-2-methyl-1H-benzo[d]imidazol-6-yl)pyrimidin-2-amine (54 mg, 0.1 mmol), diisopropylethylamine (129 mg, 1 mmol) and a catalytic amount of potassium iodide were added. The mixture was heated to 80° C. and reacted overnight, concentrated and then purified by a preparative TLC plate to yield a product of 3.7 mg. $^1$HNMR (400 MHz, CDCl$_3$) 8.45-8.40 (m, 2H), 8.26-8.22 (m, 2H), 8.06 (s, 1H), 7.84-7.71 (m, 2H), 7.53 (d, J=8.4 Hz, 1H), 7.04-7.02 (m, 1H), 5.39-5.37 (m, 1H), 4.79-4.75 (m, 1H), 4.44-4.34 (m, 2H), 3.93-3.53 (m, 8H), 3.24 (brs, 4H), 2.73-2.70 (m, 5H), 2.61-2.54 (m, 9H), 2.27-2.23 (m, 2H), 2.07-2.02 (m, 2H) 1.75 (d, J=7.2 Hz, 6H). [M+H]$^+$=863.4.

17) The synthesis route of Compound 16 was illustrated as below:

Step 1: Preparation of 3-(7-methoxy-1-oxo-5-(piperazin-1-yl)isoindolin-2-yl)piperidine-2,6-dione hydrochloride Tert-butyl 4-(2-(2,6-dioxopiperidin-3-yl)-7-methoxy-1-oxoisoindolin-5-yl)piperazine-1-carboxylate (800 mg, 1.74 mmol) was dissolved in dichloromethane (50 mL), and a solution of hydrogen chloride in dioxane (100 mL) was added. The mixture was reacted overnight at room temperature, concentrated and then purified by column chromatography to yield a product of 300 mg. [M+H]$^+$=359.2.

Step 2: Preparation of 3-(5-(4-(2-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperazin-1-yl)-7-methoxy-1-oxoisoindolin-2-yl)piperidine-2,6-dione 3-(7-Methoxy-1-oxo-5-(piperazin-1-yl)isoindolin-2-yl)piperidine-2,6-dione hydrochloride (100 mg, 0.25 mmol) was dissolved in acetonitrile (20 mL). 6-Acetyl-2-((5-(4-(2-bromoethyl)piperazin-1-yl)pyridin-2-yl)amino)-8-cyclopentyl-5-methylpyrido[2,3-d]pyrimidin-7(8H)-one (166 mg, 0.3 mmol), diisopropylethylamine (129 mg, 1 mmol) and a catalytic amount of potassium iodide were added. The mixture was heated to 80° C. and reacted overnight, concentrated and then purified by a preparative TLC plate to yield a product of 23 mg. 1HNMR (400 MHz, CDCl$_3$) δ 8.83 (s, 1H), 8.39 (brs, 1H), 8.21-8.07 (m, 3H), 7.38-7.35 (m, 1H), 6.50 (s, 1H), 6.40 (s, 1H), 5.92-5.88 (m, 1H), 5.20-5.15 (m, 1H), 4.41-4.21 (m, 2H), 3.97 (s, 3H), 3.37 (s, 3H), 3.26 (s, 3H), 2.91-2.73 (m, 10H), 2.58 (s, 3H), 2.40-2.09 (m, 9H), 1.89-1.71 (m, 8H), 1.50-1.43 (m, 2H). [M+H]$^+$=832.4.

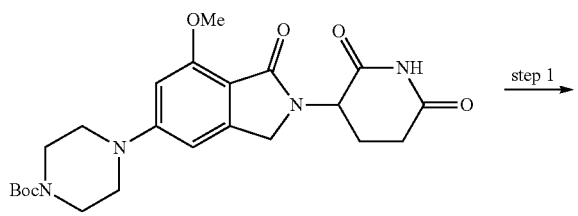
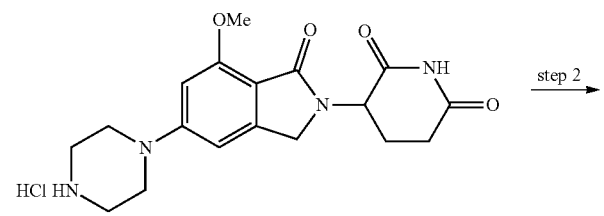

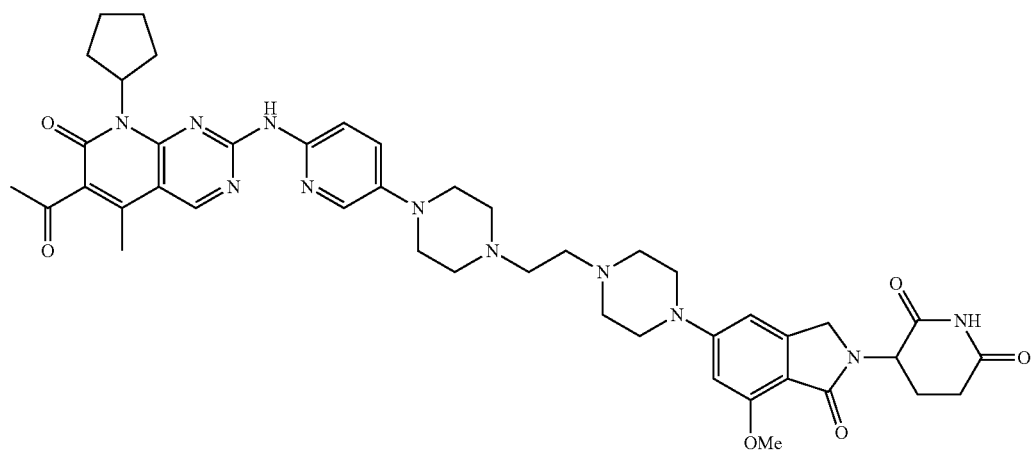

18) The synthesis route of Compound 17 was illustrated as below:

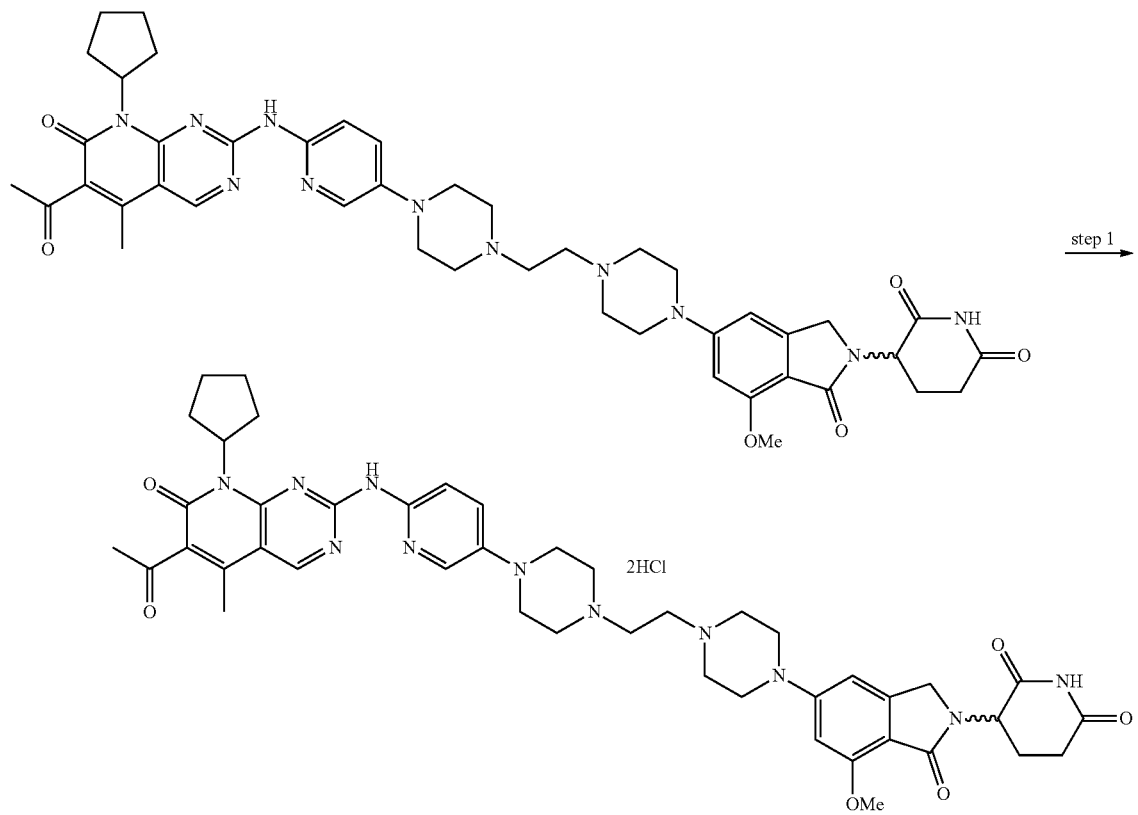

Step 1: Preparation of 3-(5-(4-(2-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperazin-1-yl)-7-methoxy-1-oxoisoindolin-2-yl)piperidine-2,6-dione dihydrochloride 3-(5-(4-(2-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)ethyl)piperazin-1-yl)-7-methoxy-1-oxoisoindolin-2-yl)piperidine-2,6-dione (750 mg, 0.9 mmol) was dissolved in methanol (50 mL), and a solution of hydrogen chloride in methanol (200 mL) was added. The mixture was reacted overnight at room temperature and concentrated to yield a product of 750 mg. $^1$HNMR (400 MHz, d$_6$-DMSO) δ 11.24 (brs, 2H), 10.92 (s, 1H), 9.05 (s, 1H), 8.16-7.89 (m, 3H), 6.74-6.56 (m, 2H), 5.88-5.84 (m, 1H), 5.01-4.97 (m, 1H), 4.30-4.13 (m, 3H), 3.88-3.78 (m, 11H), 3.65-3.55 (m, 4H), 3.35-3.21 (m, 7H), 2.96-2.87 (m, 1H), 2.61-2.56 (m, 1H), 2.46 (s, 3H), 2.37-2.23 (m, 6H), 1.97 (s, 3H), 1.84-1.81 (m, 2H), 1.64-1.60 (m, 2H). [M+H]$^+$= 832.4.

19) The synthesis route of Compound 21 was illustrated as below:

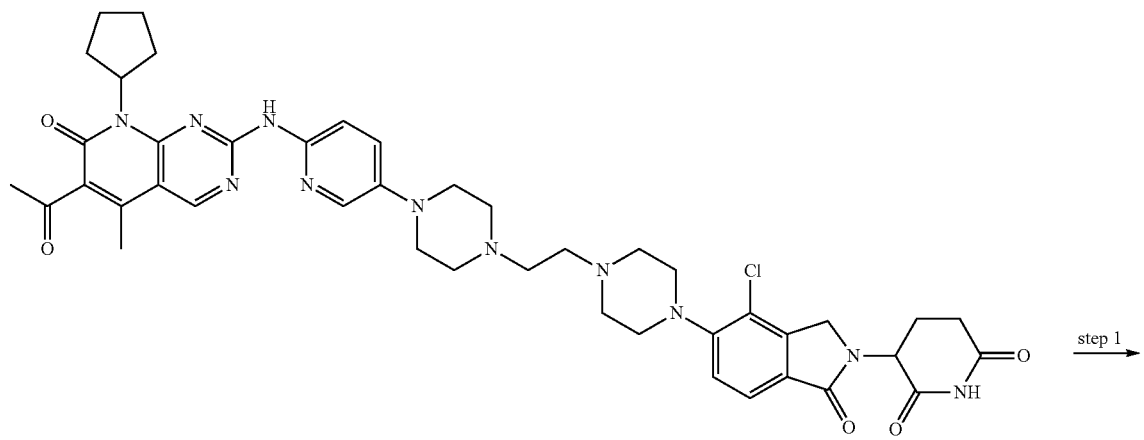

-continued

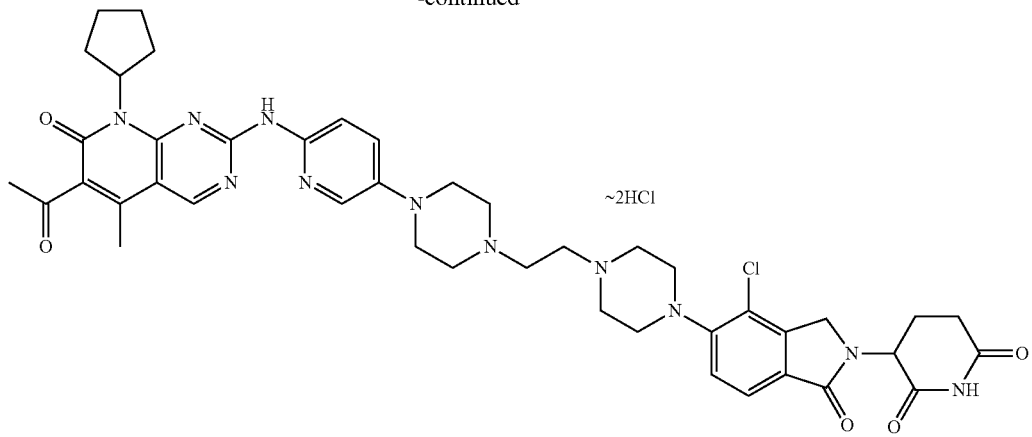

Step 1: Preparation of 3-(5-(4-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperazin-1-yl)-4-chloro-1-oxoisoindolin-2-yl)piperidine-2,6-dione dihydrochloride 3-(5-(4-(2-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)ethyl)piperazin-1-yl)-4-chloro-1-oxoisoindolin-2-yl)piperidine-2,6-dione (22 mg, 0.026 mmol) was dissolved in methanol (5 mL), and a solution of hydrogen chloride in methanol (20 mL) was added. The mixture was reacted overnight at room temperature and concentrated to yield a product of 22 mg. $^1$HNMR (400 MHz, d$_6$-DMSO) (11.01 (s, 1H), 10.62 (brs, 1H), 9.01 (s, 1H), 8.16 (d, J=2 Hz, 1H), 7.91 (d, J=9.2 Hz, 1H), 7.79-7.72 (m, 2H), 7.40 (d, J=8 Hz, 1H), 5.88-5.84 (m, 1H), 5.16-5.11 (m, 1H), 4.49-4.29 (m, 2H), 4.02-3.74 (m, 10H), 3.33-3.06 (m, 8H), 2.98-2.89 (m, 1H), 2.69-2.59 (m, 1H), 2.45 (s, 3H), 2.35 (s, 3H), 2.28-2.22 (m, 2H), 2.04-1.93 (m, 4H), 1.82-1.80 (m, 2H), 1.63-1.60 (m, 2H). [M+H]$^+$=836.4.

20) The synthesis route of Compound 25 was illustrated as below:

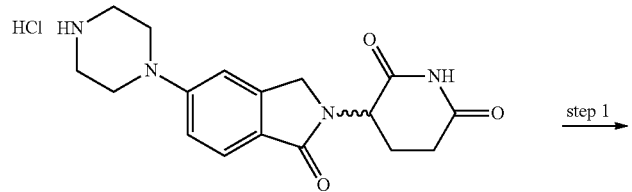

step 1 →

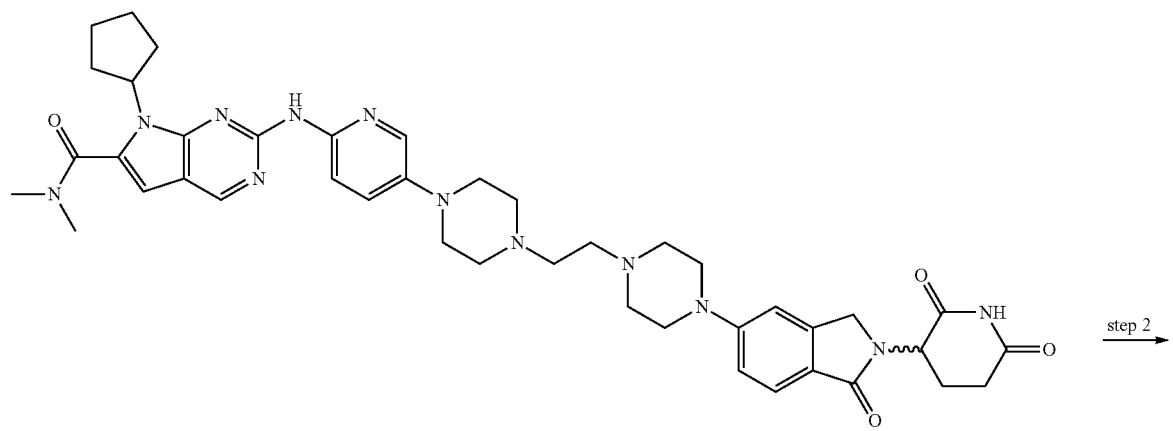

step 2 →

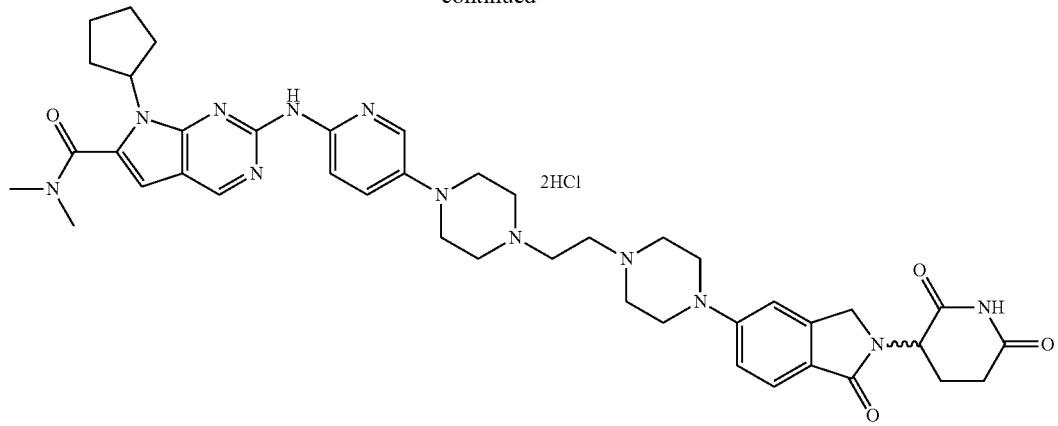

Step 1: Preparation of 7-cyclopentyl-2-((5-(4-(2-(4-(2-(2,6-dioxopiperidin-3-yl)-1-oxoisoindolin-5-yl)piperazin-1-yl)ethyl)piperazin-1-yl)pyridin-2-yl)amino)-N,N-dimethyl-7H-pyrrolo[2,3-d]pyrimidin-6-amide 3-(1-Oxo-5-(piperazin-1-yl)isoindolin-2-yl)piperidine-2,6-dione hydrochloride (100 mg, 0.27 mmol) was dissolved in acetonitrile (10 mL). 2-((5-(4-(2-Bromoethyl)piperazin-1-yl)pyridin-2-yl)amino)-7-cyclopentyl-N,N-dimethyl-7H-pyrrolo[2,3-d]pyrimidin-6-amide (162 mg, 0.3 mmol), diisopropylethylamine (129 mg, 1 mmol) and a catalytic amount of potassium iodide were added. The mixture was heated to 80° C. and reacted overnight, concentrated and then purified by a preparative TLC plate to yield a product of 40 mg. [M+H]⁺=789.4.

Step 2: Preparation of 7-cyclopentyl-2-((5-(4-(2-(4-(2-(2,6-dioxopiperidin-3-yl)-1-oxoisoindolin-5-yl)piperazin-1-yl)ethyl)piperazin-1-yl)pyridin-2-yl)amino)-N,N-dimethyl-7H-pyrrolo[2,3-d]pyrimidin-6-amide dihydrochloride 7-Cyclopentyl-2-((5-(4-(2-(4-(2-(2,6-dioxopiperidin-3-yl)-1-oxoisoindolin-5-yl)piperazin-1-yl)ethyl)piperazin-1-yl)pyridin-2-yl)amino)-N,N-dimethyl-7H-pyrrolo[2,3-d]pyrimidin-6-amide (40 mg, 0.05 mmol) was dissolved in methanol (5 mL), and a solution of hydrogen chloride in methanol (20 mL) was added. The mixture was reacted overnight at room temperature, concentrated and then purified by a preparative TLC plate to yield a product of 35 mg. ¹HNMR (400 MHz, d₆-DMSO) δ 11.60 (brs, 1H), 10.97 (s, 1H), 9.04 (s, 1H), 8.15-8.12 (m, 1H), 8.03 (d, J=2 Hz, 1H), 7.62 (d, J=8.8 Hz, 2H), 7.23-7.19 (m, 2H), 6.87 (s, 1H), 5.10-5.06 (m, 1H), 4.84-4.80 (m, 1H), 4.41-4.24 (m, 2H), 4.01-3.75 (m, 12H), 3.36-3.22 (m, 7H), 3.07 (s, 6H), 2.96-2.88 (m, 1H), 2.63-2.58 (m, 1H), 2.43-2.29 (m, 4H), 2.09-1.99 (m, 5H), 1.69-1.66 (m, 2H). [M+H]⁺=789.4.

21) The synthesis route of Compound 27 was illustrated as below:

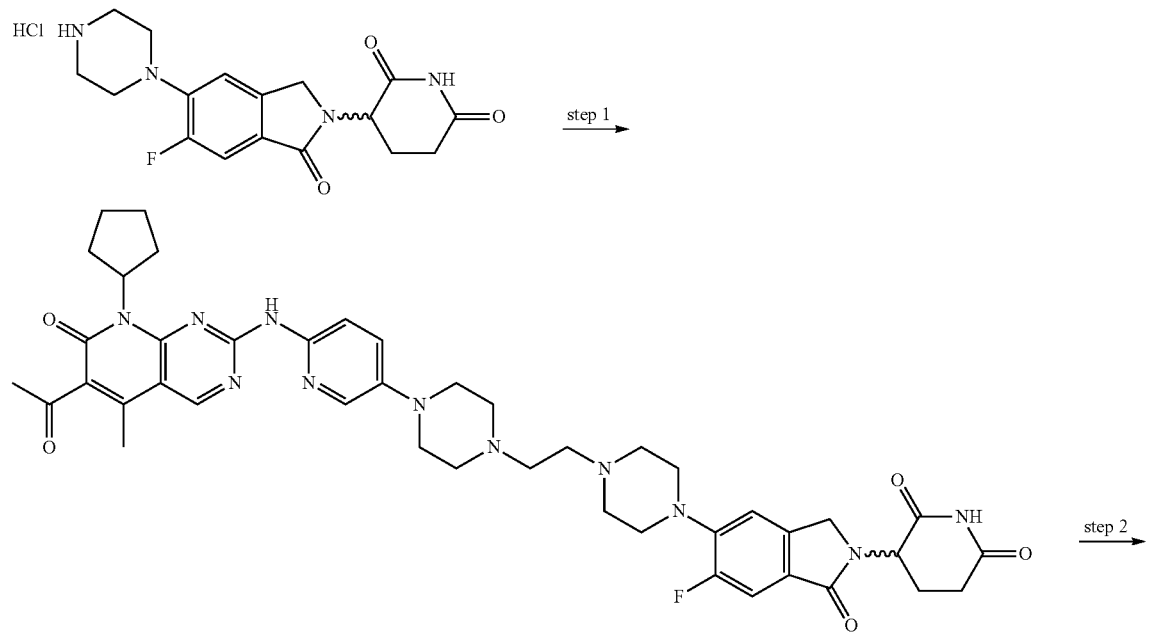

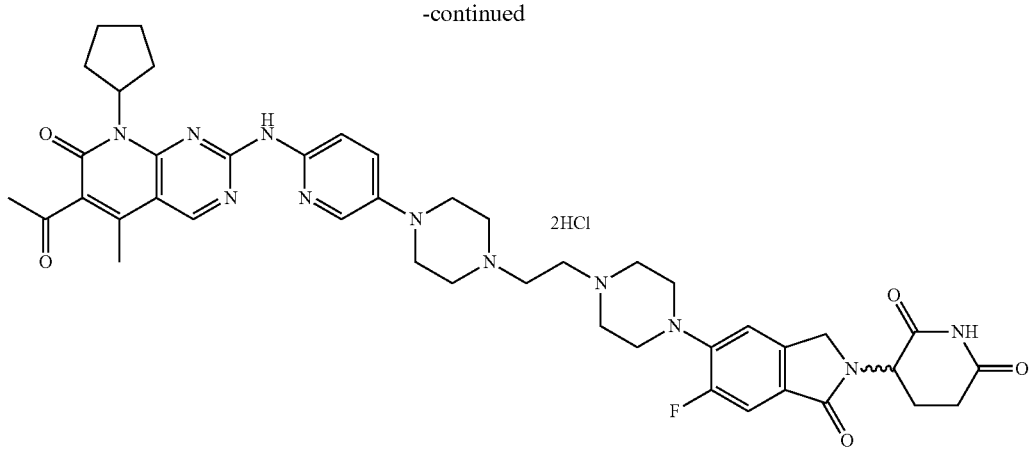

Step 1: Preparation of 3-(5-(4-(2-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperazin-1-yl)-6-fluoro-1-oxoisoindolin-2-yl)piperidine-2,6-dione 3-(6-Fluoro-1-oxo-5-(piperazin-1-yl)isoindolin-2-yl)piperidine-2,6-dione hydrochloride (150 mg, 0.39 mmol) was dissolved in acetonitrile (20 m). 6-Acetyl-2-((5-(4-(2-bromoethyl)piperazin-1-yl)pyridin-2-yl)amino)-8-cyclopentyl-5-methylpyrido[2,3-d]pyrimidin-7(8H)-one (222 mg, 0.4 mmol), diisopropylethylamine (129 mg, 1 mmol) and a catalytic amount of potassium iodide were added. The mixture was heated to 80° C. and reacted overnight, concentrated and then purified by a preparative TLC plate to yield a product of 50 mg. [M+H]$^+$=820.4.

Step 2: Preparation of 3-(5-(4-(2-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperazin-1-yl)-6-fluoro-1-oxoisoindolin-2-yl)piperidine-2,6-dione dihydrochloride 3-(5-(4-(2-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)ethyl)piperazin-1-yl)-6-fluoro-1-oxoisoindolin-2-yl)piperidine-2,6-dione (50 mg, 0.06 mmol) was dissolved in methanol (5 mL), and a solution of hydrogen chloride in methanol (20 mL) was added. The mixture was reacted overnight at room temperature, concentrated and then purified by a preparative TLC plate to yield a product of 18 mg. 1HNMR (400 MHz, d$_6$-DMSO) δ 11.29 (brs, 1H), 11.00 (s, 1H), 9.03 (s, 1H), 8.15 (d, J=1.6 Hz, 1H), 7.95-7.89 (m, 2H), 7.53 (d, J=11.2 Hz, 1H), 7.40 (d, J=7.2 Hz), 5.89-5.84 (m, 1H), 5.12-5.08 (m, 1H), 4.43-4.27 (m, 2H), 3.86-3.52 (m, 12H), 3.35-3.30 (m, 7H), 2.97-2.88 (m, 1H), 2.63-2.58 (m, 1H), 2.45-2.17 (m, 10H), 2.04-1.95 (m, 3H), 1.86-1.78 (m, 2H), 1.65-1.58 (m, 2H). [M+H]$^+$=820.4.

22) The synthesis route of Compound 28 was illustrated as below:

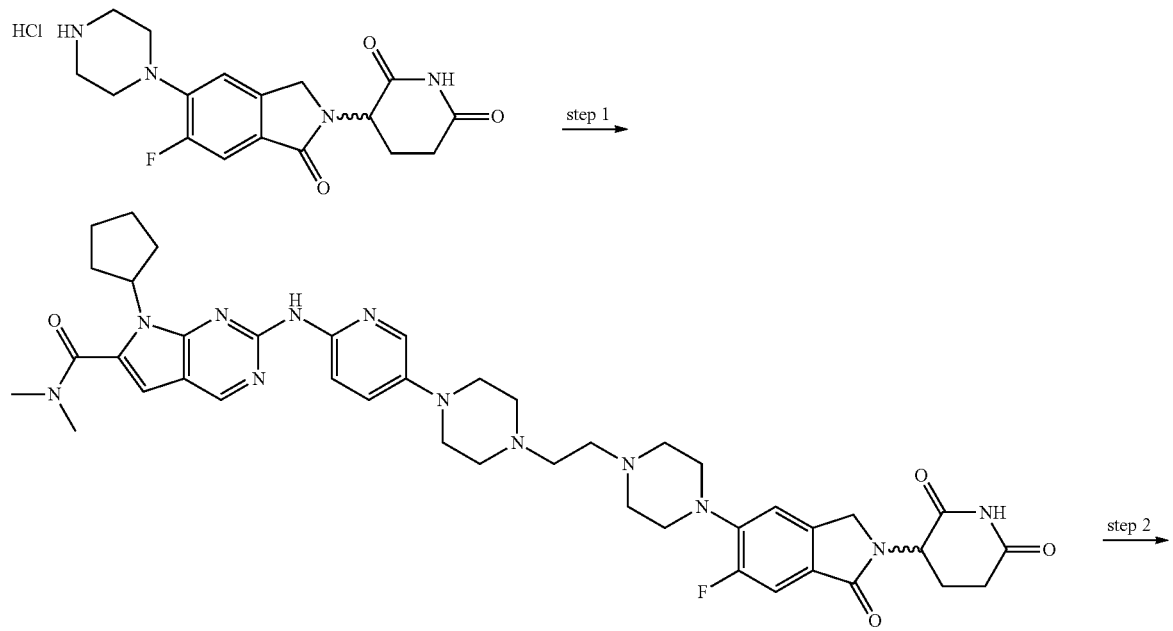

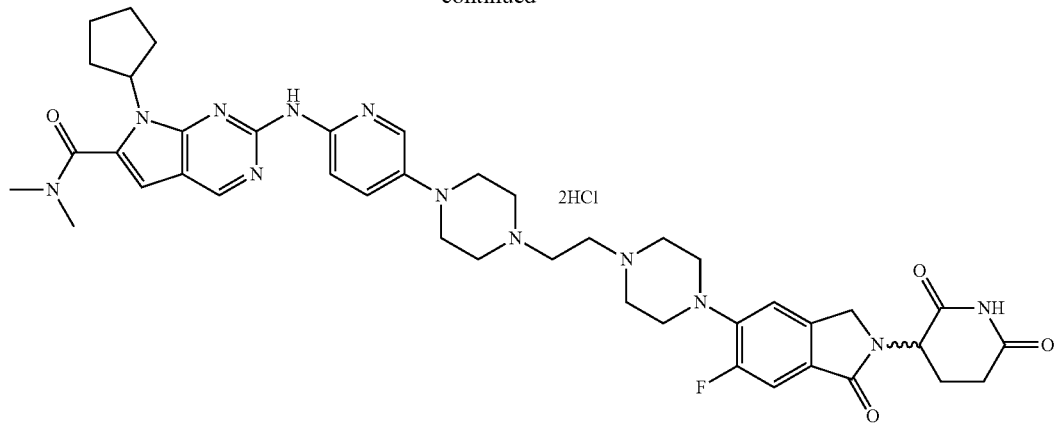

Step 1: Preparation of 7-cyclopentyl-2-((5-(4-(2-(4-(2-(2,6-dioxopiperidin-3-yl)-6-fluoro-1-oxoisoindolin-5-yl)piperazin-1-yl)ethyl)piperazin-1-yl)pyridin-2-yl)amino)-N,N-dimethyl-7H-pyrrolo[2,3-d]pyrimidin-6-amide 3-(6-Fluoro-1-oxo-5-(piperazin-1-yl)isoindolin-2-yl)piperidine-2,6-dione hydrochloride (150 mg, 0.39 mmol) was dissolved in acetonitrile (20 mL). 2-((5-(4-(2-Bromoethyl)piperazin-1-yl)pyridin-2-yl)amino)-7-cyclopentyl-N,N-dimethyl-7H-pyrrolo[2,3-d]pyrimidin-6-amide (216 mg, 0.4 mmol), diisopropylethylamine (129 mg, 1 mmol) and a catalytic amount of potassium iodide were added. The mixture was heated to 80° C. and reacted overnight, concentrated and then purified by a preparative TLC plate to yield a product of 40 mg. [M+H]$^+$=807.4.

Step 2: Preparation of 7-cyclopentyl-2-((5-(4-(2-(4-(2-(2,6-dioxopiperidin-3-yl)-6-fluoro-1-oxoisoindolin-5-yl)piperazin-1-yl)ethyl)piperazin-1-yl)pyridin-2-yl)amino)-N,N-dimethyl-7H-pyrrolo[2,3-d]pyrimidin-6-amide dihydrochloride 7-Cyclopentyl-2-((5-(4-(2-(4-(2-(2,6-dioxopiperidin-3-yl)-6-fluoro-1-oxoisoindolin-5-yl)piperazin-1-yl)ethyl)piperazin-1-yl)pyridin-2-yl)amino)-N,N-dimethyl-7H-pyrrolo[2,3-d]pyrimidin-6-amide (40 mg, 0.05 mmol) was dissolved in methanol (5 mL), and a solution of hydrogen chloride in methanol (20 mL) was added. The mixture was reacted overnight at room temperature, concentrated and then purified by a preparative TLC plate to yield a product of 30 mg. $^1$HNMR (400 MHz, d$_6$-DMSO) δ 11.64 (brs, 1H), 11.47 (brs, 2H), 10.99 (s, 1H), 9.05 (s, 1H), 8.16-8.13 (m, 1H), 8.05 (s, 1H), 7.67 (d, J=9.2 Hz, 1H), 7.54-7.35 (m, 3H), 6.86 (s, 1H), 5.12-5.08 (m, 1H), 4.84-4.80 (m, 1H), 4.43-4.27 (m, 2H), 3.52-3.26 (m, 13H), 3.07 (s, 7H), 2.97-2.87 (m, 1H), 2.68-2.59 (m, 1H), 2.43-2.25 (m, 4H), 2.04-1.99 (m, 6H), 1.69-1.66 (m, 2H). [M+H]$^+$=807.4.

23) The synthesis route of Compound 23 was illustrated as below:

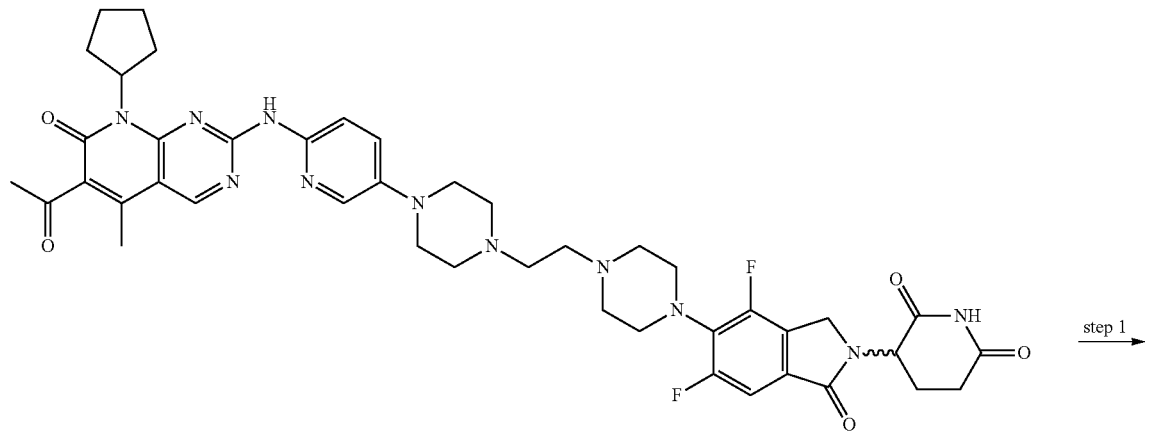

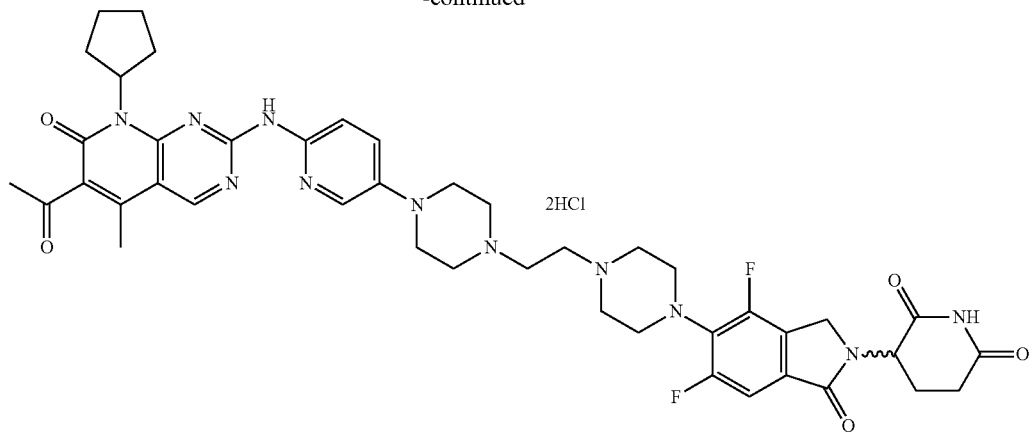

Step 1: Preparation of 3-(5-(4-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperazin-1-yl)-4,6-difluoro-1-oxoisoindolin-2-yl) piperidine-2,6-dione dihydrochloride 3-(5-(4-(2-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)ethyl)piperazin-1-yl)-4,6-difluoro-1-oxoisoindolin-2-yl)piperidine-2,6-dione (30 mg, 0.036 mmol) was dissolved in methanol (5 mL), and a solution of hydrogen chloride in methanol (20 mL) was added. The mixture was reacted overnight at room temperature, concentrated and then purified by a preparative TLC plate to yield a product of 30 mg. HNMR (400 MHz, $d_6$-DMSO) δ 11.02 (brs, 2H), 10.89-10.86 (brs, 1H), 9.02 (s, 1H), 8.15 (s, 1H), 7.89 (s, 2H), 7.51 (d, J=9.6 Hz, 1H), 5.91-5.82 (m, 1H), 5.14-5.09 (m, 1H), 4.55-4.35 (m, 2H), 3.62-3.45 (m, 8H), 3.33-3.26 (m, 6H), 2.97-2.88 (m, 1H), 2.63-2.59 (m, 1H), 2.45-2.21 (m, 9H), 2.02-1.95 (m, 3H), 1.83-1.81 (m, 2H), 1.63-1.61 (m, 2H). [M+H]$^+$=838.4.

24) The synthesis route of Compound 32 was illustrated as below:

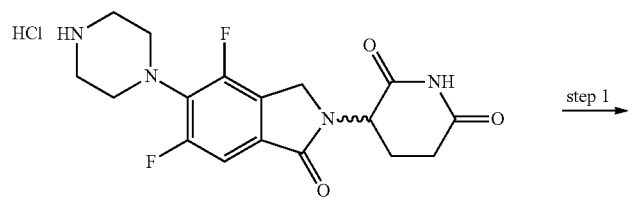

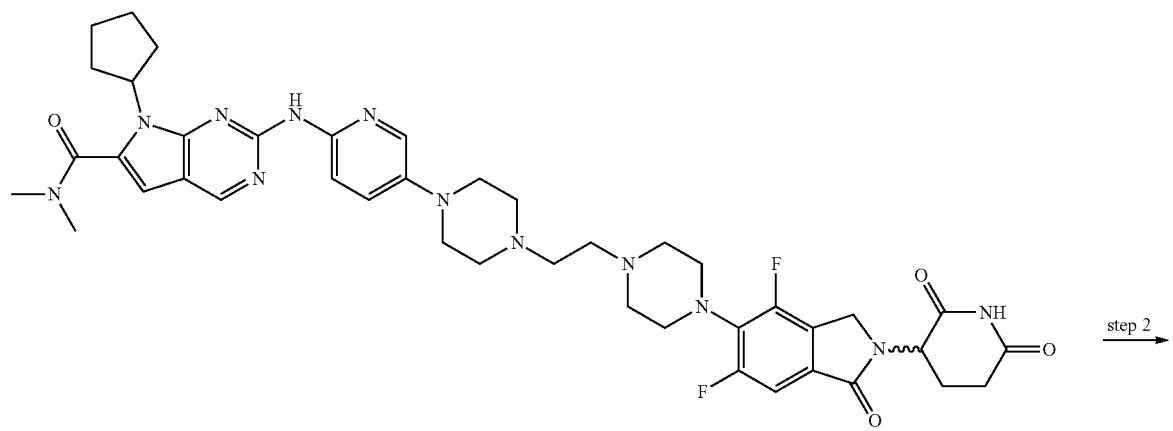

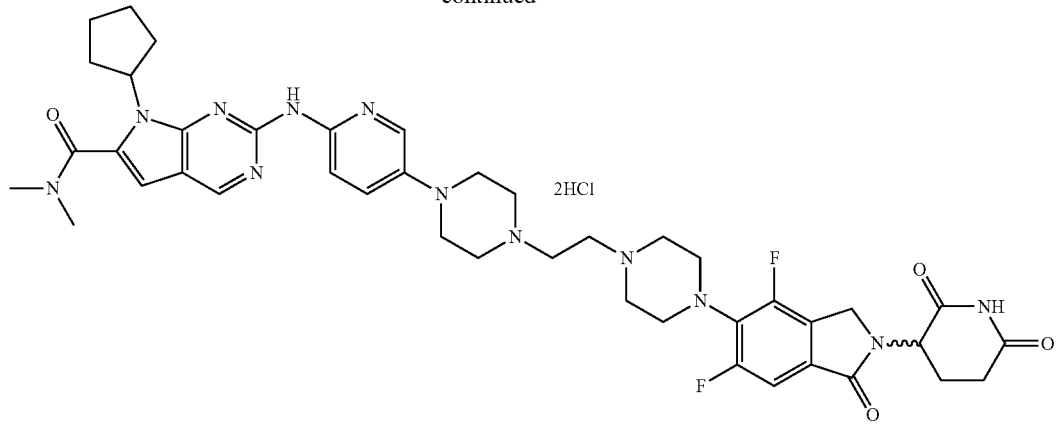

Step 1: Preparation of 7-cyclopentyl-2-((5-(4-(2-(4-(2-(2,6-dioxopiperidin-3-yl)-4,6-difluoro-1-oxoisoindolin-5-yl)piperazin-1-yl)ethyl)piperazin-1-yl)pyridin-2-yl)amino)-N,N-dimethyl-7H-pyrrolo[2,3-d]pyrimidin-6-amide 3-(4,6-Difluoro-1-oxo-5-(piperazin-1-yl)isoindolin-2-yl)piperidine-2,6-dione hydrochloride (80 mg, 0.2 mmol) was dissolved in acetonitrile (20 mL). 2-((5-(4-(2-Bromoethyl)piperazin-1-yl)pyridin-2-yl)amino)-7-cyclopentyl-N,N-dimethyl-7H-pyrrolo[2,3-d]pyrimidin-6-amide (216 mg, 0.4 mmol), diisopropylethylamine (129 mg, 1 mmol) and a catalytic amount of potassium iodide were added. The mixture was heated to 80° C. and reacted overnight, concentrated and then purified by a preparative TLC plate to yield a product of 50 mg. [M+H]$^+$=825.4.

Step 2: Preparation of 7-cyclopentyl-2-((5-(4-(2-(4-(2-(2,6-dioxopiperidin-3-yl)-4,6-difluoro-1-oxoisoindolin-5-yl)piperazin-1-yl)ethyl)piperazin-1-yl)pyridin-2-yl)amino)-N,N-dimethyl-7H-pyrrolo[2,3-d]pyrimidin-6-amide dihydrochloride 7-Cyclopentyl-2-((5-(4-(2-(4-(2-(2,6-dioxopiperidin-3-yl)-4,6-difluoro-1-oxoisoindolin-5-yl)piperazin-1-yl)ethyl)piperazin-1-yl)pyridin-2-yl)amino)-N,N-dimethyl-7H-pyrrolo[2,3-d]pyrimidin-6-amide (50 mg, 0.06 mmol) was dissolved in methanol (5 mL), and a solution of hydrogen chloride in methanol (20 mL) was added. The mixture was reacted overnight at room temperature, concentrated and then purified by a preparative TLC plate to yield a product of 37 mg. $^1$HNMR (400 MHz, d$_6$-DMSO) δ 11.54 (brs, 1H), 11.02 (s, 1H), 9.04 (s, 1H), 8.13-8.10 (m, 1H), 8.03 (s, 1H), 7.61 (d, J=9.2 Hz, 1H), 7.51 (d, J=9.6 Hz, 1H), 6.86 (s, 1H), 5.14-5.09 (m, 1H), 4.85-4.80 (m, 1H), 4.55-4.35 (m, 2H), 3.75-3.58 (m, 12H), 3.07 (s, 6H), 2.98-2.88 (m, 1H), 2.64-2.59 (m, 1H), 2.47-2.41 (m, 1H), 2.36-2.30 (m, 2H), 2.08-1.99 (m, 5H), 1.70-1.65 (m, 2H). [M+H]$^+$=825.4.

25) The synthesis route of Compound 33 was illustrated as below:

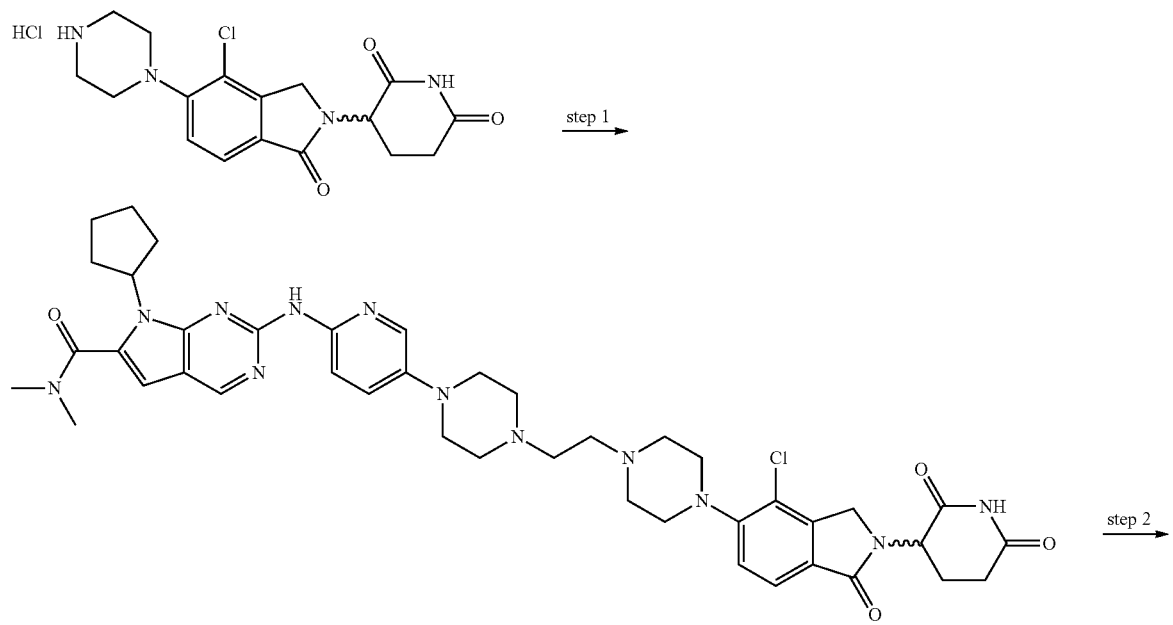

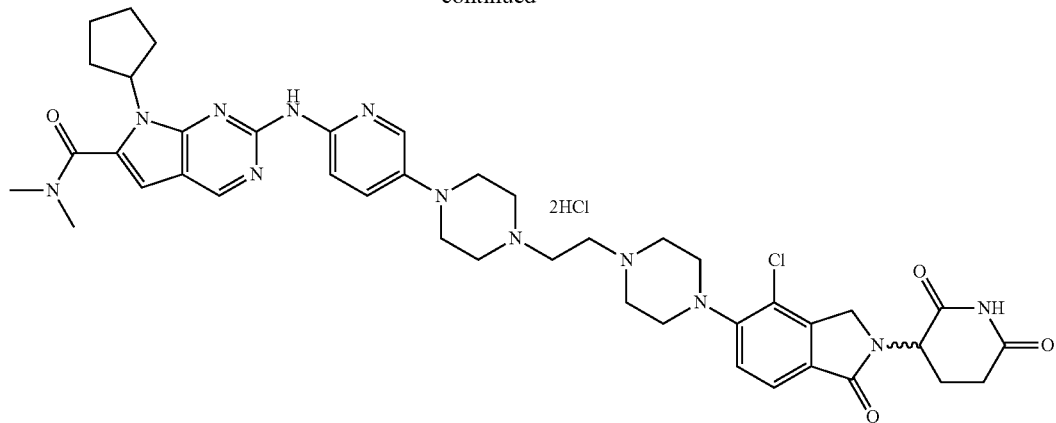

Step 1: Preparation of 2-((5-(4-(2-(4-(4-chloro-2-(2,6-dioxopiperidin-3-yl)-1-oxoisoindolin-5-yl)piperazin-1-yl)ethyl)piperazin-1-yl)pyridin-2-yl)amino)-7-cyclopentyl-N,N-dimethyl-7H-pyrrolo[2,3-d]pyrimidin-6-amide 3-(4-Chloro-1-oxo-5-(piperazin-1-yl)isoindolin-2-yl)piperidine-2,6-dione hydrochloride (100 mg, 0.25 mmol) was dissolved in acetonitrile (20 mL). 2-((5-(4-(2-Bromoethyl)piperazin-1-yl)pyridin-2-yl)amino)-7-cyclopentyl-N,N-dimethyl-7H-pyrrolo[2,3-d]pyrimidin-6-amide (216 mg, 0.4 mmol), diisopropylethylamine (129 mg, 1 mmol) and a catalytic amount of potassium iodide were added. The mixture was heated to 80° C. and reacted overnight, concentrated and then purified by a preparative TLC plate to yield a product of 30 mg. [M+H]$^+$=823.4.

Step 2: Preparation of 2-((5-(4-(2-(4-(4-chloro-2-(2,6-dioxopiperidin-3-yl)-1-oxoisoindolin-5-yl)piperazin-1-yl)ethyl)piperazin-1-yl)pyridin-2-yl)amino)-7-cyclopentyl-N,N-dimethyl-7H-pyrrolo[2,3-d]pyrimidin-6-amide dihydrochloride 2-((5-(4-(2-(4-(4-Chloro-2-(2,6-dioxopiperidin-3-yl)-1-oxoisoindolin-5-yl)piperazin-1-yl)ethyl)piperazin-1-yl)pyridin-2-yl)amino)-7-cyclopentyl-N,N-dimethyl-7H-pyrrolo[2,3-d]pyrimidin-6-amide (30 mg, 0.036 mmol) was dissolved in methanol (5 mL), and a solution of hydrogen chloride in methanol (20 mL) was added. The mixture was reacted overnight at room temperature, concentrated and then purified by a preparative TLC plate to yield a product of 16 mg. $^1$HNMR (400 MHz, d$_6$-DMSO) δ 11.01 (s, 1H), 10.08 (s, 1H), 9.02 (s, 1H), 8.10-8.03 (m, 2H), 7.74-7.67 (m, 2H), 7.47-7.20 (m, 4H), 6.84 (s, 1H), 5.15-5.11 (m, 1H), 4.84-4.80 (m, 1H), 4.49-4.29 (m, 2H), 4.01-3.68 (m, 11H), 3.07 (s, 6H), 2.96-2.89 (m, 1H), 2.65-2.57 (m, 1H), 2.36-2.28 (m, 3H), 2.09-2.00 (m, 6H), 1.69-1.65 (m, 2H), 1.31-1.25 (m, 8H). [M+H]$^+$=823.4.

26) The synthesis route of Compound 19 was illustrated as below:

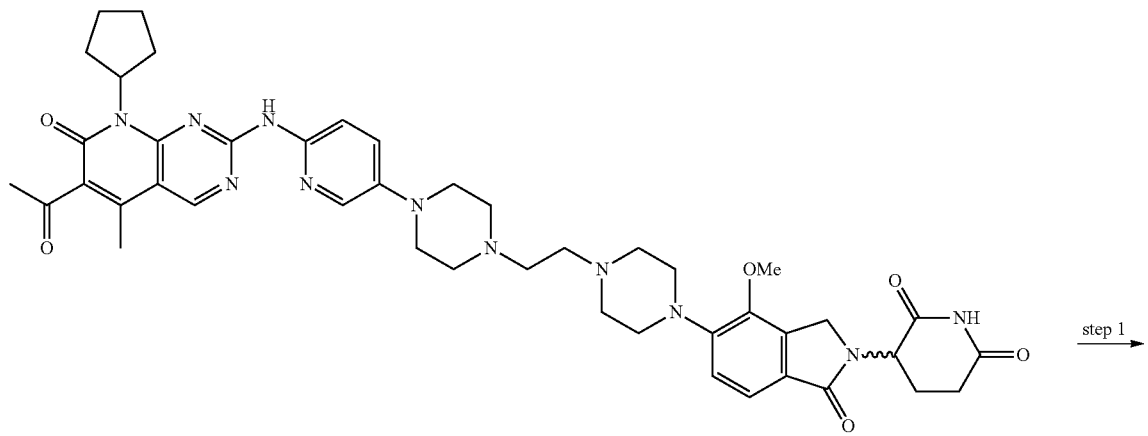

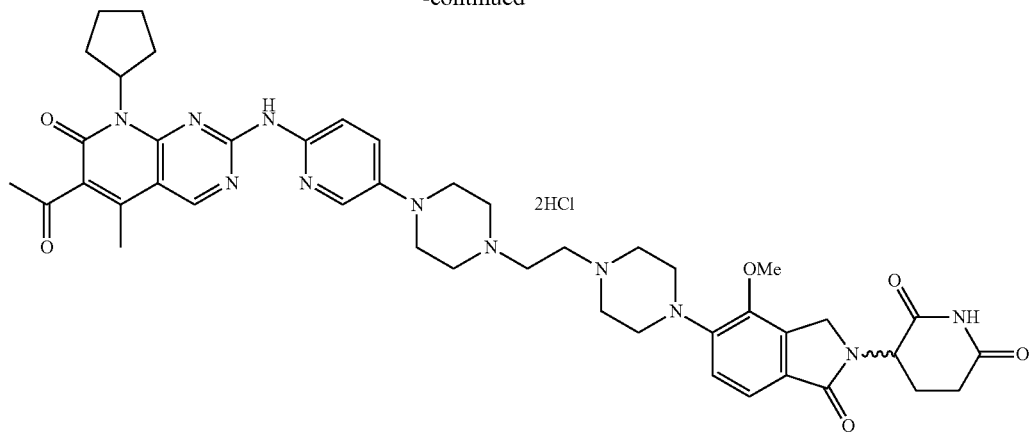

Step 1: Preparation of 3-(5-(4-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperazin-1-yl)-4-methoxy-1-oxoisoindolin-2-yl)piperidine-2,6-dione dihydrochloride 3-(5-(4-(2-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)ethyl)piperazin-1-yl)-4-methoxy-1-oxoisoindolin-2-yl)piperidine-2,6-dione (13 mg, 0.016 mmol) was dissolved in methanol (5 mL), and a solution of hydrogen chloride in methanol (20 mL) was added. The mixture was reacted overnight at room temperature and concentrated to yield a product of 13 mg. $^1$HNMR (400 MHz, d$_6$-DMSO) δ 10.98 (brs, 2H), 8.15-7.89 (m, 2H), 7.45 (d, J=8 Hz, 1H), 7.18 (d, J=8 Hz, 1H), 5.88-5.83 (m, 1H), 5.12-5.07 (m, 1H), 4.56-4.34 (m, 2H), 4.16-3.77 (m, 18H), 2.97-2.88 (m, 2H), 2.63-2.58 (m, 2H), 2.45 (s, 3H), 2.35-2.23 (m, 5H), 2.04-1.92 (m, 4H), 1.87-1.77 (m, 2H), 1.67-1.59 (m, 2H). [M+H]$^+$=832.4.

27) The synthesis route of Compound 30 was illustrated as below:

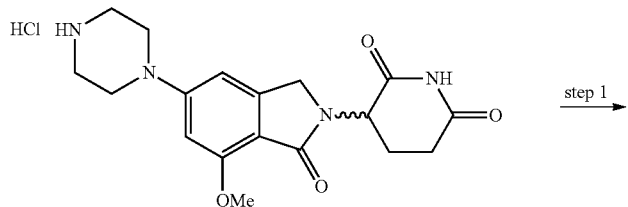

step 1 →

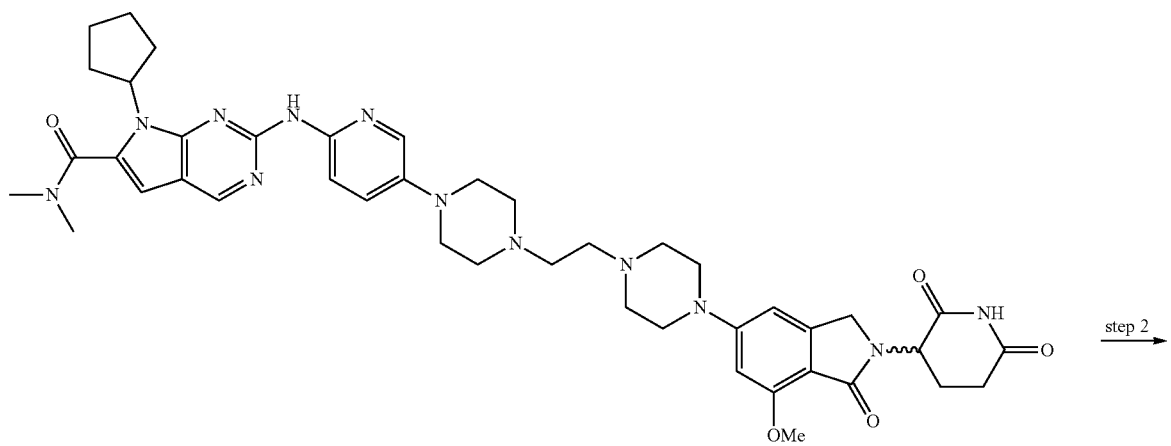

step 2 →

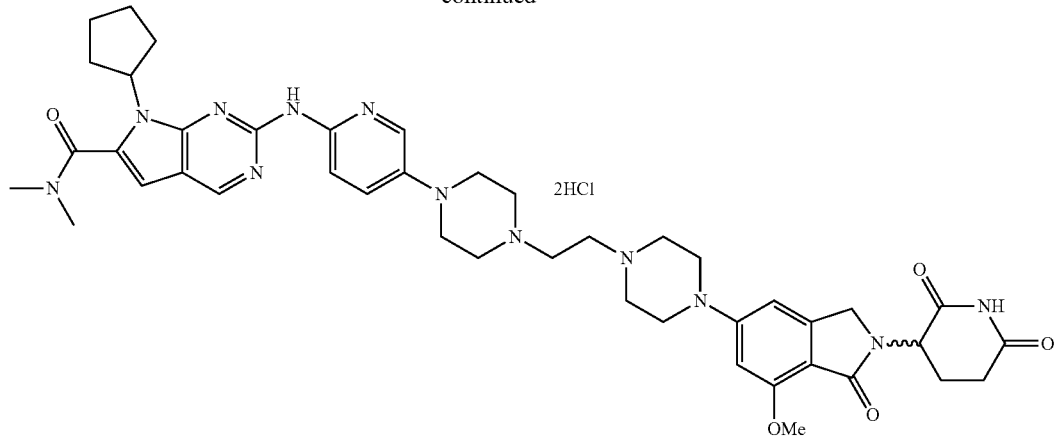

Step 1: Preparation of 7-cyclopentyl-2-((5-(4-(2-(4-(2-(2,6-dioxopiperidin-3-yl)-7-methoxy-1-oxoisoindolin-5-yl)piperazin-1-yl)ethyl)piperazin-1-yl)pyridin-2-yl)amino)-N,N-dimethyl-7H-pyrrolo[2,3-d]pyrimidin-6-amide 3-(7-Methoxy-1-oxo-5-(piperazin-1-yl)isoindolin-2-yl)piperidine-2,6-dione hydrochloride (150 mg, 0.38 mmol) was dissolved in acetonitrile (20 mL). 2-((5-(4-(2-Bromoethyl)piperazin-1-yl)pyridin-2-yl)amino)-7-cyclopentyl-N,N-dimethyl-7H-pyrrolo[2,3-d]pyrimidin-6-amide (217 mg, 0.4 mmol), diisopropylethylamine (129 mg, 1 mmol) and a catalytic amount of potassium iodide were added. The mixture was heated to 80° C. and reacted overnight, concentrated and then purified by a preparative TLC plate to yield a product of 25 mg. [M+H]$^+$=819.4.

Step 2: Preparation of 7-cyclopentyl-2-((5-(4-(2-(4-(2-(2,6-dioxopiperidin-3-yl)-7-methoxy-1-oxoisoindolin-5-yl)piperazin-1-yl)ethyl)piperazin-1-yl)pyridin-2-yl)amino)-N,N-dimethyl-7H-pyrrolo[2,3-d]pyrimidin-6-amide dihydrochloride 7-Cyclopentyl-2-((5-(4-(2-(4-(2-(2,6-dioxopiperidin-3-yl)-7-methoxy-1-oxoisoindolin-5-yl)piperazin-1-yl)ethyl)piperazin-1-yl)pyridin-2-yl)amino)-N,N-dimethyl-7H-pyrrolo[2,3-d]pyrimidin-6-amide (25 mg, 0.03 mmol) was dissolved in methanol (5 mL), and a solution of hydrogen chloride in methanol (20 mL) was added. The mixture was reacted overnight at room temperature, concentrated and then purified by a preparative TLC plate to yield a product of 6.5 mg. $^1$HNMR (400 MHz, d$_6$-DMSO) δ 8.72 (s, 1H), 8.42-8.40 (m, 1H), 8.03-8.02 (m, 1H), 7.55 (s, 1H), 7.38-7.36 (m, 1H), 7.03 (s, 1H), 6.51-6.38 (m, 3H), 5.39-5.37 (m, 1H), 4.85-4.80 (m, 1H), 4.49-4.28 (m, 2H), 3.96 (s, 3H), 3.63-3.38 (m, 8H), 3.19 (s, 6H), 3.15-3.13 (m, 1H), 2.97-2.84 (m, 6H), 2.65-2.55 (m, 2H), 2.30-2.21 (m, 3H), 2.13-2.02 (m, 6H), 1.70-1.60 (m, 4H). [M+H]$^+$=819.4.

28) The synthesis route of Compound 31 was illustrated as below:

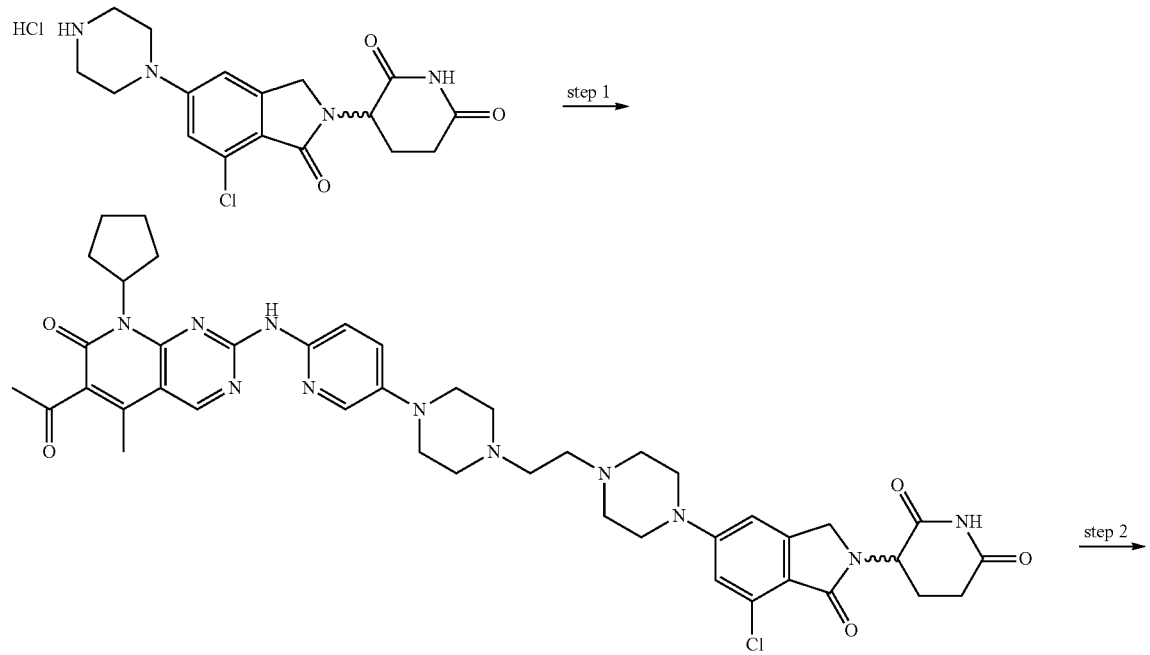

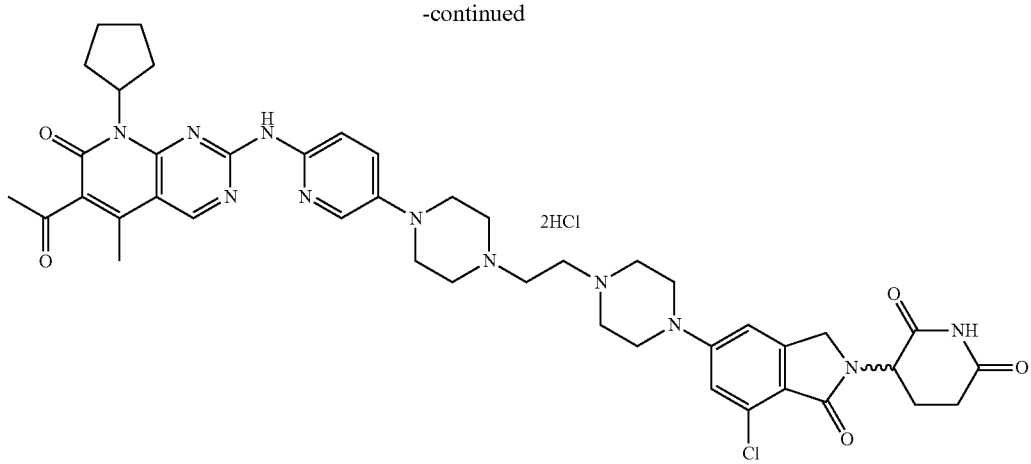

Step 1: Preparation of 3-(5-(4-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperazin-1-yl)-7-chloro-1-oxoisoindolin-2-yl)piperidine-2,6-dione 3-(7-Chloro-1-oxo-5-(piperazin-1-yl)isoindolin-2-yl)piperidine-2,6-dione hydrochloride (150 mg, 0.37 mmol) was dissolved in acetonitrile (20 mL). 6-Acetyl-2-((5-(4-(2-bromoethyl)piperazin-1-yl)pyridin-2-yl)amino)-8-cyclopentyl-5-methylpyrido[2,3-d]pyrimidin-7(8H)-one (222 mg, 0.4 mmol), diisopropylethylamine (129 mg, 1 mmol) and a catalytic amount of potassium iodide were added. The mixture was heated to 80° C. and reacted overnight, concentrated and then purified by a preparative TLC plate to yield a product of 20 mg. [M+H]$^+$=836.4.

Step 2: Preparation of 3-(5-(4-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperazin-1-yl)-7-chloro-1-oxoisoindolin-2-yl)piperidine-2,6-dione dihydrochloride 3-(5-(4-(2-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)ethyl)piperazin-1-yl)-7-chloro-1-oxoisoindolin-2-yl)piperidine-2,6-dione (20 mg, 0.024 mmol) was dissolved in methanol (5 mL), and a solution of hydrogen chloride in methanol (20 mL) was added. The mixture was reacted overnight at room temperature, concentrated and then purified by a preparative TLC plate to yield a product of 7.5 mg. $^1$HNMR (400 MHz, CD$_3$OD) (9.17 (s, 1H), 8.28-8.25 (m, 1H), 8.02 (d, J=0.8 Hz, 1H), 7.61 (d, J=9.6 Hz, 1H), 7.14 (d, J=4 Hz, 1H), 6.06-6.02 (m, 1H), 5.14-5.09 (m, 1H), 4.49-4.38 (m, 2H), 3.76-3.42 (m, 15H), 2.97-2.77 (m, 3H), 2.53 (s, 3H), 2.47 (s, 3H), 2.39-2.30 (m, 2H), 2.24-2.02 (m, 6H), 1.98-1.89 (m, 2H), 1.76-1.59 (m, 4H). [M+H]$^+$=836.4.

29) The synthesis route of Compound 13 was illustrated as below:

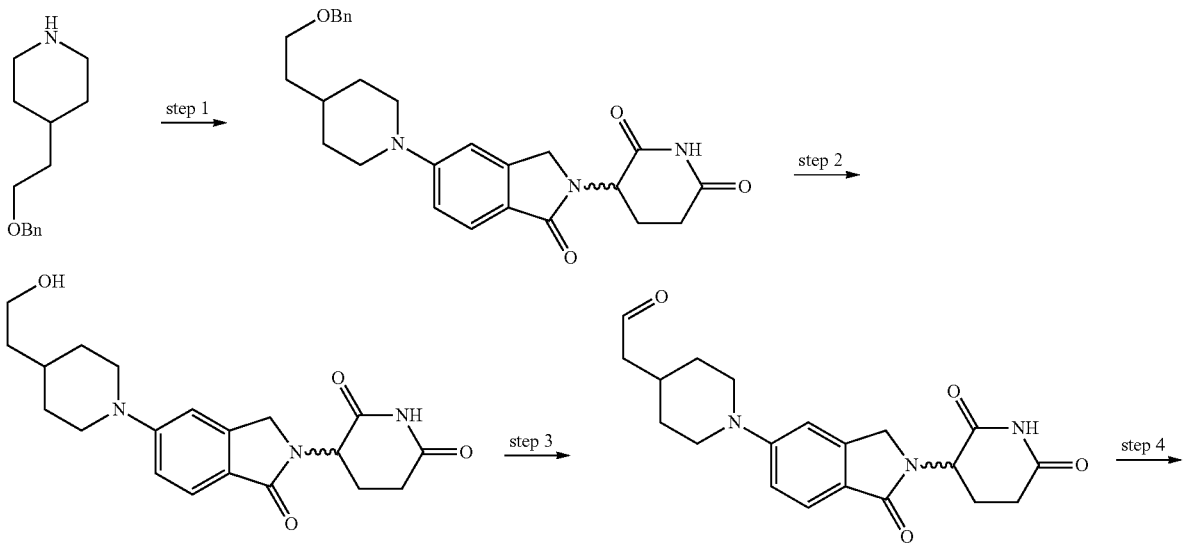

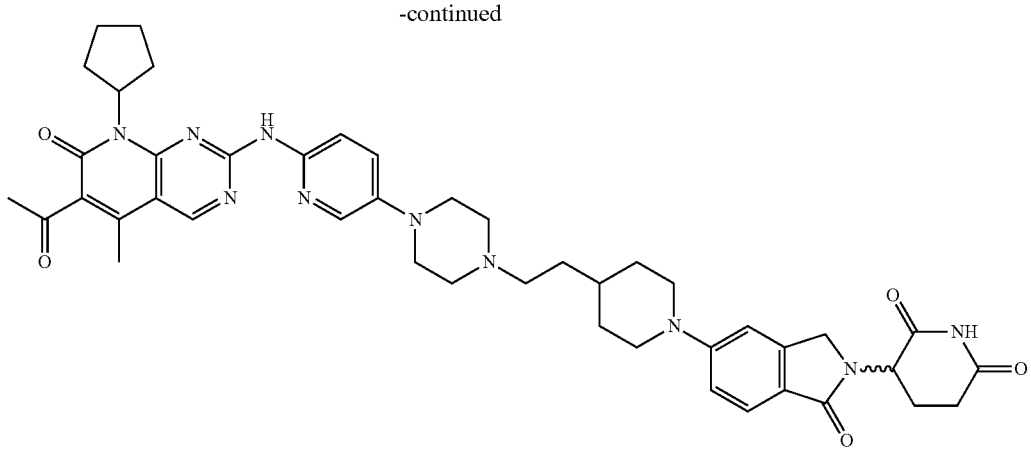

Step 1: Preparation of 3-(5-(4-(2-(benzyloxy)ethyl) piperidin-1-yl)-1-oxoisoindolin-2-yl)piperidine-2,6-dione 4-(2-(Benzyloxy)ethyl)piperidine (300 mg, 1.37 mmol) was dissolved in dioxane (20 mL)

3-(5-Bromo-1-oxoisoindolin-2-yl)piperidine-2,6-dione (808 mg, 2.5 mmol), palladium acetate (67 mg, 0.3 mmol), X-Phos (286 mg, 0.6 mmol) and cesium carbonate (977 mg, 3 mmol) were added. The mixture was heated to 105° C. and reacted for two days under nitrogen atmosphere, cooled, filtered, concentrated, and then purified by column chromatography and preparative liquid chromatography to yield a product of 80 mg. [M+H]$^+$=462.2.

Step 2: Preparation of 3-(5-(4-(2-hydroxyethyl)piperidin-1-yl)-1-oxoisoindolin-2-yl)piperidine-2,6-dione 3-(5-(4-(2-(Benzyloxy)ethyl)piperidin-1-yl)-1-oxoisoindolin-2-yl)piperidine-2,6-dione (80 mg, 0.17 mmol) was dissolved in methanol (20 mL), and an appropriate amount of 10% Pd/C was added. The mixture was reacted overnight at room temperature under hydrogen atmosphere, filtered, concentrated and then purified by a preparative TLC plate to yield a product of 40 mg. [M+H]$^+$=372.2.

Step 3: Preparation of 2-(1-(2-(2,6-dioxopiperidin-3-yl)-1-oxoisoindolin-5-yl)piperidin-4-yl)acetaldehyde 3-(5-(4-(2-Hydroxyethyl)piperidin-1-yl)-1-oxoisoindolin-2-yl)piperidine-2,6-dione (40 mg, 0.11 mmol) was dissolved in dichloromethane (10 mL), and Dess-Martin reagent (85 mg, 0.2 mmol) was added. The mixture was reacted at room temperature until the raw material disappeared, filtered and then purified by a preparative TLC plate to yield a product of 10 mg. [M+H]$^+$=370.2.

Step 4: Preparation of 3-(5-(4-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperidin-1-yl)-1-oxoisoindolin-2-yl) piperidine-2,6-dione 2-(1-(2-(2,6-Dioxopiperidin-3-yl)-1-oxoisoindolin-5-yl) piperidin-4-yl)acetaldehyde (10 mg, 0.027 mmol) was dissolved in 1,2-dichloroethane (10 mL). Palbociclib (13.4 mg, 0.03 mmol), sodium triacetoxyborohydride (21.2 mg, 0.1 mmol) and a catalytic amount of acetic acid were added. The mixture was reacted overnight at room temperature, filtered, concentrated and then purified by a preparative TLC plate to yield a product of 3.3 mg. $^1$HNMR (400 MHz, CDCl$_3$) δ 8.83 (s, 1H), 8.32 (brs, 1H), 8.18 (brs, 1H), 8.07 (d, J=2.8 Hz, 1H), 7.74 (d, J=8.8 Hz, 1H), 7.39-7.36 (m, 1H), 7.03-7.00 (m, 1H), 6.90 (d, J=1.2 Hz, 1H), 5.91-5.86 (m, 1H), 5.25-5.20 (m, 1H), 4.45-4.26 (m, 2H), 3.86 (d, J=12.8 Hz, 2H), 3.28 (s, 4H), 2.92-2.85 (m, 4H), 2.73 (s, 4H), 2.57 (s, 5H), 2.40-2.31 (m, 6H), 2.27-2.19 (m, 2H), 2.11-2.03 (m, 3H), 1.91-1.76 (m, 8H). [M+H]$^+$=801.4.

30) The synthesis route of Compound 41 was illustrated as below:

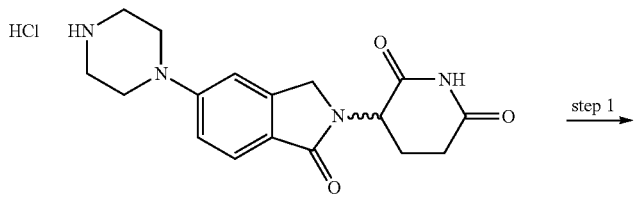

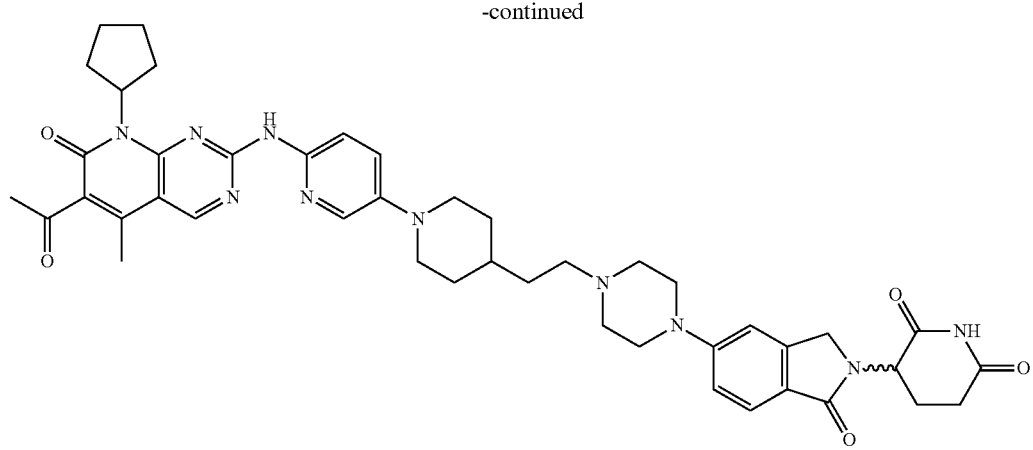

Step 1: Preparation of 3-(5-(4-(2-(1-(6-((6-acetyl-8-cyclopentyl-5-methyl-7-oxo-7,8-dihydropyrido[2,3-d]pyrimidin-2-yl)amino)pyridin-3-yl)piperidin-4-yl)ethyl)piperazin-1-yl)-1-oxoisoindolin-2-yl)piperidine-2,6-dione 3-(1-Oxo-5-(piperazin-1-yl)isoindolin-2-yl)piperidine-2,6-dione hydrochloride (91.2 mg, 0.25 mmol) was dissolved in dimethylformamide (10 mL), and 6-acetyl-2-((5-(4-(2-chloroethyl)piperidin-1-yl)pyridin-2-yl)amino)-8-cyclopentyl-5-methylpyrido[2,3-d]pyrimidin-7(8H)-one (130 mg, 0.25 mmol) and potassium carbonate (138 mg, 1 mmol) were added. The mixture was heated to 80° C. and reacted overnight, filtered, concentrated and then purified by a preparative TLC plate to yield a product of 3.37 mg. $^1$HNMR (400 MHz, CDCl$_3$) δ 8.80 (s, 1H), 7.99 (brs, 2H), 7.80-7.77 (m, 1H), 7.40-7.37 (m, 1H), 7.04-6.90 (m, 2H), 5.89-5.84 (m, 1H), 5.17-5.12 (m, 1H), 4.41-4.29 (m, 2H), 3.88-3.84 (m, 2H), 3.67-3.59 (m, 5H), 3.43-3.30 (m, 4H), 3.03-2.72 (m, 4H), 2.55 (s, 3H), 2.37-2.30 (m, 6H), 2.24-2.15 (m, 2H) 1.68-1.31 (m, 13H). [M+H]$^+$=801.4.

31) The synthesis route of Compound 43 was illustrated as below:

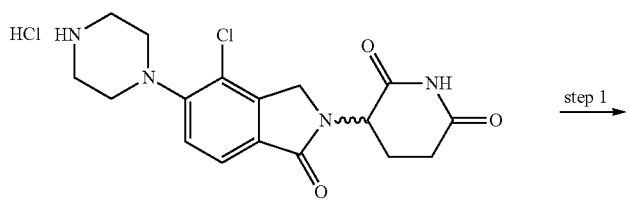

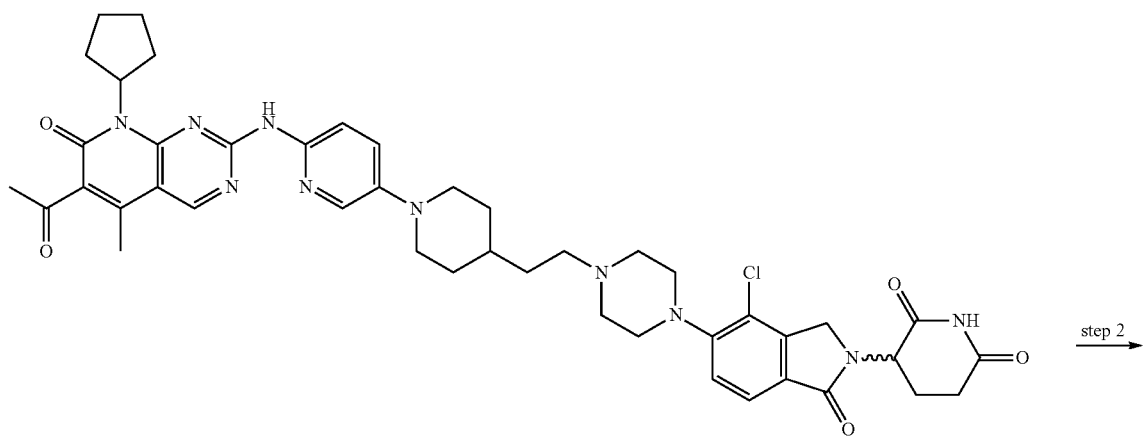

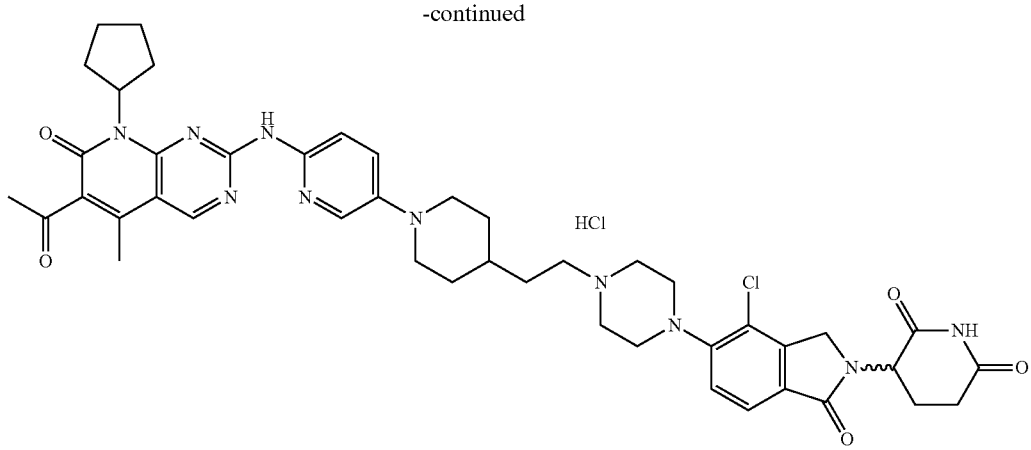

Step 1: Preparation of 3-(5-(4-(2-(1-(6-((6-acetyl-8-cyclopentyl-5-methyl-7-oxo-7,8-dihydropyrido[2,3-d]pyrimidin-2-yl)amino)pyridin-3-yl)piperidin-4-yl)ethyl)piperazin-1-yl)-4-chloro-1-oxoisoindolin-2-yl)piperidine-2,6-dione 3-(4-Chloro-1-oxo-5-(piperazin-1-yl)isoindolin-2-yl)piperidine-2,6-dione hydrochloride (80 mg, 0.2 mmol) was dissolved in dimethylformamide (10 mL), and 6-acetyl-2-((5-(4-(2-chloroethyl)piperidin-1-yl)pyridin-2-yl)amino)-8-cyclopentyl-5-methylpyrido[2,3-d]pyrimidin-7(8H)-one (100 mg, 0.2 mmol) and potassium carbonate (138 mg, 1 mmol) were added. The mixture was heated to 100° C. and reacted overnight, filtered, concentrated and then purified by a preparative TLC plate to yield a product of 23 mg. [M+H]*=835.4.

Step 2: Preparation of 3-(5-(4-(2-(1-(6-((6-acetyl-8-cyclopentyl-5-methyl-7-oxo-7,8-dihydropyrido[2,3-d]pyrimidin-2-yl)amino)pyridin-3-yl)piperidin-4-yl)ethyl)piperazin-1-yl)-4-chloro-1-oxoisoindolin-2-yl)piperidine-2,6-dione hydrochloride 3-(5-(4-(2-(1-(6-((6-Acetyl-8-cyclopentyl-5-methyl-7-oxo-7,8-dihydropyrido[2,3-d]pyrimidin-2-yl)amino)pyridin-3-yl)piperidin-4-yl)ethyl)piperazin-1-yl)-4-chloro-1-oxoisoindolin-2-yl)piperidine-2,6-dione (20 mg, 0.024 mmol) was dissolved in methanol (5 mL), and a solution of hydrogen chloride in methanol (20 mL) was added. The mixture was reacted overnight at room temperature and concentrated to yield a product of 20 mg. $^1$HNMR (400 MHz, CDCl$_3$) δ 9.06 (brs, 1H), 8.88 (s, 1H), 8.10 (s, 2H), 7.78 (d, J=8 Hz, 1H), 7.35-7.33 (m, 1H), 7.21 (d, J=8 Hz, 1H), 5.93-5.84 (m, 1H), 5.20-5.16 (m, 1H), 4.42-4.31 (m, 2H), 3.86 (s, 2H), 3.63-3.46 (m, 10H), 3.05-2.74 (m, 4H), 2.56 (s, 3H), 2.38 (s, 6H), 2.24-1.88 (m, 8H), 1.54-1.43 (m, 6H). [M+H]$^+$=835.4.

32) The synthesis route of Compound 14 was illustrated as below:

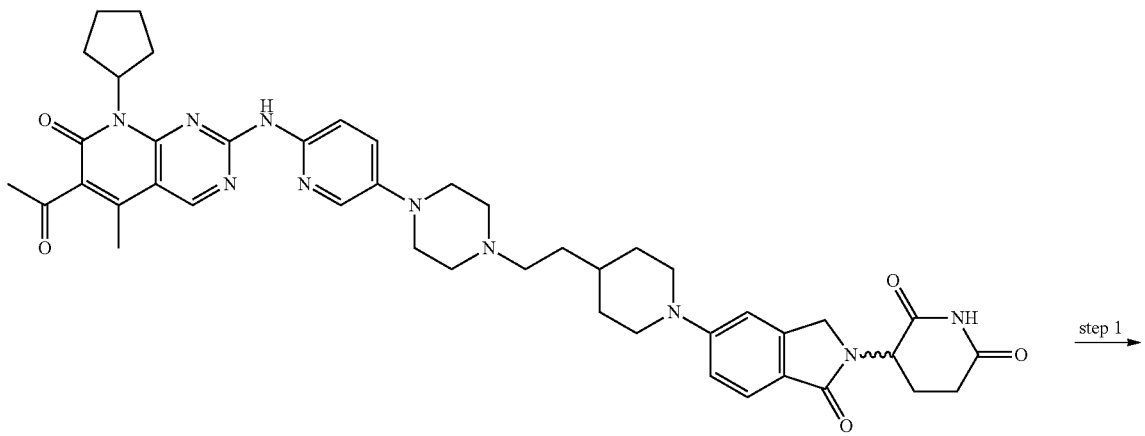

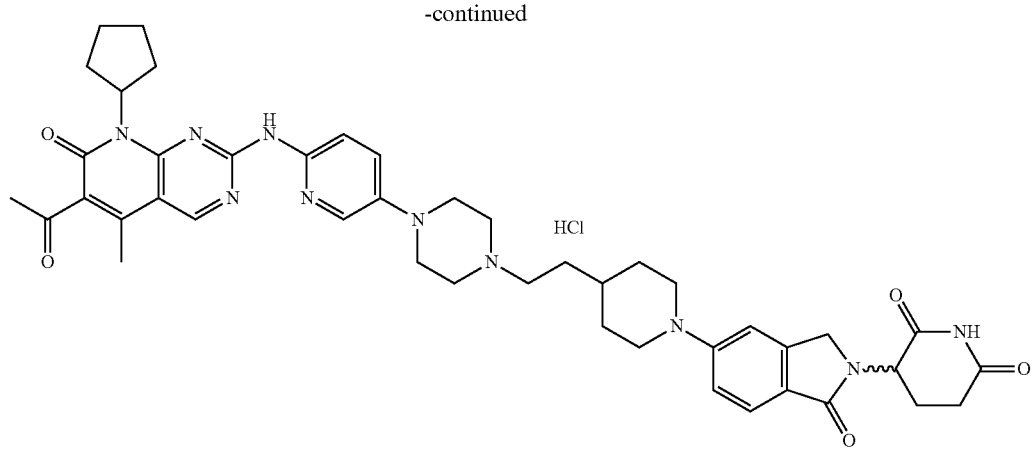

Step 1: Preparation of 3-(5-(4-(2-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperidin-1-yl)-1-oxoisoindolin-2-yl)piperidine-2,6-dione hydrochloride 3-(5-(4-(2-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)ethyl)piperidin-1-yl)-1-oxoisoindolin-2-yl)piperidine-2,6-dione (30 mg, 0.037 mmol) was dissolved in methanol (5 mL), and a solution of hydrogen chloride in methanol (20 mL) was added. The mixture was reacted overnight at room temperature, concentrated and then purified by a preparative TLC plate to yield a product of 27.4 mg. $^1$HNMR (400 MHz, CD$_3$OD) δ 9.18 (s, 1H), 8.32-8.29 (m, 1H), 8.06-8.01 (m, 3H), 7.92-7.90 (m, 1H), 7.61 (d, J=9.6 Hz, 1H), 6.09-6.00 (m, 1H), 5.23-5.18 (m, 1H), 4.69-4.58 (m, 2H), 4.03-3.97 (m, 2H), 3.86-3.76 (m, 7H), 3.45-3.497 (m, 6H), 3.00-2.90 (m, 1H), 2.85-2.79 (m, 1H), 2.60-2.56 (m, 1H), 2.53 (s, 3H), 2.47 (s, 3H), 2.37-2.22 (m, 6H), 2.17-2.12 (m, 2H), 2.03-1.89 (m, 7H). [M+H] d=801.4.

W was methylene or carbonyl; Y was methylene or carbonyl; the ring consisting of X1 to X6 was piperidine ring or valerolactam ring; the ring consisting of Z1 to Z6 was piperazine ring; and R was absent.

6

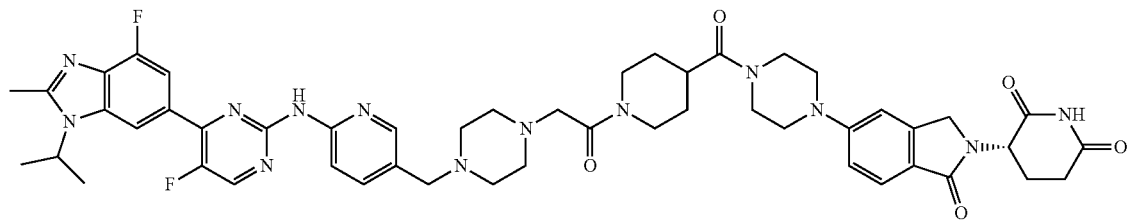

7

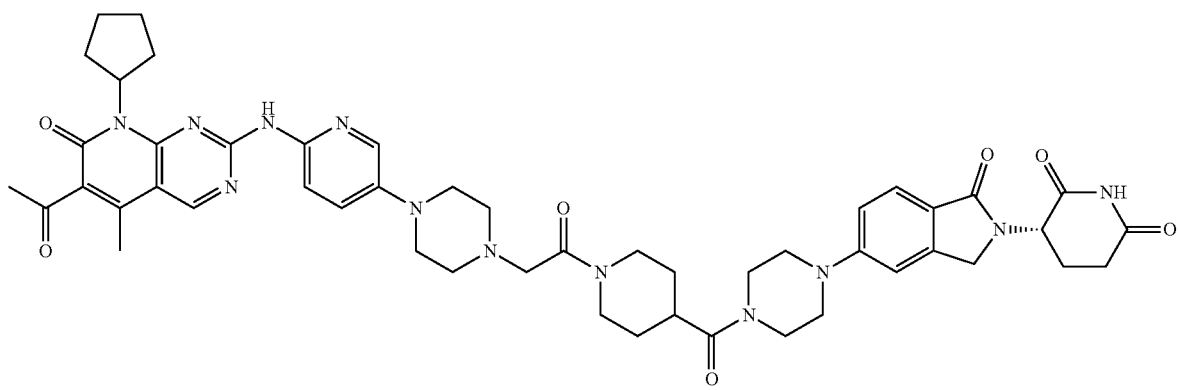

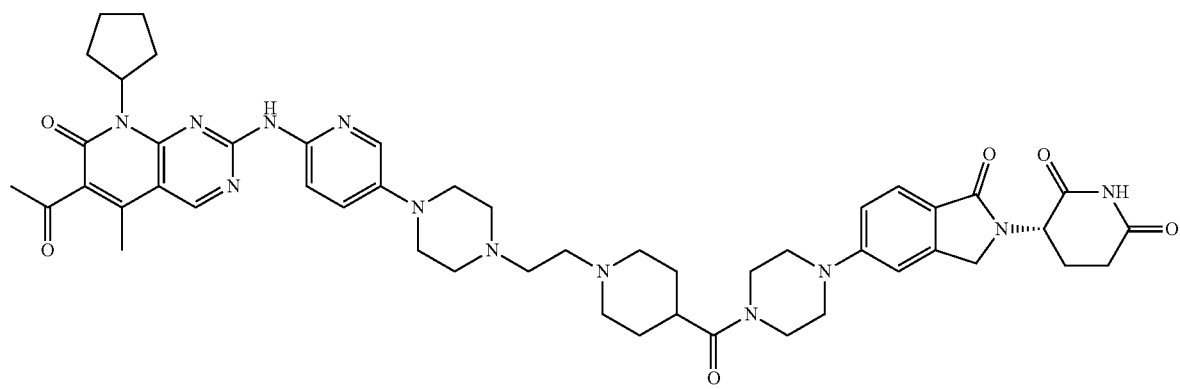
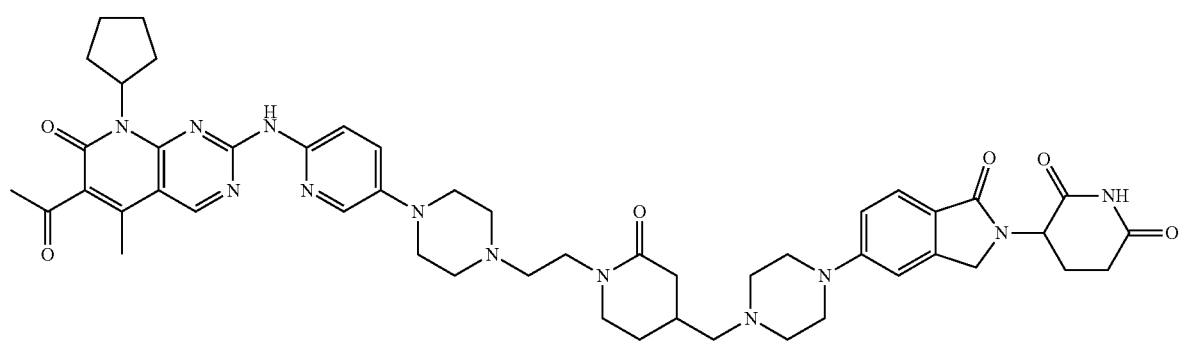
33) The synthesis route of Compound 6 was illustrated as below:
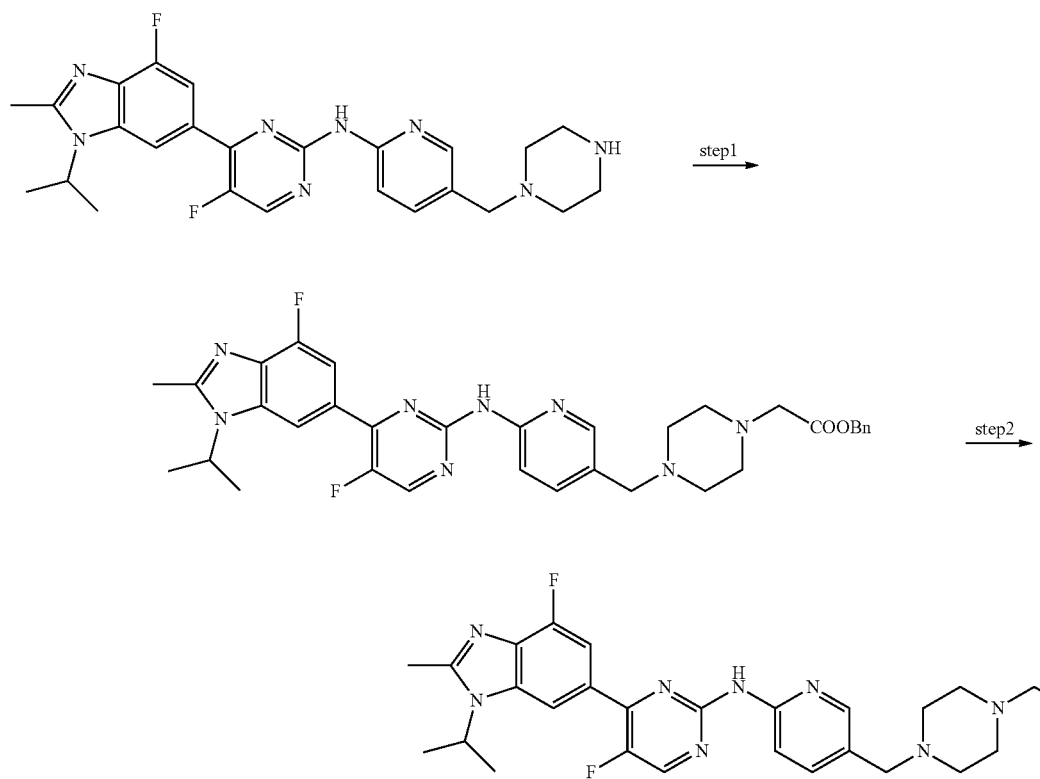

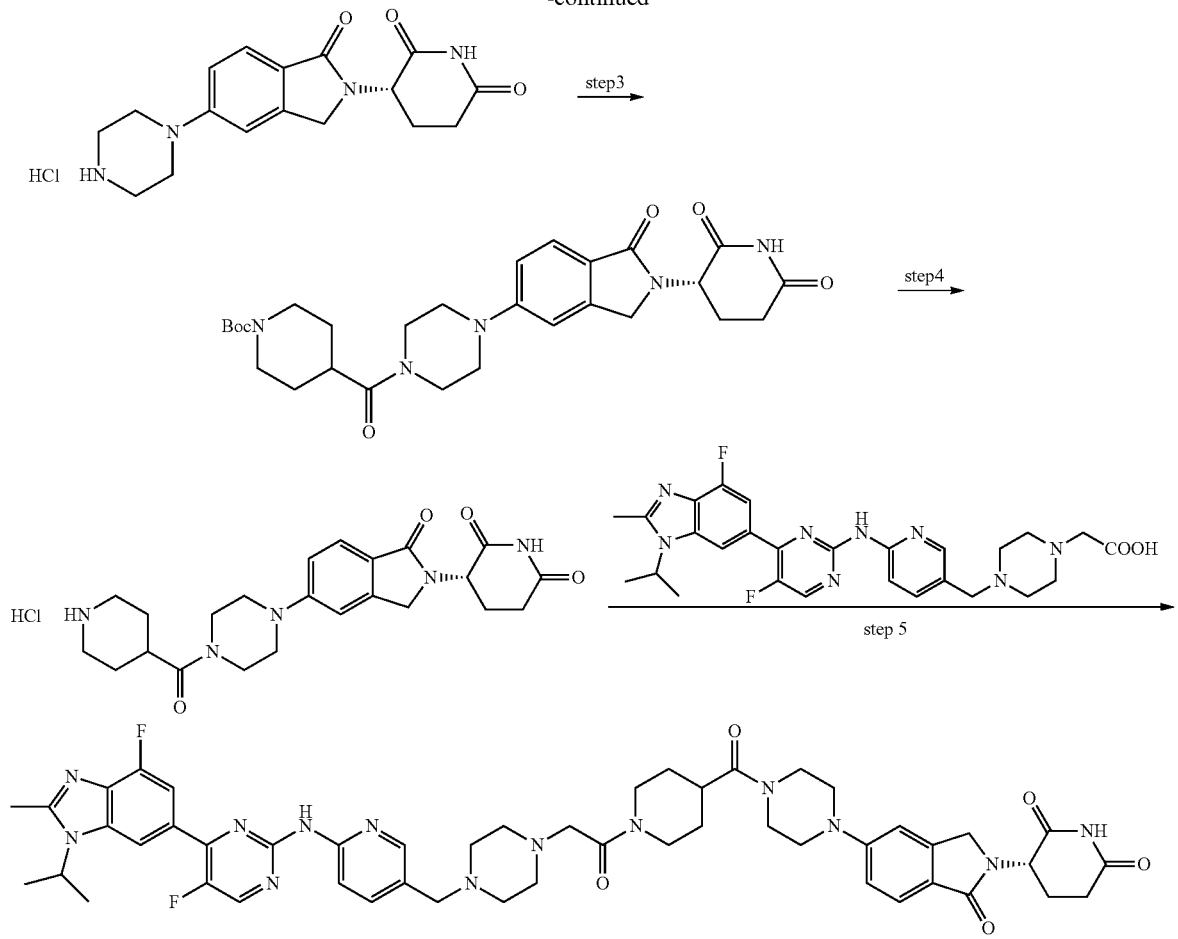

Step 1: Preparation of benzyl 2-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)acetate 5-Fluoro-4-(4-fluoro-1-isopropyl-2-methyl-1H-benzo[d]imidazol-6-yl)-N-(5-(piperazin-1-ylmethyl)pyridin-2-yl)pyrimidin-2-amine (500 mg, 1 mmol) was dissolved in dimethylformamide (10 m), and diisopropylethylamine (388 mg, 3 mmol) and benzyl 2-bromoacetate (458 mg, 2 mmol) were added. After being stirred overnight at 50° C., the reaction solution was diluted with ethyl acetate, washed with water and saturated saline, dried and then purified by column chromatography to yield a product of 100 mg. $[M+H]^+=627.3$.

Step 2: Preparation of 2-(4-((6-(5-fluoro-4-(4-fluoro-1-isopropyl-2-methyl-1H-benzo[d]imidazol-6-yl)pyrimidin-2-yl)amino)pyridin-3-yl)methyl)piperazin-1-yl)acetic acid Benzyl 2-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)acetate (100 mg, 0.16 mmol) was dissolved in methanol (5 mL), and 10% Pd/C (10 mg) was added. After being stirred overnight at room temperature under hydrogen atmosphere, the reaction solution was filtered. Then, the filtrate was dried by a rotary evaporator under reduced pressure to yield a product of 60 mg. $[M+H]^+=537.3$.

Step 3: Preparation of tert-butyl (S)-4-(4-(2-(2,6-dioxopiperidin-3-yl)-1-oxoisoindolin-5-yl)piperazin-1-carbonyl)piperidine-1-carboxylate (S)-3-(1-oxo-5-(piperazin-1-yl)isoindolin-2-yl)piperidine-2,6-dione hydrochloride (1 g, 2.74 mmol) was dissolved in dimethylformamide (10 mL). 1-(Tert-butoxycarbonyl)piperidine-4-carboxylic acid (628 mg, 2.74 mmol), triethylamine (832 mg, 8.22 mmol) and EDCI (1 g, 5.48 mmol) were added. After being stirred overnight at room temperature, the reaction solution was diluted with ethyl acetate, washed with water and saline, dried and then purified by column chromatography to yield a product of 400 mg. $[M+H]^+=540.3$.

Step 4: Preparation of (S)-3-(1-oxo-5-(4-piperidin-4-carbonyl)piperazin-1-yl)isoindolin-2-yl)piperidine-2,6-dione hydrochloride (S)-3-(1-oxo-5-(piperazin-1-yl)isoindol-2-yl)piperidine-2,6-dione hydrochloride (60 mg, 0.11 mmol) was dissolved in ethyl acetate (2 mL), and a 4 M solution of hydrogen chloride in ethyl acetate (2 mL) was added. After being stirred overnight at room temperature, the reaction solution was concentrated and then directly used in the next step. [M+H]⁺=440.2

Step 5: Preparation of (S)-3-(5-(4-(1-(2-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)acetyl)piperidin-4-carbonyl)piperazin-1-yl)-1-oxoisoindolin-2-yl)piperidine-2,6-dione (S)-3-(1-oxo-5-(4-(piperidin-4-carbonyl)piperazin-1-yl)isoindol-2-yl)piperidine-2,6-dione hydrochloride (52 mg, 0.11 mmol) was dissolved in dimethylformamide (5 mL). Triethylamine (33.4 mg, 0.33 mmol), 2-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)acetic acid (60 mg, 0.11 mmol) and HATU (84 mg, 0.22 mmol) were added. After being stirred overnight at room temperature, the reaction solution was diluted with ethyl acetate, washed with water and saline, dried and then purified by column chromatography to yield a product of 9.8 mg. ¹HNMR (400 MHz, CDCl₃) δ 8.45-8.41 (m, 2H), 8.24-8.21 (m, 2H), 7.82-7.73 (m, 3H), 7.01 (d, J=8.8 Hz, 1H), 6.91 (s, 1H), 5.22-5.17 (m, 1H), 4.79-4.72 (m, 1H), 4.58-4.55 (m, 1H), 4.46-4.27 (m, 2H), 4.19-4.15 (m, 1H), 3.81-3.73 (m, 4H), 3.54-3.45 (m, 2H), 3.44-3.28 (m, 5H), 3.19-3.06 (m, 2H), 2.89-2.22 (m, 19H), 1.73 (d, J=6.8 Hz, 6H); [M−H]⁻=956.5.

34) The synthesis route of Compound 7 was illustrated as below:

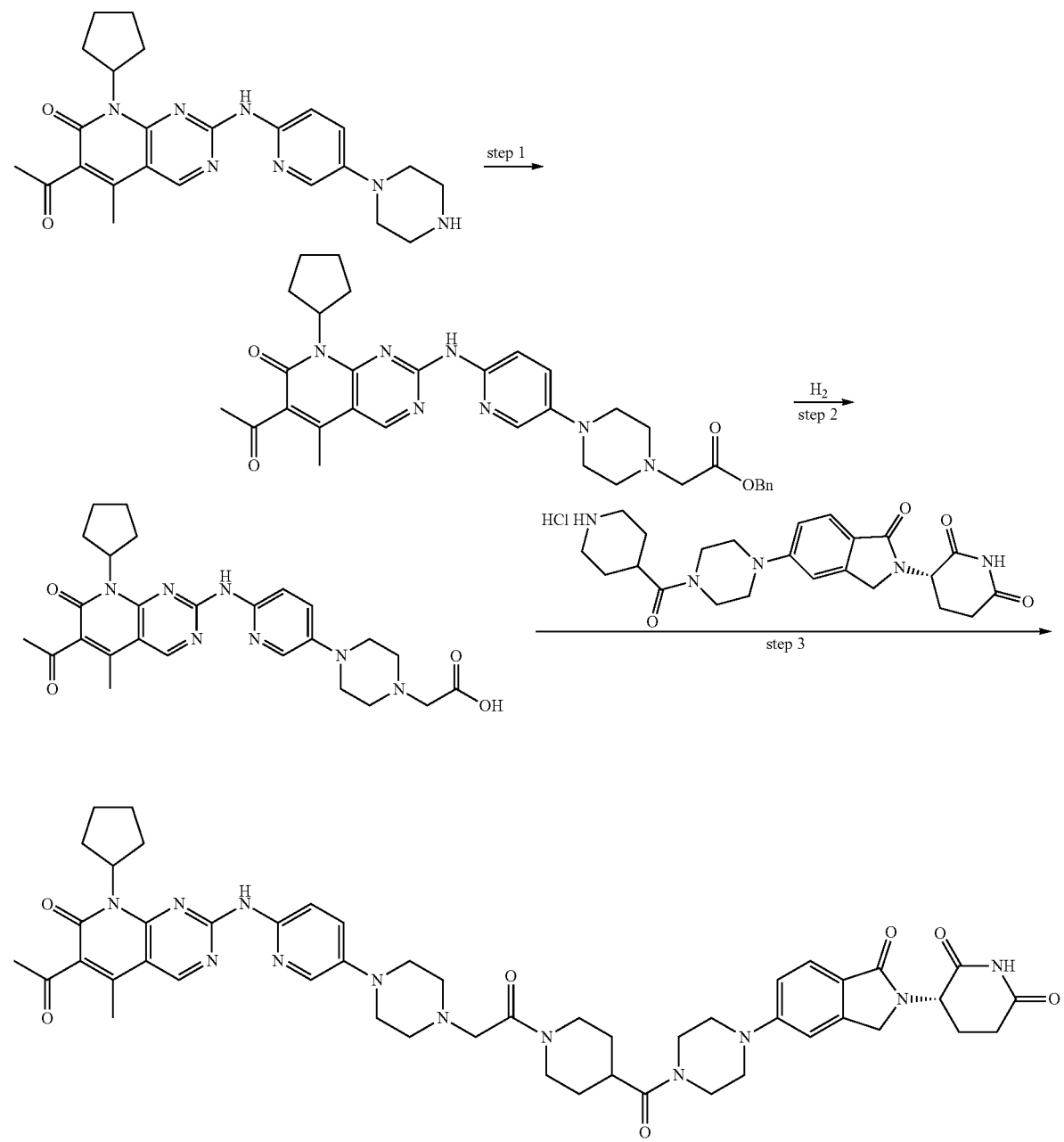

Step 1: Preparation of benzyl 2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetate Palbociclib (500 mg, 1.12 mmol) was dissolved in dimethylformamide (10 mL), and diisopropylethylamine (434 mg, 3.36 mmol) and benzyl 2-bromoacetate (256 mg, 1.12 mmol) were added. After being stirred overnight at 50° C., the reaction solution was diluted with ethyl acetate, washed with water and saline, dried and then purified by column chromatography to yield a product of 400 mg. [M+H]$^+$=596.3.

Step 2: Preparation of 2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetic acid Benzyl 2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetate (100 mg, 0.17 mmol) was dissolved in methanol (10 mL), and 10% Pd/C (10 mg) was added. After being stirred overnight at room temperature under hydrogen atmosphere, the reaction solution was filtered to remove the catalyst. Then, the filtrate was concentrated to yield a product of 85 mg, which would be directly used in the next step. [M+H]$^+$=506.3.

Step 3: Preparation of (S)-3-(5-(4-(1-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetyl)piperidin-4-carbonyl)piperazin-1-yl)-1-oxoisoindolin-2-yl)piperidine-2,6-dione 2-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)acetic acid (85 mg, 0.17 mmol) was dissolved in dimethylformamide (5 mL), and triethylamine (40 mg, 0.4 mmol), (S)-3-(1-oxo-5-(4-(piperidin-4-carbonyl)piperazin-1-yl)isoindolin-2-yl)piperidine-2,6-dione hydrochloride (60 mg, 0.13 mmol) and HATU (65 mg, 0.17 mmol) were added. After being stirred overnight at room temperature, the reaction solution was diluted with ethyl acetate, washed with water and saline, dried and then purified by column chromatography to yield a product of 47 mg. $^1$HNMR (400 MHz, CDCl$_3$) δ 8.82 (s, 1H), 8.16 (brs, 1H), 8.03 (s, 1H), 7.78 (d, J=8.4 Hz, 1H), 7.38-7.35 (m, 1H), 7.03-7.00 (m, 1H), 6.91 (s, 1H), 5.91-5.86 (m, 1H), 5.22-5.18 (m, 1H), 4.63-4.59 (m, 1H), 4.46-4.27 (m, 2H), 4.25-4.21 (m, 1H), 3.81-3.72 (m, 4H), 3.37-3.10 (m, 12H), 2.90-2.73 (m, 9H), 2.56 (s, 3H), 2.38-2.33 (m, 7H), 2.13-1.89 (m, 8H); [M+H]$^+$=927.5.

35) The synthesis route of Compound 8 was illustrated as below:

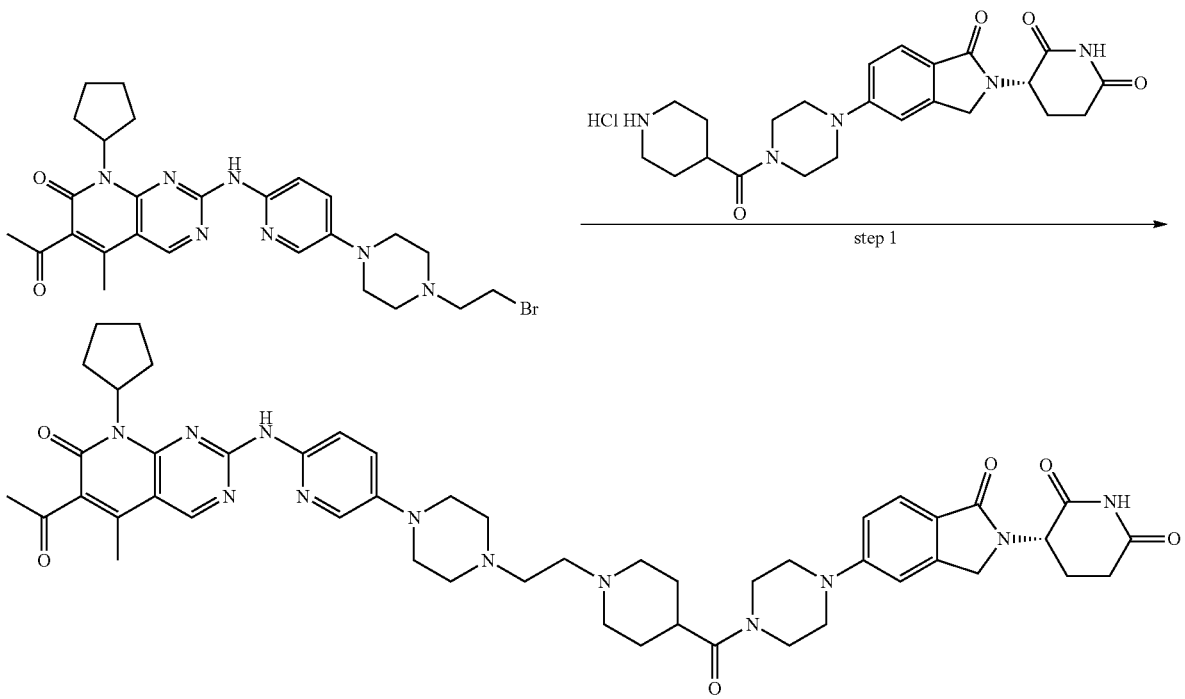

Step 1: Preparation of (S)-3-(5-(4-(1-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperidin-4-carbonyl)piperazin-1-yl)-1-oxo isoindolin-2-yl)piperidine-2,6-dione 6-Acetyl-2-((5-(4-(2-bromoethyl)piperazin-1-yl)pyridin-2-yl)amino)-8-cyclopentyl-5-methylpyrido[2,3-d]pyrimidin-7(8H)-one (20 mg, 0.036 mmol) was dissolved in acetonitrile (5 mL). Diisopropylethylamine (14 mg, 0.11 mmol), potassium iodide (3.3 mg, 0.02 mmol) and (S)-3-(1-oxo-5-(4-(piperidin-4-carbonyl)piperazin-1-yl)isoindolin-2-yl)piperidine-2,6-dione hydrochloride (40 mg, 0.084 mmol) were added. After being stirred overnight at 85° C., the reaction solution was concentrated and then purified by column chromatography to yield a product of 4.9 mg. ¹HNMR (400 MHz, CDCl₃) δ 8.81 (s, 1H), 8.16 (brs, 1H), 8.03 (s, 1H), 7.75 (d, J=8 Hz, 1H), 7.36-7.34 (m, 1H), 7.01-6.99 (m, 1H), 6.90 (s, 1H), 5.90-5.85 (m, 1H), 5.18-5.14 (m, 1H), 4.44-4.26 (m, 2H), 3.78-3.48 (m, 10H), 3.33-3.22 (m, 6H), 3.00-2.83 (m, 8H), 3.55 (s, 3H), 2.37-2.20 (m, 11H), 2.06-1.88 (m, 8H); [M+H]⁺=913.5.
36) The synthesis route of Compound 15 was illustrated as below:
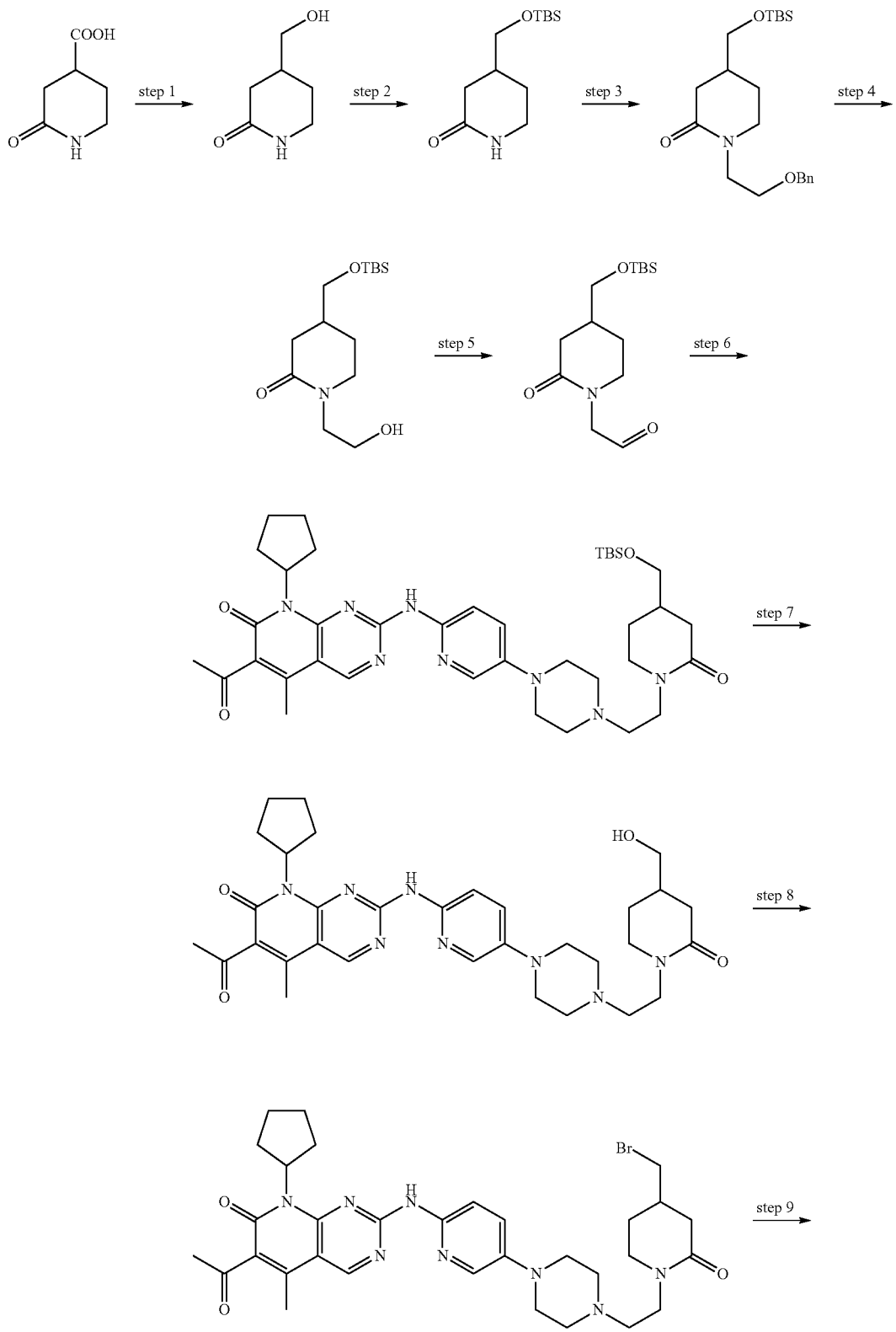

-continued

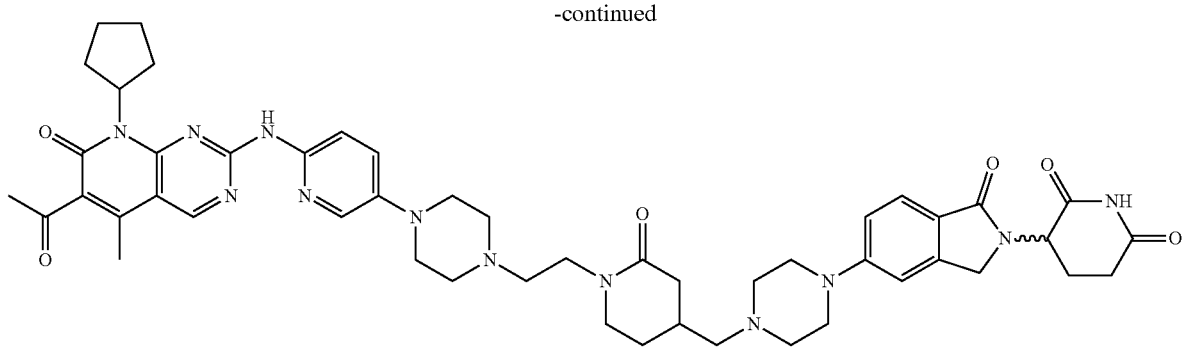

Step 1: Preparation of 4-(hydroxymethyl)piperidin-2-one

2-Oxopiperidine-4-carboxylic acid (15 g, 105 mmol) was dissolved in tetrahydrofuran (500 mL), and N-methylmorpholine (11 g, 110 mmol) was added. The mixture was cooled to −10° C. and then ethyl chloroformate (11.4 g, 105 mmol) was added. While the temperature was kept below 0° C., the mixture was stirred for 45 minutes and then filtered, and the resulting solid was washed with tetrahydrofuran. The filtrate was cooled to below 0° C., and a solution of sodium borohydride in a sodium hydroxide solution (sodium borohydride (6 g, 157 mmol) in a 0.37% sodium hydroxide solution (57.8 g)) was added. The resulting mixture was naturally warmed to room temperature, stirred for one hour and then filtered. The filtrate was concentrated and purified by column chromatography to yield a product of 7.8 g. $[M+H]^+=130.1$.

Step 2: Preparation of 4-(((tert-butyldimethylsilyl)oxy)methyl)piperidin-2-one 4-(Hydroxymethyl)piperidin-2-one (9 g, 70 mmol) was dissolved in dichloromethane (500 mL). Triethylamine (14 g, 140 mmol), tert-butyldimethylsilyl chloride (10.5 g, 70 mmol) and a catalytic amount of dimethylaminopyridine were added. The mixture was reacted overnight at room temperature, concentrated and then purified by column chromatography to yield a product of 13.9 g. $[M+H]^+=244.2$.

Step 3: Preparation of 1-(2-(benzyloxy)ethyl)-4-(((tert-butyldimethylsilyl)oxy)methyl)piperidin-2-one 4-(((Tert-butyldimethylsilyl)oxy)methyl)piperidin-2-one (8 g, 33 mmol) was dissolved in tetrahydrofuran (500 mL). ((2-Bromoethoxy)methyl)benzene (7.1 g, 33 mmol), potassium hydroxide (5.54 g, 99 mmol) and a catalytic amount of tetrabutylammonium iodide were added. The mixture was heated to 60° C. and reacted overnight, concentrated and then purified by column chromatography to yield a product of 6.1 g. $[M+H]^+=378.2$.

Step 4: Preparation of 4-(((tert-butyldimethylsilyl)oxy)methyl)-1-(2-hydroxyethyl)piperidin-2-one 1-(2-(Benzyloxy)ethyl)-4-(((tert-butyldimethylsilyl)oxy)methyl)piperidin-2-one (6 g, 16 mmol) was dissolved in methanol (200 mL), and palladium on carbon was added. The mixture was reacted overnight at room temperature under hydrogen atmosphere, filtered and concentrated to yield a product of 4.2 g. $[M+H]^+=288.2$.

Step 5: Preparation of 2-(4-(((tert-butyldimethylsilyl)oxy)methyl)-2-oxopiperidin-1-yl)acetaldehyde 4-(((Tert-butyldimethylsilyl)oxy)methyl)-1-(2-hydroxyethyl)piperidin-2-one (583 mg, 2 mmol) was dissolved in dichloromethane (20 mL), and DessMartin reagent (2.54 g, 6 mmol) was added. The mixture was reacted at room temperature for 2 hours and filtered. After that, the filtrate was washed with a sodium bicarbonate solution and a sodium thiosulfate solution, dried and concentrated to yield a crude product of 600 mg, which was directly used in the next step. $[M+H]^+=286.2$.

Step 6: Preparation of 6-acetyl-2-((5-(4-(2-(4-(((tert-butyldimethylsilyl)oxy)methyl)-2-oxopiperidin-1-yl)ethyl)piperazin-1-yl)pyridin-2-yl)amino)-8-cyclopentyl-5-methylpyrido[2,3-d]pyrimidin-7(8H)-one 2-(4-(((Tert-butyldimethylsilyl)oxy)methyl)-2-oxopiperidin-1-yl)acetaldehyde (crude product, 600 mg) was dissolved in 1,2-dichloroethane (50 mL), and Palbociclib (895 mg, 2 mmol) and a catalytic amount of acetic acid were added. The mixture was reacted at room temperature for half an hour, and then sodium triacetoxyborohydride (2.1 g, 10 mmol) was added. The resulting mixture was reacted overnight at room temperature, concentrated and then purified by a preparative TLC plate to yield a product of 340 mg. $[M+H]^+=717.4$.

Step 7: Preparation of 6-acetyl-2-((5-(4-(2-(4-hydroxymethyl-2-oxopiperidin-1-yl)ethyl)piperazin-1-yl)pyridin-2-yl)amino)-8-cyclopentyl-5-methylpyrido[2,3-d]pyrimidin-7(8H)-one 6-Acetyl-2-((5-(4-(2-(4-(((tert-butyldimethylsilyl)oxy)methyl)-2-oxopiperidin-1-yl)ethyl)piperazin-1-yl)pyridin-2-yl)amino)-8-cyclopentyl-5-methylpyrido[2,3-d]pyrimidin-7(8H)-one (240 mg, 0.34 mmol) was dissolved in tetrahydrofuran (20 mL), and a solution of tetrabutylammonium fluoride in tetrahydrofuran (1 M, 1 mL) was added. The mixture was reacted overnight at room temperature, concentrated, washed with water, washed with a sodium bicarbonate solution, and purified by a preparative TLC plate to yield a product of 120 mg. $[M+H]^+=603.3$.

Step 8: Preparation of 6-acetyl-2-((5-(4-(2-(4-bromomethyl-2-oxopiperidin-1-yl)ethyl)piperazin-1-yl)pyridin-2-yl)amino)-8-cyclopentyl-5-methylpyrido[2,3-d]pyrimidin-7(8H)-one 6-Acetyl-2-((5-(4-(2-(4-hydroxymethyl-2-oxopiperidin-1-yl)ethyl)piperazin-1-yl)pyridin-2-yl)amino)-8-cyclopentyl-5-methylpyrido[2,3-d]pyrimidin-7(8H)-one (100 mg, 0.17 mmol) was dissolved in acetonitrile (10 mL), and phosphorus tribromide (92 mg, 0.34 mmol) was added. The mixture was heated to 70° C., reacted overnight, and poured into water. A sodium bicarbonate solution was added thereto, and the resulting mixture was extracted with dichloromethane and methanol (dichloromethane:methanol=10:1) and purified by a preparative TLC plate to yield a product of 6 mg. [M+H]⁺=665.3.

Step 9: Preparation of 3-(5-(4-((1-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)-2-oxopiperidin-4-yl)methyl)piperazin-1-yl)-1-oxoisoindolin-2-yl)piperidine-2,6-dione 6-Acetyl-2-((5-(4-(2-(4-bromomethyl-2-oxopiperidin-1-yl)ethyl)piperazin-1-yl)pyridin-2-yl)amino)-8-cyclopentyl-5-methylpyrido[2,3-d]pyrimidin-7(8H)-one (6 mg, 0.009 mmol) was dissolved in acetonitrile (10 mL). 3-(1-Oxo-5-(piperazin-1-yl)isoindolin-2-yl)piperidine-2,6-dione hydrochloride (6.6 mg, 0.018 mmol), diisopropylethylamine (11.6 mg, 0.09 mmol) and a catalytic amount of potassium iodide were added. The mixture was heated to 80° C. and reacted overnight, filtered, concentrated and then purified by a preparative TLC plate to yield a product of 2.6 mg. ¹HNMR (400 MHz, CDCl₃) δ 8.83 (s, 1H), 8.35 (s, 1H), 8.28 (brs, 1H), 8.04 (d, J=2.4 Hz, 1H), 1.75 (d, J=8.8 Hz, 1H), 7.39-7.36 (m, 1H), 7.03-7.00 (m, 1H), 6.90 (s, 1H), 5.91-5.84 (m, 1H), 5.25-5.21 (m, 1H), 4.46-4.26 (m, 2H), 3.78-3.58 (m, 4H), 3.45-3.42 (m, 2H), 3.34-3.32 (m, 4H), 3.23 (s, 4H), 3.15-3.10 (m, 1H), 2.97-2.81 (m, 2H), 2.74 (s, 4H), 2.66-2.58 (m, 9H), 2.40-2.31 (m, 8H), 2.27-2.20 (m, 2H), 2.12-2.03 (m, 6H). [M+H]⁺=913.5.

W was methylene, m was equal to 2; the ring consisting of $X_1$ to $X_6$ and the ring consisting of $Z_1$ to $Z_6$ were piperidine rings; Y was oxygen or methylene; and R was absent or halogen.

9

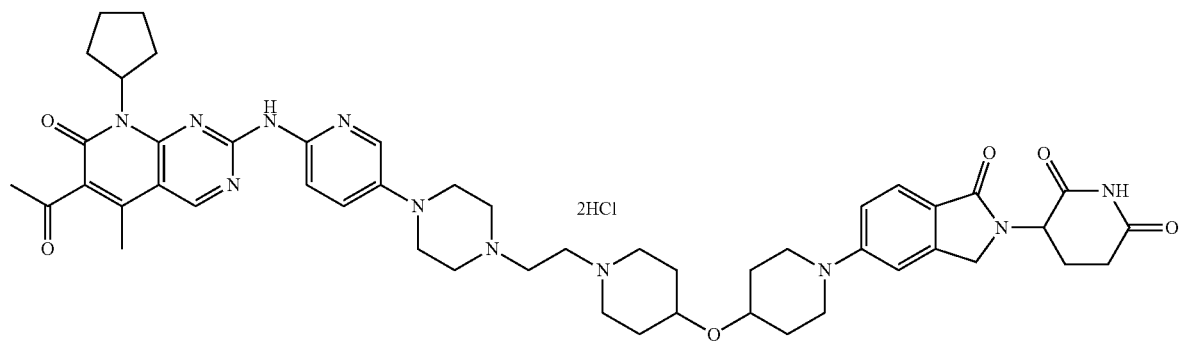

10

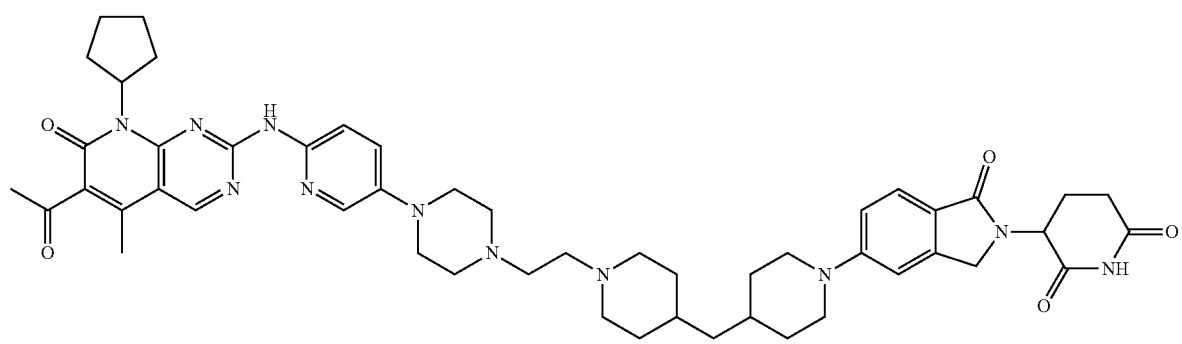

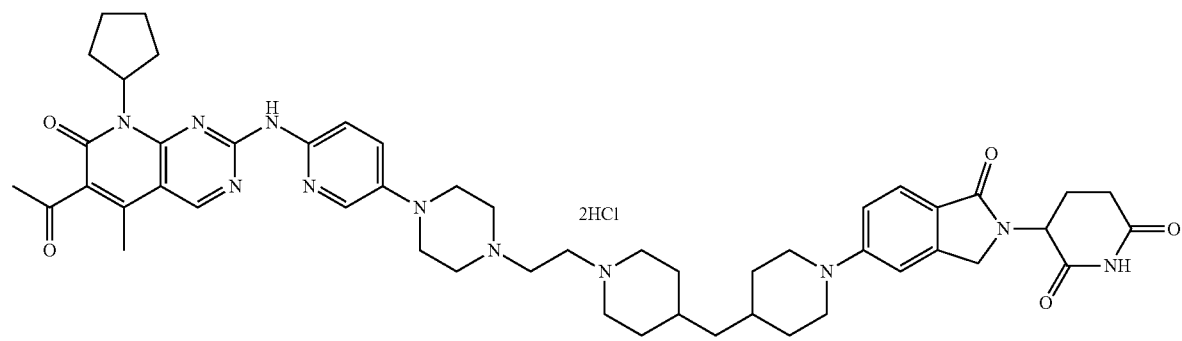
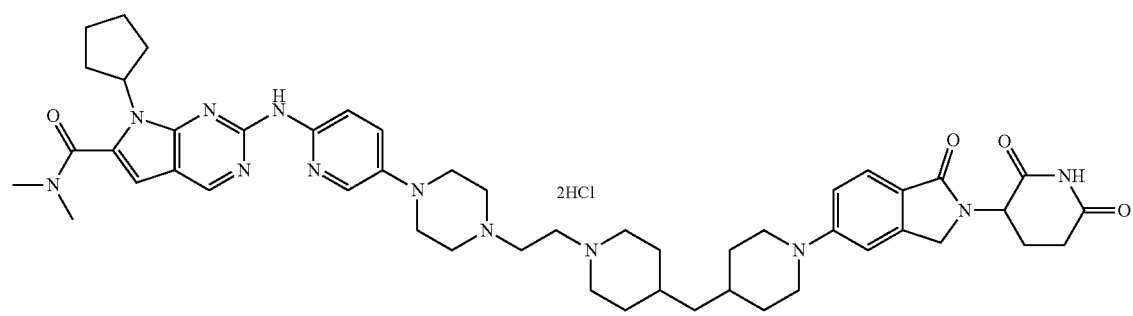
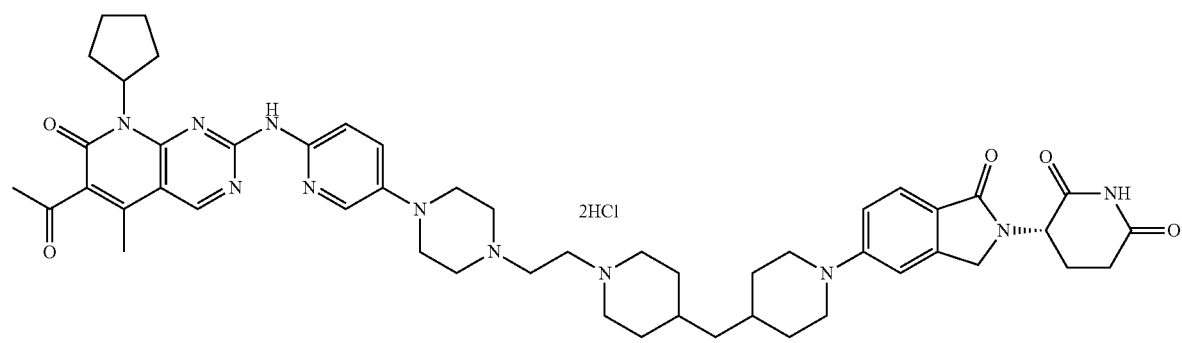
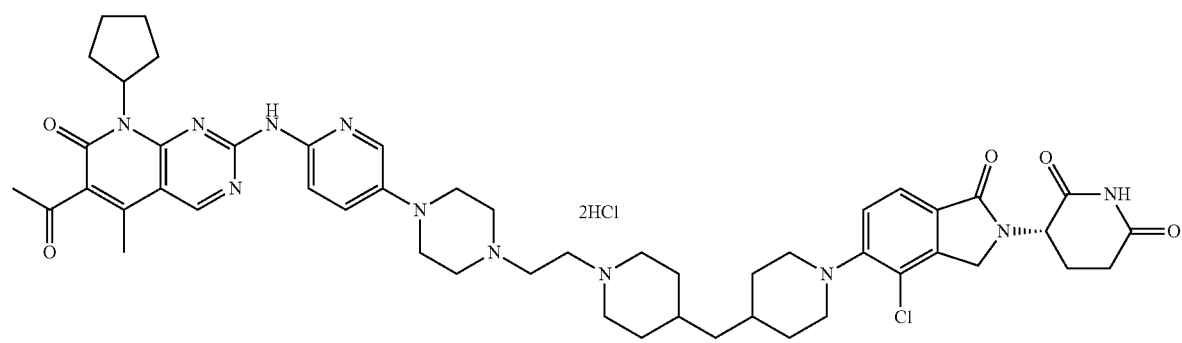

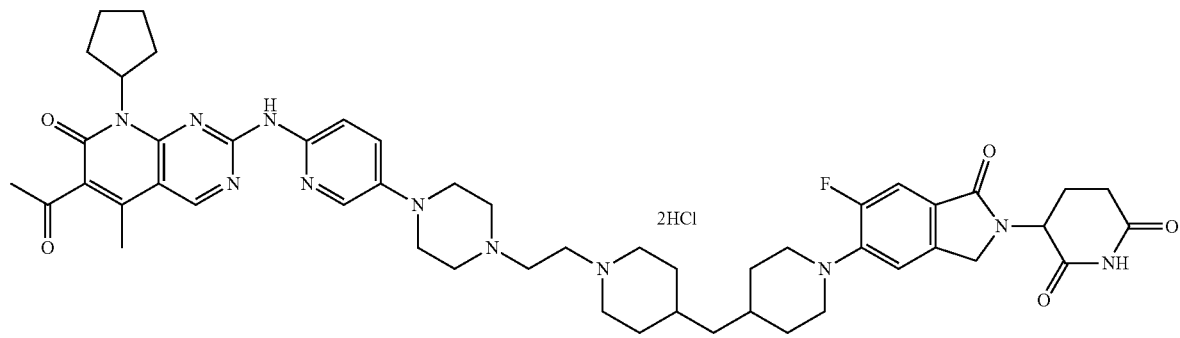 [SMILES: CC(=O)c1c(C)c2cnc(Nc3ccc(N4CCN(CCN5CCC(CC6CCN(c7cc8c(cc7F)C(=O)N(C7CCC(=O)NC7=O)C8)CC6)CC5)CC4)cn3)nc2n(C2CCCC2)c1=O]
37
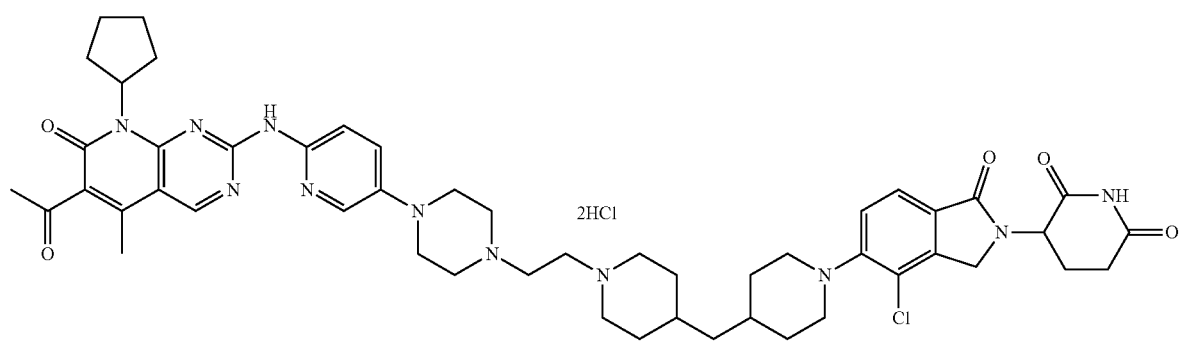
39
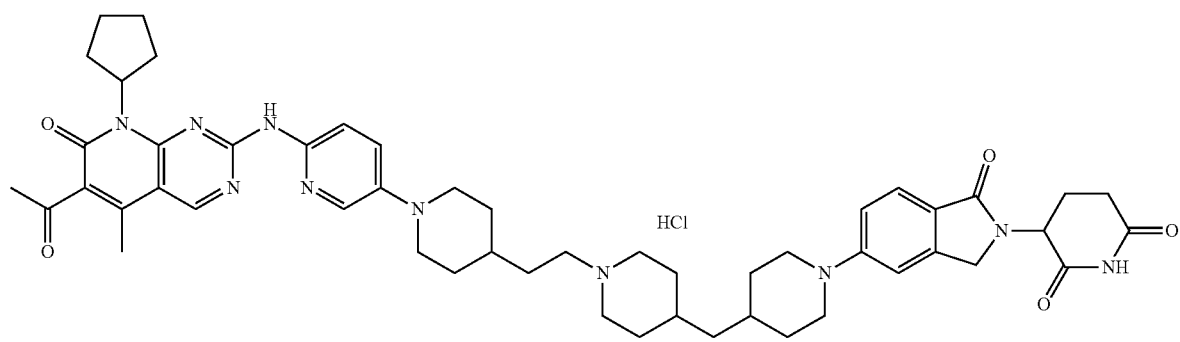
42
37) The synthesis route of Compound 9 was illustrated as below:
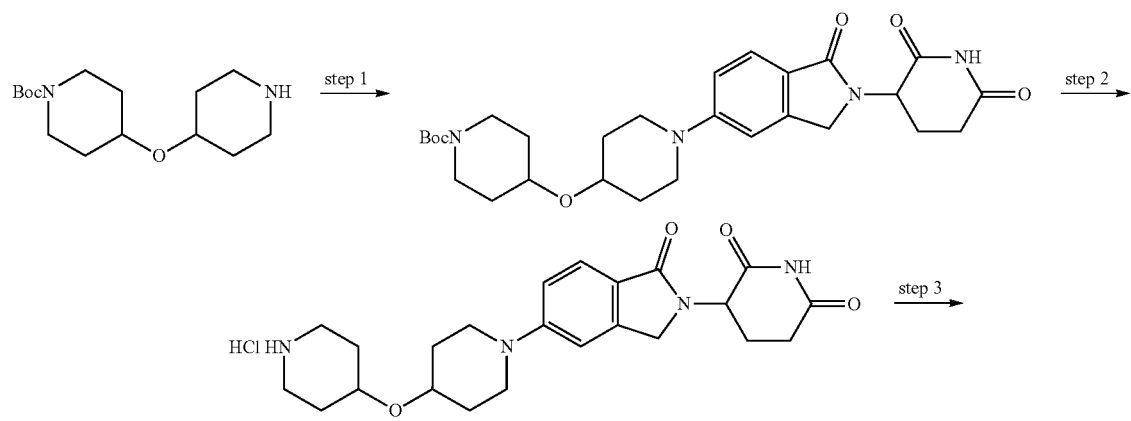

-continued

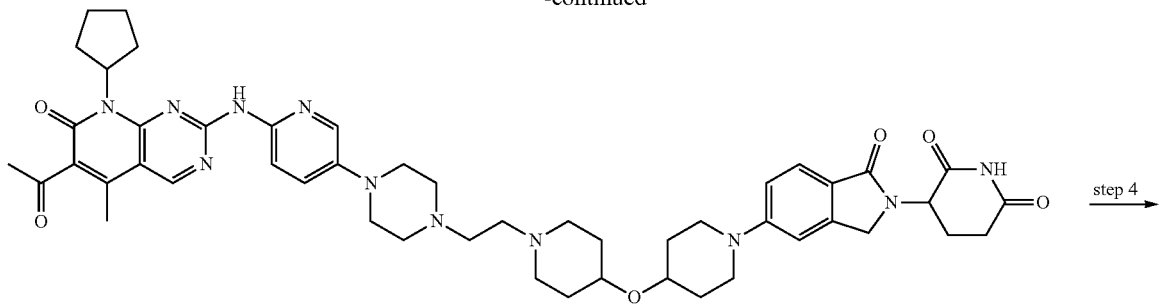

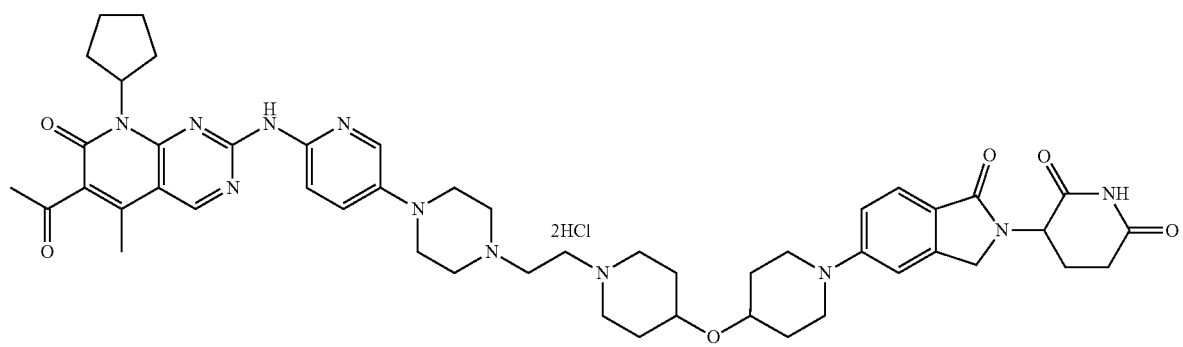

Step 1: Preparation of tert-butyl 4-((1-(2-(2,6-di-oxopiperidin-3-yl)-1-oxoisoindolin-5-yl)piperidin-4-yl)oxy)piperidine-1-carboxylate Tert-butyl 4-((piperidin-4-yl)oxy)piperidine-1-carboxylate (200 mg, 0.7 mmol) was dissolved in dioxane (10 mL). 3-(5-Bromo-1-oxoisoindolin-2-yl)piperidine-2,6-dione (226 mg, 0.7 mmol), X-phos (100 mg, 0.21 mmol), cesium carbonate (456 mg, 1.4 mmol) and palladium acetate (31.4 mg, 0.14 mmol) were added. The mixture was heated to 100° C. and reacted overnight under nitrogen protection. The reaction solution was concentrated and then purified by column chromatography to yield a product of 26 mg. [M+H]$^+$=527.3.

Step 2: Preparation of 3-(1-oxo-5-(4-(piperidin-4-yloxy)piperidin-1-yl)isoindolin-2-yl)piperidine-2,6-dione hydrochloride Tert-butyl 4-((1-(2-(2,6-dioxopiperidin-3-yl)-1-oxoisoindolin-5-yl)piperidin-4-yl)oxy)piperidine-1-carboxylate (26 mg, 0.05 mmol) was dissolved in ethyl acetate (2 mL), and a solution of hydrogen chloride in ethyl acetate (5 mL) was added. The mixture was reacted at room temperature for 2 hours and dried by a rotary evaporator to yield a crude product of 20 mg, which was directly used in the next step. [M+H]$^+$=427.3.

Step 3: Preparation of 3-(5-(4-((1-(2-(4-(6-((6-acetyl-8-cyclopentyl-5-methyl-7-oxo-7,8-dihydro-pyrido[2,3-d]pyrimidin-2-yl)amino)pyridin-3-yl)piperazin-1-yl)ethyl)piperidin-4-yl)oxy)piperidin-1-yl)-1-oxoisoindolin-2-yl)piperidine-2,6-dione 3-(1-Oxo-5-(4-(piperidin-4-yloxy)piperidin-1-yl)isoindolin-2-yl)piperidine-2,6-dione hydrochloride (20 mg, 0.043 mmol) was dissolved in acetonitrile (5 mL). 6-Acetyl-2-((5-(4-(2-bromoethyl)piperazin-1-yl)pyridin-2-yl)amino)-8-cyclopentyl-5-methylpyrido[2,3-d]pyrimidin-7(8H)-one (23.8 mg, 0.043 mmol), diisopropylethylamine (16.8 mg, 0.13 mmol) and a catalytic amount of potassium iodide were added. After being heated to 85° C. and reacted overnight, the reaction solution was concentrated and then purified by a preparative TLC plate to yield a product of 11 mg. [M+H]$^+$=900.5.

Step 4: Preparation of 3-(5-(4-((1-(2-(4-(6-((6-acetyl-8-cyclopentyl-5-methyl-7-oxo-7,8-dihydro-pyrido[2,3-d]pyrimidin-2-yl)amino)pyridin-3-yl)piperazin-1-yl)ethyl)piperidin-4-yl)oxy)piperidin-1-yl)-1-oxoisoindolin-2-yl)piperidine-2,6-dione dihydrochloride 3-(5-(4-((1-(2-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)ethyl)piperidin-4-yl)oxy)piperidin-1-yl)-1-oxoisoindolin-2-yl)piperidine-2,6-dione (9 mg, 0.01 mmol) was dissolved in methanol (2 mL), and a solution of hydrogen chloride in methanol (5 mL) was added. The mixture was reacted overnight at room temperature and concentrated to yield a product of 9 mg. $^1$HNMR (400 MHz, CDCl$_3$) δ 10.95 (s, 1H), 9.03 (s, 1H), 8.13 (s, 1H), 7.90-7.86 (m, 2H), 7.55 (d, J=8.4 Hz, 1H), 7.15-7.12 (m, 2H), 5.88-5.84 (m, 1H), 5.08-5.04 (m, 1H), 4.37-4.20 (m, 2H), 4.02-3.69 (m, 12H), 3.31-3.07 (m, 12H), 2.96-2.87 (m, 1H), 2.63-2.57 (m, 1H), 2.45 (m, 3H), 2.36 (m, 3H), 2.30-2.20 (m, 2H), 2.04-1.92 (m, 7H), 1.86-1.78 (m, 3H), 1.63-1.56 (m, 4H). [M+H]$^+$=900.5.

38) The synthesis route of Compound 10 was illustrated as below:

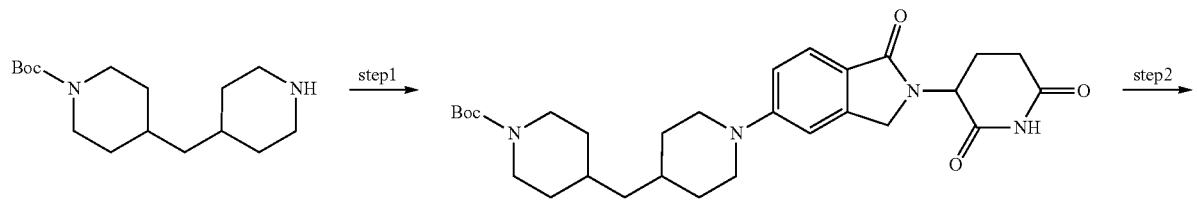

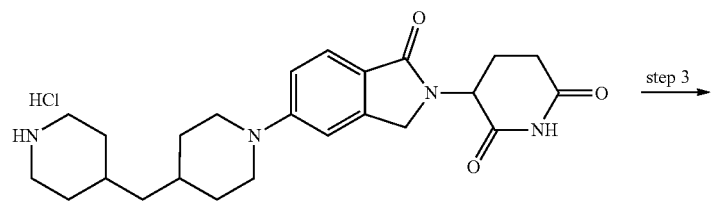

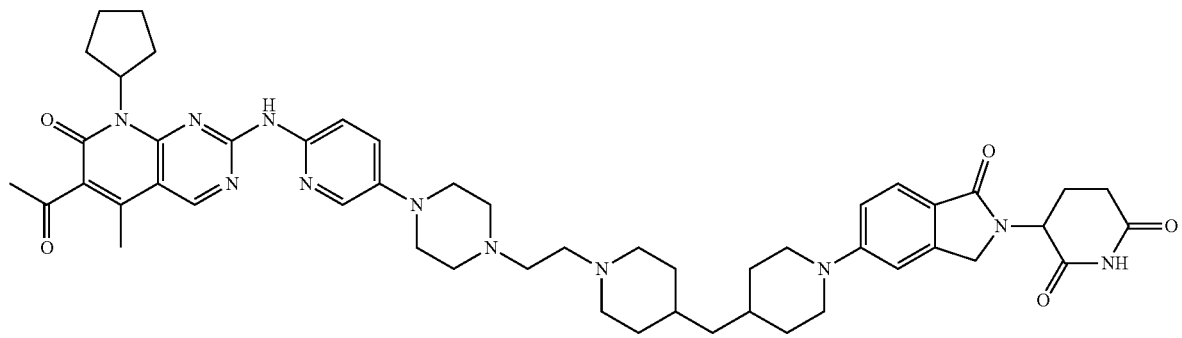

Step 1: Preparation of tert-butyl 4-((1-(2-(2,6-dioxopiperidin-3-yl)-1-oxoisoindolin-5-yl)piperidin-4-yl)methyl)piperidine-1-carboxylate Tert-butyl 4-(piperidin-4-ylmethyl)piperidine-1-carboxylate (100 mg, 0.35 mmol) was dissolved in 1,4-dioxane (10 mL). 3-(5-Bromo-1-oxoisoindolin-2-yl)piperidine-2,6-dione (113 mg, 0.35 mmol), X-phos (66.7 mg, 0.14 mmol), palladium acetate (15.7 mg, 0.07 mmol) and cesium carbonate (228 mg, 0.7 mmol) were added. The mixture was heated to 100° C. and reacted overnight under nitrogen atmosphere, filtered, concentrated, and then purified by column chromatography to yield a product of 50 mg. $[M+H]^+=525.3$.

Step 2: Preparation of 3-(1-oxo-5-(4-(piperidin-4-ylmethyl)piperidin-1-yl)isoindolin-2-yl)piperidine-2,6-dione hydrochloride Tert-butyl 4-((1-(2-(2,6-dioxopiperidin-3-yl)-1-oxoisoindolin-5-yl)piperidin-4-yl)methyl)piperidine-1-carboxylate (50 mg, 0.095 mmol) was dissolved in ethyl acetate (5 mL), and a solution of hydrogen chloride in ethyl acetate (20 mL) was added. The mixture was reacted overnight at room temperature and concentrated to yield a crude product of 40 mg. $[M+H]^+=425.3$.

Step 3: Preparation of 3-(5-(4-((1-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperidin-4-yl)methyl)piperidin-1-yl)-1-oxoisoindolin-2-yl)piperidine-2,6-dione 3-(1-Oxo-5-(4-(piperidin-4-ylmethyl)piperidin-1-yl)isoindolin-2-yl)piperidine-2,6-dione hydrochloride (crude product, 40 mg) was dissolved in acetonitrile (20 mL). 6-Acetyl-2-((5-(4-(2-bromoethyl)piperazin-1-yl)pyridin-2-yl)amino)-8-cyclopentyl-5-methylpyrido[2,3-d]pyrimidin-7(8H)-one (111 mg, 0.2 mmol), diisopropylethylamine (64.6 mg, 0.5 mmol) and a catalytic amount of potassium iodide were added. The mixture was heated to 80° C. and reacted overnight, concentrated and then purified by column chromatography to yield a product of 30 mg. $^1$HNMR (400 MHz, $d_6$-DMSO) δ 10.96 (s, 1H), 10.14 (brs, 1H), 8.97 (s, 1H), 8.07 (d, J=0.4 Hz, 1H), 7.88-7.86 (m, 1H), 7.51-7.49 (m, 2H), 7.05-7.03 (m, 2H), 5.86-5.82 (m, 1H), 5.08-5.03 (m, 1H), 4.35-4.18 (m, 2H), 3.89-3.86 (m, 2H), 3.18-3.16 (m, 4H), 2.96-2.78 (m, 5H), 2.68-2.58 (m, 4H), 2.43 (s, 3H), 2.39-2.35 (m, 2H), 2.32 (s, 3H), 2.28-2.21 (m, 3H), 2.02-1.88 (m, 4H), 1.80-1.59 (m, 10H), 1.24-1.07 (m, 10H). $[M+H]^+=898.5$.

39) The synthesis route of Compound 11 was illustrated as below:

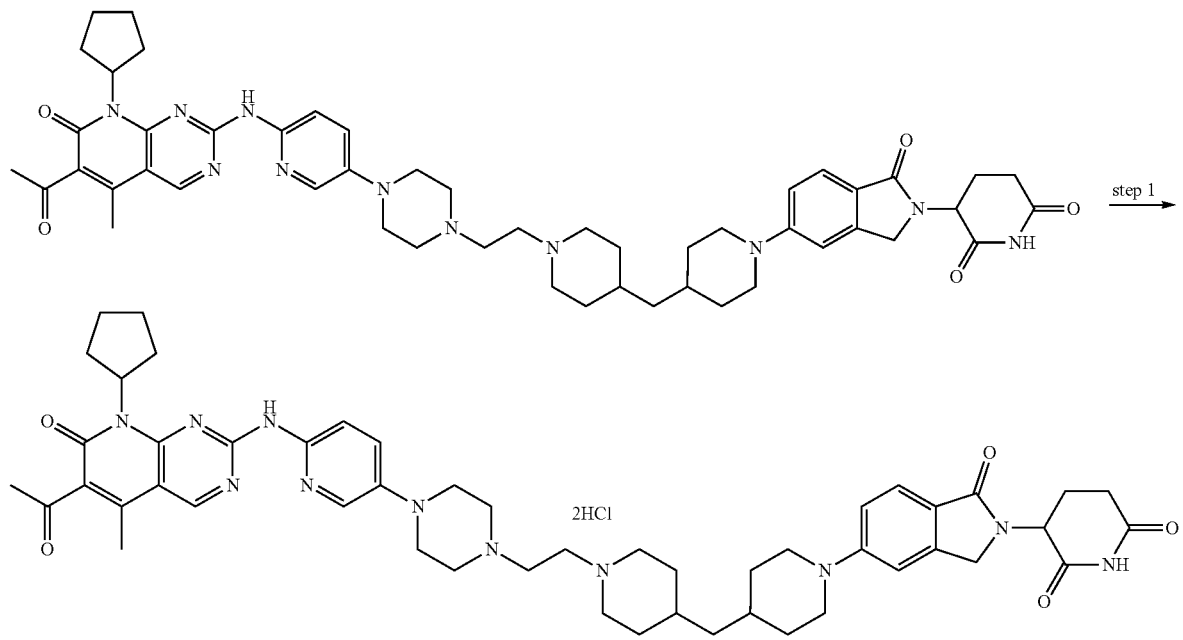

Step 1: Preparation of 3-(5-(4-((1-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperidin-4-yl)methyl)piperidin-1-yl)-1-oxoisoindolin-2-yl)piperidine-2,6-dione dihydrochloride 3-(5-(4-((1-(2-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)ethyl)piperidin-4-yl)methyl)piperidin-1-yl)-1-oxoisoindolin-2-yl)piperidine-2,6-dione (12 mg, 0.013 mmol) was dissolved in methanol (5 mL), and a solution of hydrogen chloride in methanol (20 mL) was added. The mixture was reacted overnight at room temperature, concentrated and then purified by a preparative TLC plate to yield a product of 8 mg. $^1$HNMR (400 MHz, d$_6$-DMSO) δ 11.40 (brs, 2H), 11.00 (s, 1H), 10.61 (brs, 1H), 9.06 (s, 1H), 8.14-8.09 (m, 2H), 7.88 (d, J=9.2 Hz, 1H), 7.65 (brs, 1H), 7.41 (brs, 2H), 5.91-5.82 (m, 1H), 5.11-5.07 (m, 1H), 4.43-4.25 (m, 2H), 3.99-3.58 (m, 16H), 3.30 (brs, 6H), 3.07-2.88 (m, 4H), 2.63-2.58 (m, 1H), 2.46-2.37 (m, 8H), 2.27-2.22 (m, 3H), 2.00-1.81 (m, 12H), [M+H]$^+$=898.5.

40) The synthesis route of Compound 35 was illustrated as below:

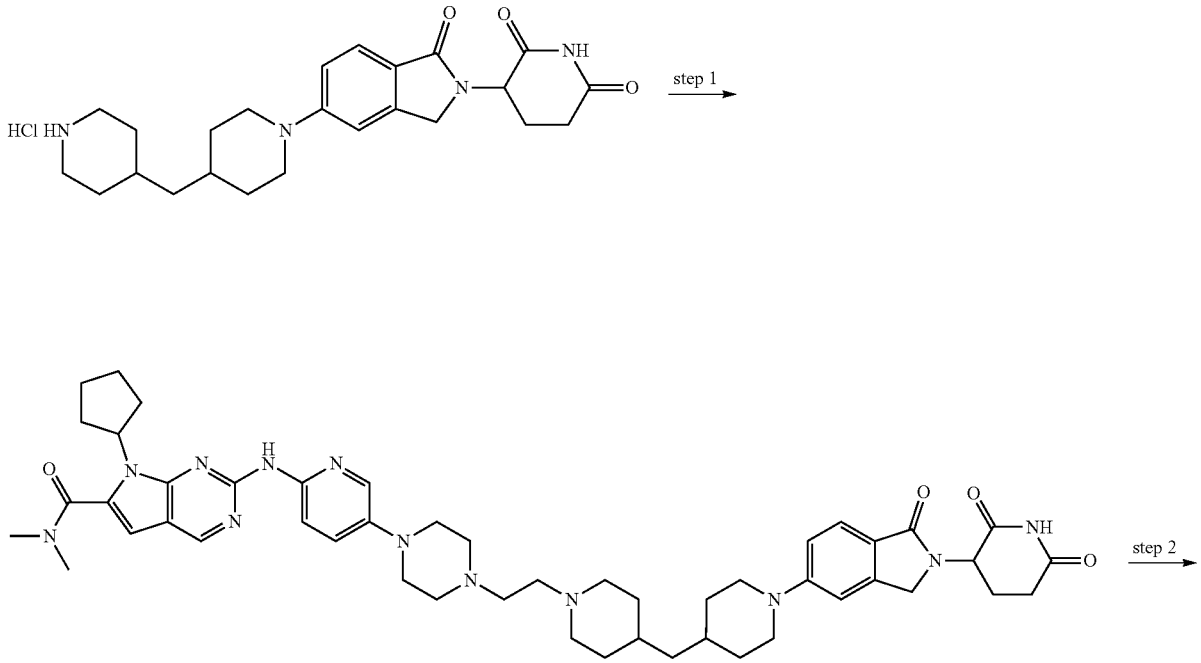

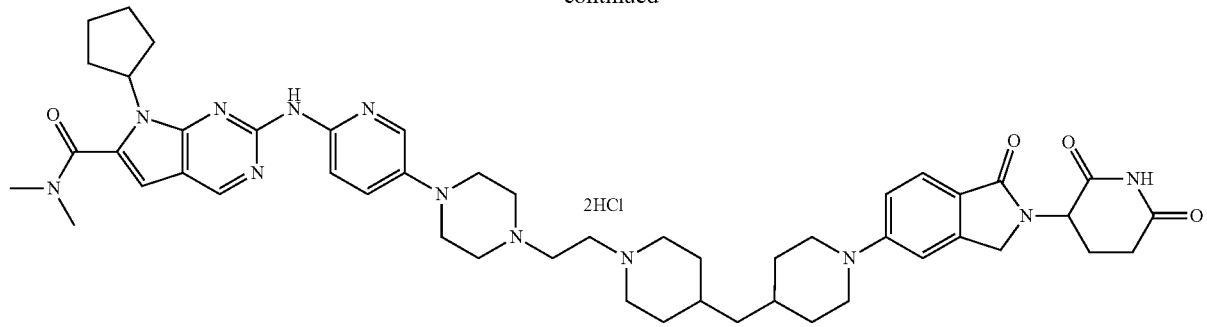

Step 1: Preparation of 7-cyclopentyl-2-((5-(4-(2-(4-((1-(2-(2,6-dioxopiperidin-3-yl)-1-oxoisoindolin-5-yl)piperidin-4-yl)methyl)piperidin-1-yl)ethyl)piperazin-1-yl)pyridin-2-yl)amino)-N,N-dimethyl-7H-pyrrolo[2,3-d]pyrimidin-6-amide 3-(1-Oxo-5-(4-(piperidin-4-ylmethyl)piperidin-1-yl) isoindolin-2-yl)piperidine-2,6-dione hydrochloride (125 mg, 0.27 mmol) was dissolved in acetonitrile (10 mL). 2-((5-(4-(2-Bromoethyl)piperazin-1-yl)pyridin-2-yl) amino)-7-cyclopentyl-N,N-dimethyl-7H-pyrrolo[2,3-d]pyrimidin-6-amide (146.2 mg, 0.27 mmol), diisopropylethylamine (129 mg, 1 mmol) and a catalytic amount of potassium iodide were added. The mixture was heated to 80° C. and reacted overnight, concentrated and then purified to yield a product of 10 mg. [M+H]⁺=885.5.

Step 2: Preparation of 7-cyclopentyl-2-((5-(4-(2-(4-((1-(2-(2,6-dioxopiperidin-3-yl)-1-oxoisoindolin-5-yl)piperidin-4-yl)methyl)piperidin-1-yl)ethyl)piperazin-1-yl)pyridin-2-yl)amino)-N,N-dimethyl-7H-pyrrolo[2,3-d]pyrimidin-6-amide dihydrochloride 7-Cyclopentyl-2-((5-(4-(2-(4-((1-(2-(2,6-dioxopiperidin-3-yl)-1-oxoisoindolin-5-yl)piperidin-4-yl)methyl)piperidin-1-yl)ethyl)piperazin-1-yl)pyridin-2-yl)amino)-N,N-dimethyl-7H-pyrrolo[2,3-d]pyrimidin-6-amide (10 mg, 0.011 mmol) was dissolved in methanol (2 mL), and a solution of hydrogen chloride in methanol (10 mL) was added. The mixture was reacted overnight at room temperature and concentrated to yield a product of 10 mg. ¹HNMR (400 MHz, d₆-DMSO) δ 11.65 (s, 1H), 11.38 (brs, 1H), 10.97 (s, 1H), 10.58 (brs, 1H), 9.05 (s, 1H), 8.16-8.13 (m, 1H), 8.04 (s, 1H), 7.79-7.76 (m, 2H), 7.65-7.59 (m, 2H), 6.87 (s, 1H), 5.10-5.05 (m, 1H), 4.87-4.78 (m, 1H), 4.40-4.23 (m, 2H), 3.95-3.82 (m, 11H), 3.29 (brs, 5H), 3.07-2.89 (m, 10H), 2.63-2.58 (m, 1H), 2.41-2.25 (m, 3H), 2.09-1.90 (m, 10H), 1.82-1.77 (m, 2H), 1.69-1.66 (m, 4H), 1.47-1.45 (m, 2H), 1.40-1.29 (m, 2H). [M+H]⁺=885.5.

41) The synthesis route of Compound 38 was illustrated as below:

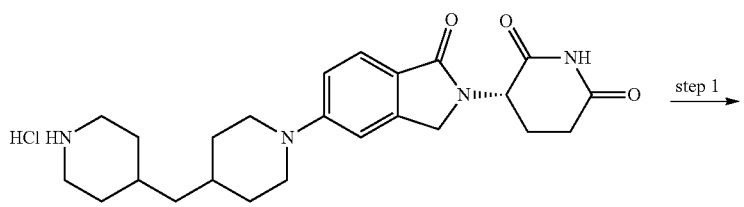

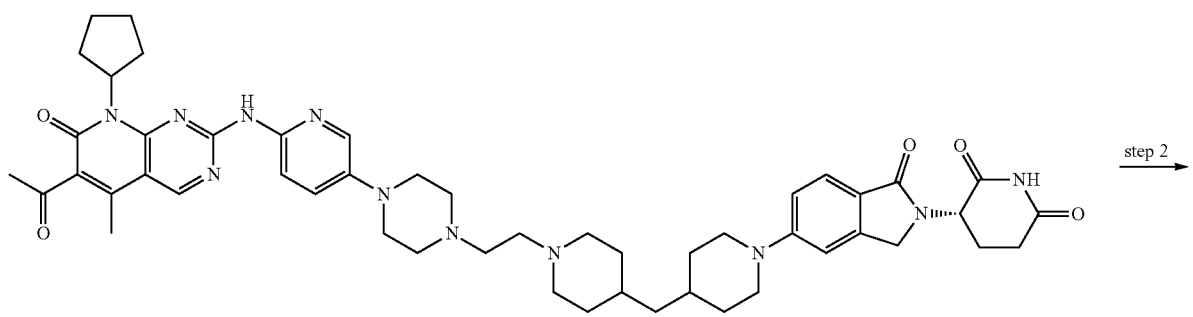

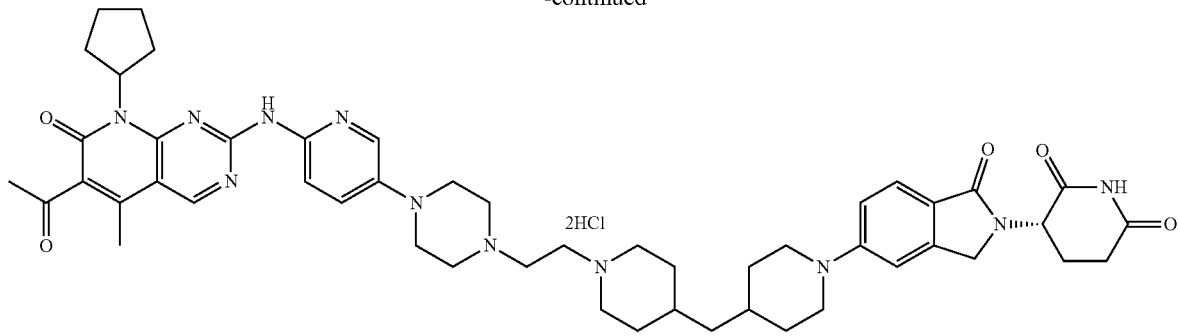

Step 1: Preparation of (S)-3-(5-(4-((1-(2-(4-(6-((6-acetyl-8-cyclopentyl-5-methyl-7-oxo-7,8-dihydro-pyrido[2,3-d]pyrimidin-2-yl)amino)pyridin-3-yl)piperazin-1-yl)ethyl)piperidin-4-yl)methyl)piperidin-1-yl)-1-oxoisoindolin-2-yl)piperidine-2,6-dione (S)-3-(1-oxo-5-(4-(piperidin-4-ylmethyl)piperidin-1-yl)isoindolin-2-yl)piperidine-2,6-dione hydrochloride (150 mg, 0.33 mmol) was dissolved in acetonitrile (20 mL). 6-Acetyl-2-((5-(4-(2-bromoethyl)piperazin-1-yl)pyridin-2-yl)amino)-8-cyclopentyl-5-methylpyrido[2,3-d]pyrimidin-7(8H)-one (222 mg, 0.4 mmol), diisopropylethylamine (129 mg, 1 mmol) and a catalytic amount of potassium iodide were added. The mixture was heated to 80° C. and reacted overnight, concentrated and then purified by column chromatography to yield a product of 50 mg. [M+H]⁺=898.5.

Step 2: Preparation of (S)-3-(5-(4-((1-(2-(4-(6-((6-acetyl-8-cyclopentyl-5-methyl-7-oxo-7,8-dihydro-pyrido[2,3-d]pyrimidin-2-yl)amino)pyridin-3-yl)piperazin-1-yl)ethyl)piperidin-4-yl)methyl)piperidin-1-yl)-1-oxoisoindolin-2-yl)piperidine-2,6-dione dihydrochloride (S)-3-(5-(4-((1-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperidin-4-yl)methyl)piperidin-1-yl)-1-oxoisoindolin-2-yl)piperidine-2,6-dione (50 mg, 0.056 mmol) was dissolved in methanol (5 mL), and a solution of hydrogen chloride in methanol (20 mL) was added. The mixture was reacted overnight at room temperature, concentrated and then purified by a preparative TLC plate to yield a product of 40 mg. ¹HNMR (400 MHz, d₆-DMSO) δ 10.96 (s, 2H), 9.03 (s, 1H), 8.13 (s, 1H), 7.90-7.86 (m, 2H), 7.56 (d, J=8.4 Hz, 1H), 7.19-7.16 (m, 2H), 5.88-5.84 (m, 1H), 5.09-5.04 (m, 1H), 4.38-4.21 (m, 2H), 3.97-3.69 (m, 16H), 3.00-2.88 (m, 7H), 2.63-2.58 (m, 2H), 2.45 (s, 3H), 2.36 (s, 3H), 2.28-2.23 (m, 3H), 2.02-1.91 (m, 7H), 1.81-1.77 (m, 6H), 1.63-1.61 (m, 3H). [M+H]⁺=898.5.

42) The synthesis route of Compound 40 was illustrated as below:

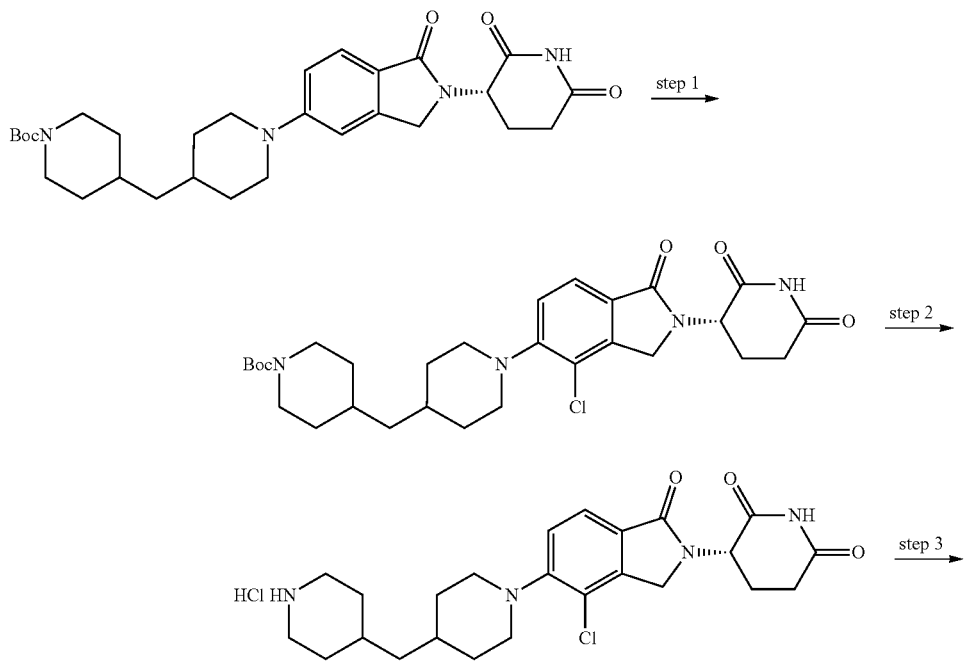

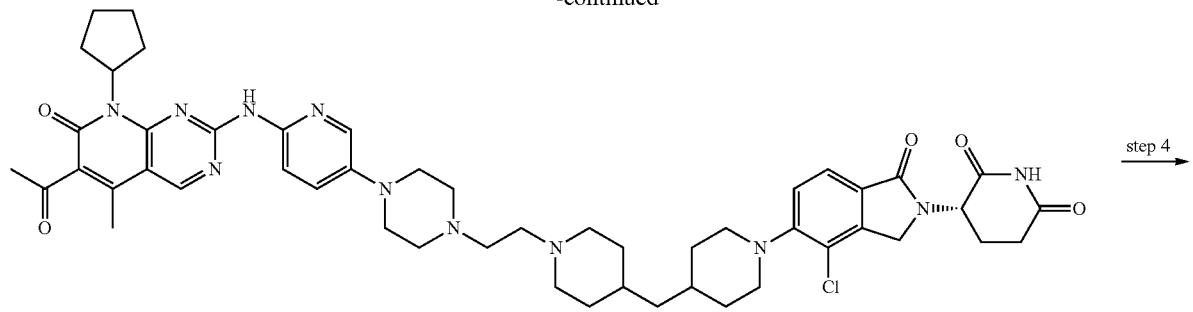

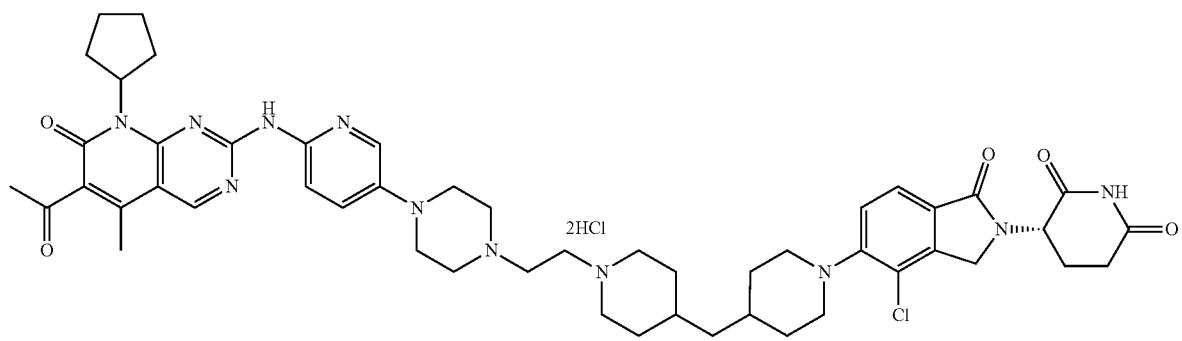 [SMILES: CC(=O)c1c(C)c2cnc(Nc3ccc(N4CCN(CCN5CCC(CC6CCN(c7ccc8c(c7Cl)CN([C@H]7CCC(=O)NC7=O)C8=O)CC6)CC5)CC4)cn3)nc2n(C2CCCC2)c1=O]

Step 1: Preparation of tert-butyl (S)-4-((1-(4-chloro-2-(2,6-dioxopiperidin-3-yl)-1-oxoisoindolin-5-yl)piperidin-4-yl)methyl)piperidine-1-carboxylate Tert-butyl (S)-4-((1-(2-(2,6-dioxopiperidin-3-yl)-1-oxoisoindolin-5-yl)piperidin-4-yl)methyl)piperidine-1-carboxylate (180 mg, 0.34 mmol) was dissolved in a mixed solution (10 mL) of dichloromethane and methanol (dichloromethane:methanol=10:1), and trifluoroacetic acid (66 mg, 0.68 mmol) and N-chlorosuccinimide (53.4 mg, 0.4 mmol) were added. The mixture was reacted overnight at room temperature, concentrated and then purified by a preparative TLC plate to yield a product of 38 mg. [M+H]$^+$=559.3.

Step 2: Preparation of (S)-3-(4-chloro-1-oxo-5-(4-(piperidin-4-ylmethyl)piperidin-1-yl)isoindolin-2-yl)piperidine-2,6-dione dihydrochloride Tert-butyl (S)-4-((1-(4-chloro-2-(2,6-dioxopiperidin-3-yl)-1-oxoisoindolin-5-yl)piperidin-4-yl)methyl)piperidine-1-carboxylate (38 mg, 0.068 mmol) was dissolved in methanol (5 mL), and a solution of hydrogen chloride in methanol (20 mL) was added. The mixture was reacted overnight at room temperature and concentrated to yield a crude product of 40 mg. [M+H]$^+$=459.3.

Step 3: Preparation of (S)-3-(5-(4-((1-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperidin-4-yl)methyl)piperidin-1-yl)-4-chloro-1-oxoisoindolin-2-yl)piperidine-2,6-dione (S)-3-(4-chloro-1-oxo-5-(4-(piperidin-4-ylmethyl)piperidin-1-yl)isoindolin-2-yl)piperidine-2,6-dione hydrochloride (40 mg) was dissolved in acetonitrile (20 mL). 6-Acetyl-2-((5-(4-(2-bromoethyl)piperazin-1-yl)pyridin-2-yl)amino)-8-cyclopentyl-5-methylpyrido[2,3-d]pyrimidin-7(8H)-one (39 mg, 0.07 mmol), diisopropylethylamine (26 mg, 0.2 mmol) and a catalytic amount of potassium iodide were added. The mixture was heated to 80° C. and reacted overnight, concentrated and then purified by a preparative TLC plate to yield a product of 18 mg. [M+H]$^+$=932.5.

Step 4: Preparation of (S)-3-(5-(4-((1-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperidin-4-yl)methyl)piperidin-1-yl)-4-chloro-1-oxoisoindolin-2-yl)piperidine-2,6-dione dihydrochloride (S)-3-(5-(4-((1-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperidin-4-yl)methyl)piperidin-1-yl)-4-chloro-1-oxoisoindolin-2-yl)piperidine-2,6-dione (18 mg, 0.02 mmol) was dissolved in methanol (5 mL), and a solution of hydrogen chloride in methanol (20 mL) was added. The mixture was reacted overnight at room temperature, concentrated and then purified by a preparative TLC plate to yield a product of 13 mg. $^1$HNMR (400 MHz, d$_6$-DMSO) δ 11.14 (brs, 1H), 10.99 (s, 1H), 9.04 (s, 1H), 8.13 (d, J=2.4 Hz, 1H), 8.01-7.98 (m, 1H), 7.86 (d, J=9.2 Hz, 1H), 7.69-7.65 (m, 1H), 7.28 (d, J=8 Hz, 1H), 5.89-5.84 (m, 1H), 5.13-5.08 (m, 1H), 4.44-4.24 (m, 2H), 3.84-3.70 (m, 9H), 3.01-2.89 (m, 4H), 2.78-2.58 (m, 5H), 2.46 (s, 3H), 2.36 (s, 3H), 2.29-2.20 (m, 2H), 2.02-2.92 (m, 6H), 1.83-1.77 (m, 5H), 1.64-1.53 (m, 6H), 1.37-1.24 (m, 7H). [M+H]$^+$=932.5.

43) The synthesis route of Compound 37 was illustrated as below:

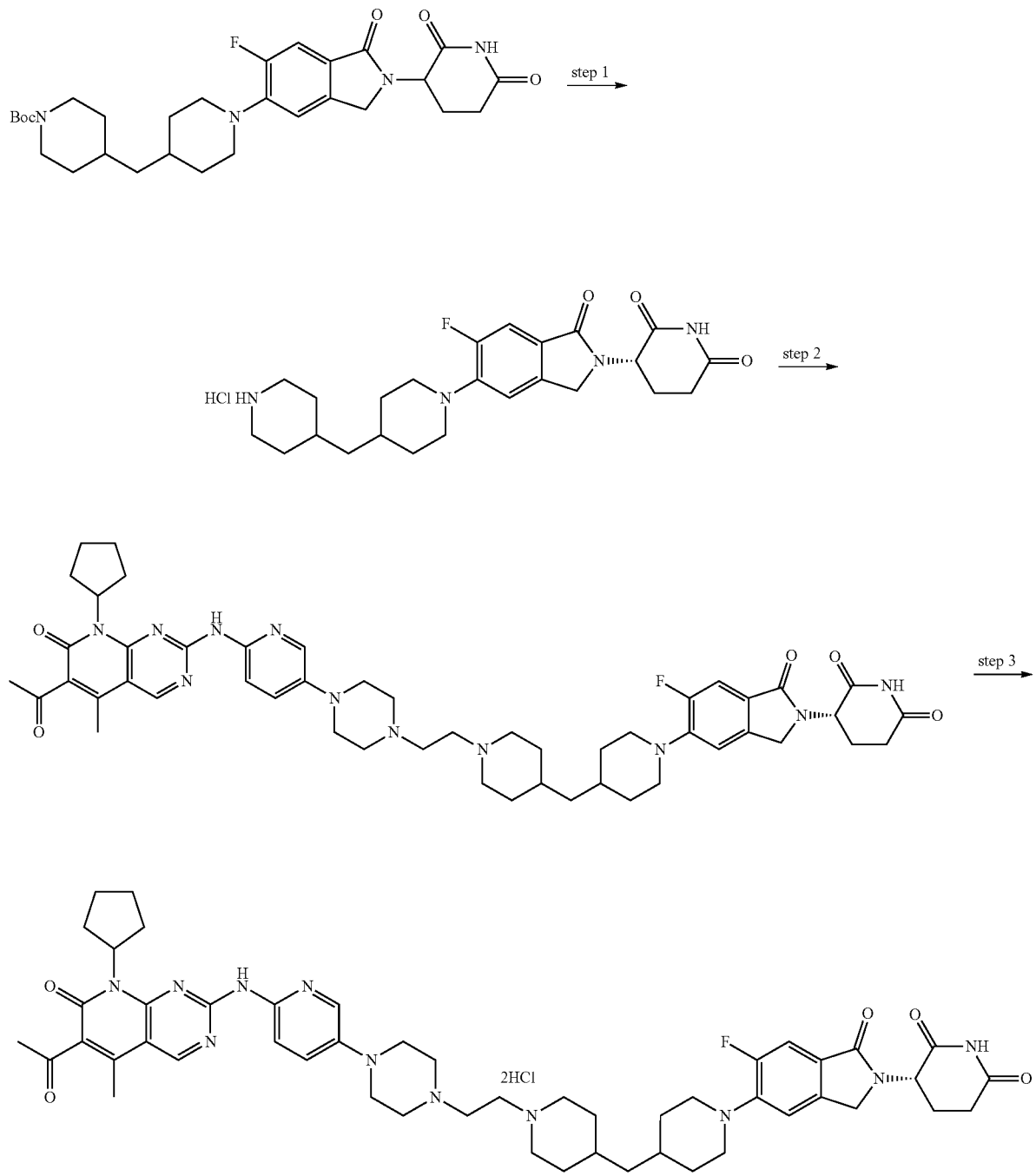

Step 1: Preparation of 3-(6-fluoro-1-oxo-5-(4-(piperidin-4-ylmethyl)piperidin-1-yl)isoindolin-2-yl)piperidine-2,6-dione hydrochloride Tert-butyl 4-((1-(2-(2,6-dioxopiperidin-3-yl)-6-fluoro-1-oxoisoindolin-5-yl)piperidin-4-yl)methyl)piperidine-1-carboxylate (220 mg, 0.4 mmol) was dissolved in methanol (10 mL), and a solution of hydrogen chloride in methanol (100 mL) was added. The mixture was reacted overnight at room temperature and concentrated to yield a crude product of 220 mg, which was directly used in the next step. [M+H]⁺= 443.3.

Step 2: Preparation of 3-(5-(4-((1-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperidin-4-yl)methyl)piperidin-1-yl)-6-fluoro-1-oxoisoindolin-2-yl)piperidine-2,6-dione 3-(6-Fluoro-1-oxo-5-(4-(piperidin-4-ylmethyl)piperidin-1-yl)isoindolin-2-yl)piperidine-2,6-dione hydrochloride (220 mg) was dissolved in acetonitrile (20 mL). 6-Acetyl-2-((5-(4-(2-bromoethyl)piperazin-1-yl)pyridin-2-yl)amino)-8-cyclopentyl-5-methylpyrido[2,3-d]pyrimidin-7(8H)-one (277 mg, 0.5 mmol), diisopropylethylamine (129 mg, 1 mmol) and a catalytic amount of potassium iodide were added. The mixture was heated to 80° C. and reacted overnight, concentrated and then purified by a preparative TLC plate to yield a product of 14 mg. [M+H]⁺=916.5.

Step 3: Preparation of 3-(5-(4-((1-(2-(4-(6-((6-acetyl-8-cyclopentyl-5-methyl-7-oxo-7,8-dihydro-pyrido[2,3-d]pyrimidin-2-yl)amino)pyridin-3-yl)piperazin-1-yl)ethyl)piperidin-4-yl)methyl)piperidin-1-yl)-6-fluoro-1-oxoisoindolin-2-yl)piperidine-2,6-dione dihydrochloride 3-(5-(4-((1-(2-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)ethyl)piperidin-4-yl)methyl)piperidin-1-yl)-6-fluoro-1-oxoisoindolin-2-yl)piperidine-2,6-dione (14 mg, 0.015 mmol) was dissolved in methanol (5 mL), and a solution of hydrogen chloride in methanol (15 mL) was added. The mixture was reacted overnight at room temperature and concentrated to yield a product of 14 mg. ¹HNMR (400 MHz, d₆-DMSO) δ 10.99 (s, 1H), 9.02 (s, 1H), 8.16-8.15 (m, 1H), 7.94-7.92 (m, 1H), 7.84-7.81 (m, 1H), 7.46-7.33 (m, 1H), 7.24-7.20 (m, 1H), 5.87-5.83 (m, 1H), 5.34-5.32 (m, 1H), 4.39 (s, 2H), 3.03-2.91 (m, 5H), 2.79-2.69 (m, 7H), 2.44 (s, 3H), 2.34 (s, 3H), 2.28-2.19 (m, 5H), 2.06-1.88 (m, 11H), 1.83-1.75 (m, 6H), 1.62-1.45 (m, 10H). [M+H]⁺=916.5.

44) The synthesis route of Compound 39 was illustrated as below:

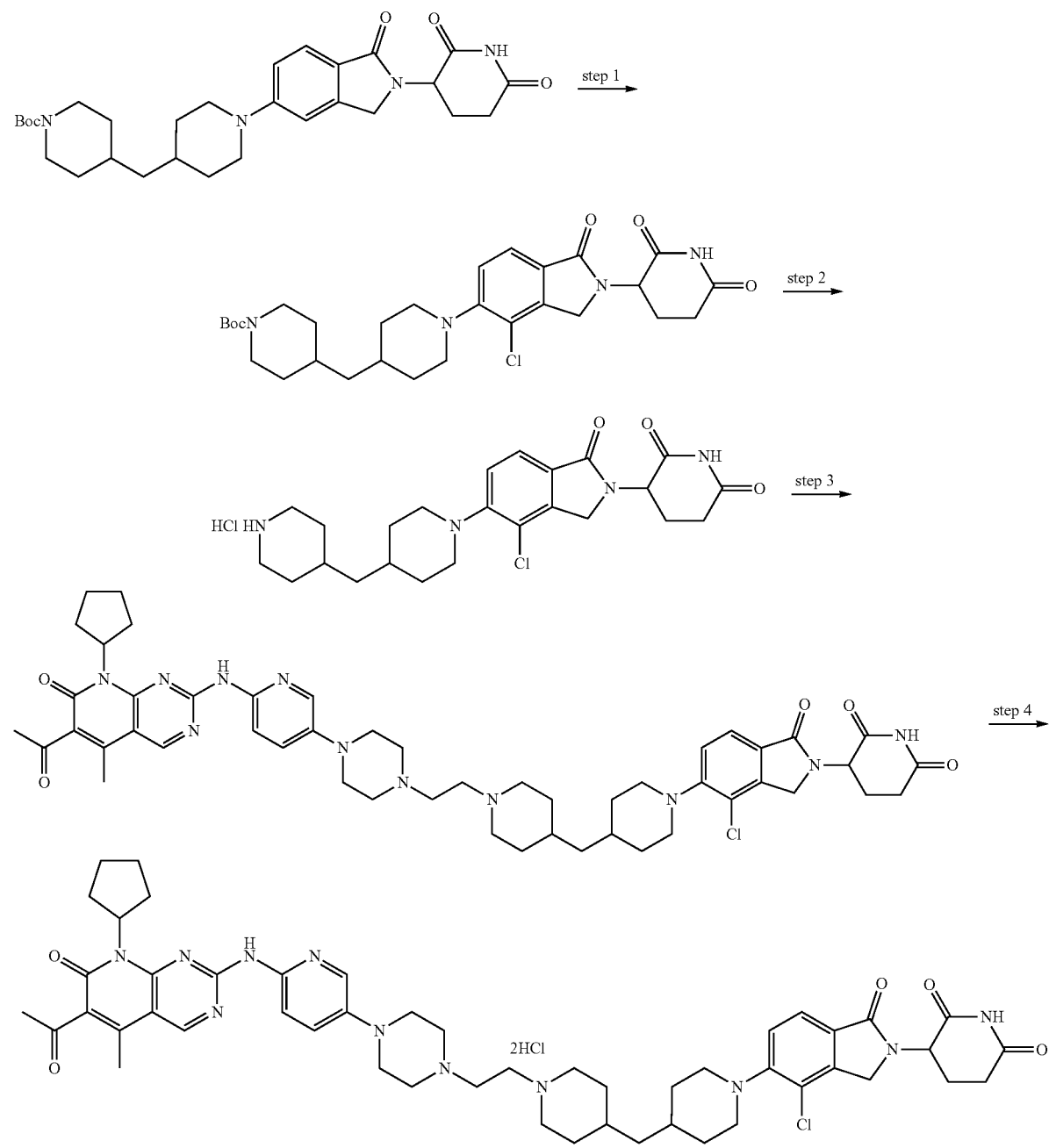

Step 1: Preparation of tert-butyl 4-((1-(4-chloro-2-(2,6-dioxopiperidin-3-yl)-1-oxoisoindolin-5-yl)piperidin-4-yl)methyl)piperidine-1-carboxylate Tert-butyl 4-((1-(2-(2,6-dioxopiperidin-3-yl)-1-oxoisoindolin-5-yl)piperidin-4-yl)methyl)piperidine-1-carboxylate (200 mg, 0.38 mmol) was dissolved in a mixed solution (10 mL) of dichloromethane and methanol (dichloromethane:methanol=10:1), and trifluoroacetic acid (66 mg, 0.68 mmol) and N-chlorosuccinimide (53.4 mg, 0.4 mmol) were added. The mixture was reacted overnight at room temperature, concentrated and then purified by a preparative TLC plate to yield a product of 80 mg. $[M+H]^+=559.3$.

Step 2: Preparation of 3-(4-chloro-1-oxo-5-(4-(piperidin-4-ylmethyl)piperidin-1-yl)isoindolin-2-yl)piperidine-2,6-dione hydrochloride Tert-butyl 4-((1-(4-chloro-2-(2,6-dioxopiperidin-3-yl)-1-oxoisoindolin-5-yl)piperidin-4-yl)methyl)piperidine-1-carboxylate (40 mg, 0.07 mmol) was dissolved in methanol (5 mL), and a solution of hydrogen chloride in methanol (20 mL) was added. The mixture was reacted overnight at room temperature and concentrated to yield a crude product of 40 mg. $[M+H]^+=459.3$.

Step 3: Preparation of 3-(5-(4-((1-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperidin-4-yl)methyl)piperidin-1-yl)-4-chloro-1-oxoisoindolin-2-yl)piperidine-2,6-dione 3-(4-Chloro-1-oxo-5-(4-(piperidin-4-ylmethyl)piperidin-1-yl)isoindolin-2-yl)piperidine-2,6-dione hydrochloride (40 mg) was dissolved in acetonitrile (20 mL). 6-Acetyl-2-((5-(4-(2-bromoethyl)piperazin-1-yl)pyridin-2-yl)amino)-8-cyclopentyl-5-methylpyrido[2,3-d]pyrimidin-7(8H)-one (39 mg, 0.07 mmol), diisopropylethylamine (26 mg, 0.2 mmol) and a catalytic amount of potassium iodide were added. The mixture was heated to 80° C. and reacted overnight, concentrated and then purified by a preparative TLC plate to yield a product of 16 mg. $[M+H]^+=932.5$.

Step 4: Preparation of 3-(5-(4-((1-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)piperidin-4-yl)methyl)piperidin-1-yl)-4-chloro-1-oxoisoindolin-2-yl)piperidine-2,6-dione dihydrochloride 3-(5-(4-((1-(2-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)ethyl)piperidin-4-yl)methyl)piperidin-1-yl)-4-chloro-1-oxoisoindolin-2-yl)piperidine-2,6-dione (16 mg, 0.017 mmol) was dissolved in methanol (5 mL), and a solution of hydrogen chloride in methanol (20 mL) was added. The mixture was reacted overnight at room temperature, concentrated and then purified by a preparative TLC plate to yield a product of 3.4 mg. $^1$HNMR (400 MHz, $d_6$-DMSO) δ 11.30 (brs, 1H), 10.99 (s, 1H), 10.42 (brs, 1H), 9.05 (s, 1H), 8.13-8.05 (m, 2H), 7.86 (d, J=9.2 Hz, 1H), 7.66 (d, J=8 Hz, 1H), 7.28 (d, J=8 Hz, 1H), 5.91-5.82 (m, 1H), 5.13-5.08 (m, 1H), 4.44-4.24 (m, 2H), 3.07-2.87 (m, 3H), 2.78-2.58 (m, 3H), 2.45 (s, 3H), 2.37 (s, 3H), 2.27-2.20 (m, 2H), 2.02-1.91 (m, 5H), 1.83-1.77 (m, 4H), 1.47-1.45 (m, 5H), 1.34-1.24 (m, 8H). $[M+H]^+=932.5$.

45) The synthesis route of Compound 42 was illustrated as below:

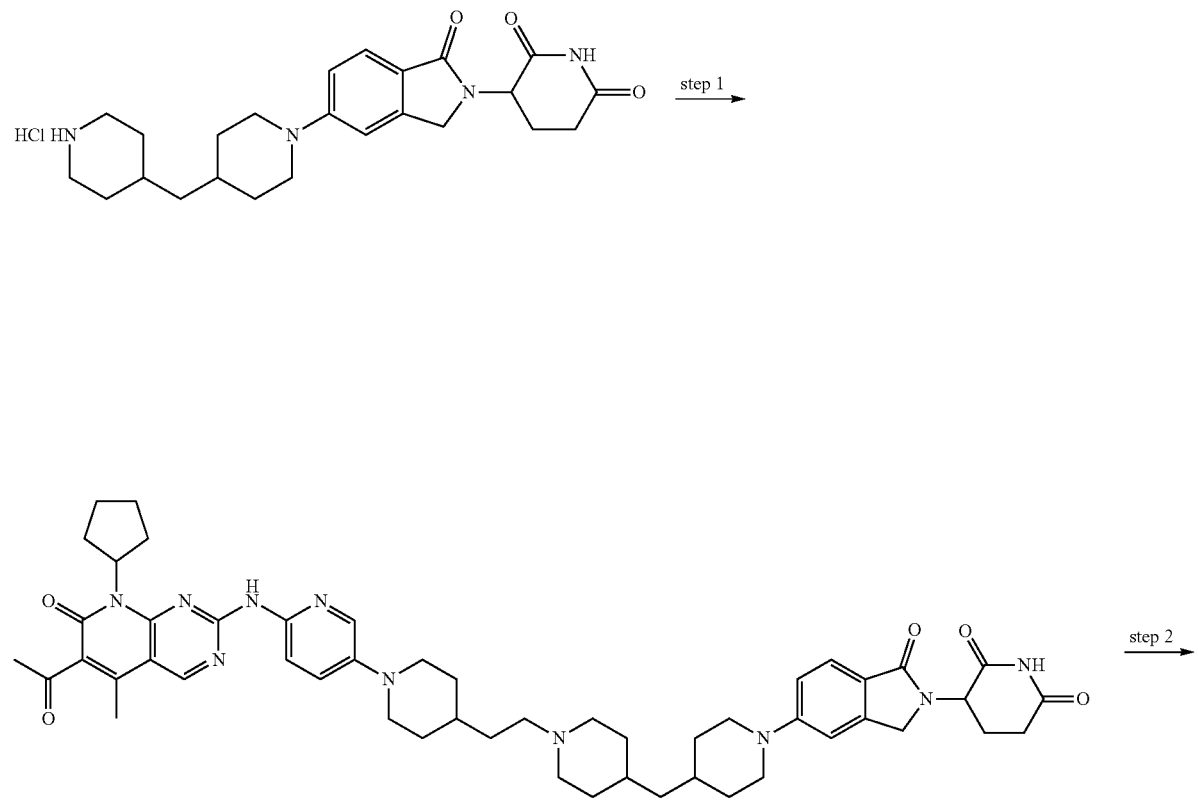

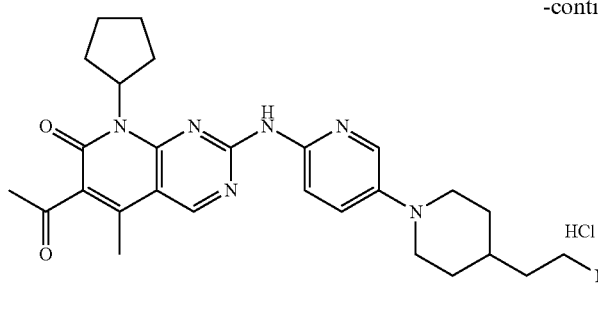
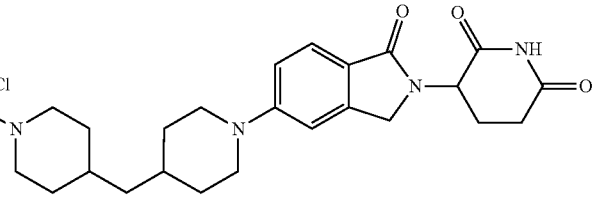

Step 1: Preparation of 3-(5-(4-((1-(2-(1-(6-((6-acetyl-8-cyclopentyl-5-methyl-7-oxo-7,8-dihydropyrido[2,3-d]pyrimidin-2-yl)amino)pyridin-3-yl)piperidin-4-yl)ethyl)piperidin-4-yl)methyl)piperidin-1-yl)-1-oxoisoindolin-2-yl)piperidine-2,6-dione 3-(1-Oxo-5-(4-(piperidin-4-ylmethyl)piperidin-1-yl)isoindolin-2-yl)piperidine-2,6-dione hydrochloride (80 mg, 0.17 mmol) was dissolved in acetonitrile (20 mL). 6-Acetyl-2-((5-(4-(2-chloroethyl)piperidin-1-yl)pyridin-2-yl)amino)-8-cyclopentyl-5-methylpyrido[2,3-d]pyrimidin-7(8H)-one (100 mg, 0.2 mmol), diisopropylethylamine (129 mg, 1 mmol) and a catalytic amount of potassium iodide were added. The mixture was heated to 80° C. and reacted overnight, concentrated and then purified by a preparative TLC plate to yield a product of 4.7 mg. [M+H]⁺=897.5.

Step 2: Preparation of 3-(5-(4-((1-(2-(1-(6-((6-acetyl-8-cyclopentyl-5-methyl-7-oxo-7,8-dihydropyrido[2,3-d]pyrimidin-2-yl)amino)pyridin-3-yl)piperidin-4-yl)ethyl)piperidin-4-yl)methyl)piperidin-1-yl)-1-oxoisoindolin-2-yl)piperidine-2,6-dione hydrochloride 3-(5-(4-((1-(2-(1-(6-((6-Acetyl-8-cyclopentyl-5-methyl-7-oxo-7,8-dihydropyrido[2,3-d]pyrimidin-2-yl)amino)pyridin-3-yl)piperidin-4-yl)ethyl)piperidin-4-yl)methyl)piperidin-1-yl)-1-oxoisoindolin-2-yl)piperidine-2,6-dione (4.7 mg, 0.005 mmol) was dissolved in methanol (5 mL), and a solution of hydrogen chloride in methanol (10 mL) was added. The mixture was reacted overnight at room temperature, concentrated and then purified by a preparative TLC plate to yield a product of 4 mg. ¹HNMR (400 MHz, CDCl₃) δ 8.81 (s, 1H), 8.00 (s, 1H), 7.72 (d, J=8.4 Hz, 1H), 7.39-7.37 (m, 1H), 7.00-6.98 (m, 1H), 6.88 (s, 1H), 5.92-5.83 (m, 1H), 5.37-5.34 (m, 1H), 5.21-5.16 (m, 1H), 4.43-4.24 (m, 2H), 3.85-3.82 (m, 2H), 3.64-3.61 (m, 4H), 3.47-3.42 (m, 1H), 3.06-3.02 (m, 2H), 2.88-2.63 (m, 8H), 2.56 (s, 3H), 2.38-2.27 (m, 6H), 2.24-2.18 (m, 3H), 2.06-1.99 (m, 6H), 1.78-1.32 (m, 15H). [M+H]⁺=897.5.

2. Verification of In-Vitro Kinase Inhibitory Activity of CDK4/6 Inhibitors

1) Verification of In-Vitro Kinase Inhibitory Activity of CDK4/6 Inhibitors:

The assay was performed in a U-bottom 384-well plate (coming, 4512 #). The final volume for assay was 16 μL, and the reaction temperature was 27° C. CDK4/CyclinD3 was produced by Wuxi Biortus Biosciences Co. Ltd. The concentration of the kinase was determined by the results of the optimization experiment. The kinase was diluted with an assay buffer (50 mM Tris HCl pH 8.0, 0.01% Tween 20, 50 μg/mL BSA, and 5 mM MgCl₂) to obtain a corresponding kinase solution (2.4× concentration). The compound was dissolved in dimethyl sulfoxide (DMSO) to reach a concentration of 10 mM. At the time of use, the compound was diluted to 10 concentration gradients ranging from 25 nM to 500 μM with DMSO, and each resulting solution was diluted 8.3-fold with the assay buffer to obtain a solution of the compound (6× concentration). The polypeptide substrate and ATP were diluted with the assay buffer to obtain a mixed solution (2.4× concentration) of the polypeptide substrate and ATP. 2 μL of the test compound solution was mixed with 5 μL of the kinase solution, and the mixture was incubated for 10 min. 5 μL of the mixed solution of the polypeptide substrate and ATP was then added. The mixture was incubated at 27° C. for 180 min, and then the reaction was terminated by adding 4 μL of EDTA with a concentration of 120 mM to each sample. An assay buffer containing 20 μM of staurosporine was used instead of the solution of the compound as 100%-inhibition control, and DMSO was used instead of the solution of the compound as 0%-inhibition control. Each assay was conducted in at least two replicates.

The final concentrations of the reagents in the assay were as follows. ATP had a concentration of 2 mM, Peptide had a concentration of 1 μM, and CDK4/CyclinD3 had a concentration of 20 nM. The reaction mixture was analyzed on a Caliper EZ Reader II by electrophoretic separation of the fluorescent substrate and the phosphorylated product. Data were calculated by using GraphPad Prism version 6.0 and IC50 values were obtained by adjusting the non-linear regression models of the dose response curves.

2) Verification of In-Vitro Kinase Inhibitory Activity of CDK4/6 Inhibitors:

The assay was performed in a U-bottom 384-well plate (coming, 4512 #). The final volume for assay was 16 μL, and the reaction temperature was 27° C. CDK6/CyclinD3 was produced by Wuxi Biortus Biosciences Co. Ltd. The concentration of the kinase was determined by the optimization experiment, and the kinase was diluted with an assay buffer (20 mM MES pH 6.75, 0.01% Tween 20, 50 μg/mL BSA, and 2 mM MgCl₂) to obtain a corresponding kinase solution (2.4× concentration). The compound was dissolved in dimethyl sulfoxide (DMSO) to reach a concentration of 10 mM. At the time of use, the compound was diluted to 10 concentration gradients ranging from 25 nM to 500 μM with DMSO, and each resulting solution was diluted 8.3-fold with the assay buffer to obtain a solution of the compound (6× concentration). The polypeptide substrate and ATP were diluted with the assay buffer to obtain a mixed solution (2.4× concentration) of the polypeptide substrate and ATP. 2 μL of the test compound solution was mixed with 5 μL of the kinase solution, and the mixture was incubated for 10 min.

5 µL of the mixed solution of the polypeptide substrate and ATP was then added. The mixture was incubated at 27° C. for 120 min, and then the reaction was terminated by adding 4 µL of EDTA with a concentration of 120 mM to each sample. An assay buffer containing 20 M of staurosporine was used instead of the solution of the compound as 100%-inhibition control, and DMSO was used instead of the solution of the compound as 0%-inhibition control. Each assay was conducted in at least two replicates.

The final concentrations of the reagents in the assay were as follows. ATP had a concentration of 2 mM, Peptide had a concentration of 1 µM, and CDK6/CyclinD3 had a concentration of 20 nM. The reaction mixture was analyzed on a Caliper EZ Reader II by electrophoretic separation of the fluorescent substrate and the phosphorylated product. Data were calculated by using GraphPad Prism version 6.0 and IC50 values were obtained by adjusting the non-linear regression models of the dose response curves.

3) In-Vitro Inhibition Assay of CRBN Activity:

The assay was performed in a U-bottom 384-well plate (coming, 4514 #). The final volume for assay was 20 µL, and the reaction temperature was 27° C. CRBN was produced by Wuxi Biortus Biosciences Co. Ltd. The concentration of the kinase was determined by the optimization experiment, and the kinase was diluted with an assay buffer (50 mM Tris, pH 7.5, 100 mM NaCl, and 0.01% Pluronic acid) to obtain a corresponding kinase solution (2× concentration). The compound was dissolved in dimethyl sulfoxide (DMSO) to reach a concentration of 10 mM. At the time of use, the compound was diluted to 10 concentration gradients ranging from 1.31 µM to 5 mM with DMSO, and each resulting solution was diluted 25-fold with the assay buffer to obtain a solution of the compound (4× concentration). The fluorescent substrate Cy5-Thalidomide was diluted with the assay buffer to obtain a substrate solution (4× concentration). 5 µL of the test compound solution was mixed with 5 µL of the substrate solution, and 10 µL of the kinase solution was added to the mixture. The mixture was incubated at 27° C. for 60 min. Each assay was conducted in at least two replicates. The assay buffer containing 10 M of the positive control (Thalidomide) was used instead of the solution of the compound as 100%-inhibition control, and DMSO was used instead of the solution of the compound as 0%-inhibition control. Each assay was conducted in at least two replicates.

The final concentrations of the reagents in the assay were as follows. Cy5-Thalidomide had a concentration of 10 nM, and CRBN had a concentration of 180 nM. The data of fluorescence polarization assay were read on TECAN infinite M1000. Data were calculated by using GraphPad Prism version 6.0, and IC50 values were obtained by adjusting the non-linear regression models of the dose response curves.

The results of in-vitro kinase inhibitory activities of CDK4/6 inhibitors were as follows:

| IC50 (half maximal inhibitory concentration, nM) | | | | |
|---|---|---|---|---|
| Target compound | CDK2 | CDK4 | CDK6 | CDK9 |
| Compound 1 | >10000 | 38.8 | 21.3 | 4176 |
| Compound 3 | 9660 | 16.1 | 14.5 | 2853 |
| Compound 5 | 9906 | 10 | 6.6 | 5473 |
| Compound 4 | >10000 | 10.7 | 9.7 | 8637 |
| Compound 2 | >10000 | 36.8 | 22 | 8710 |
| Compound 6 | 1140 | 24.2 | 42.4 | 946 |
| Compound 7 | 7479 | 54.7 | 30 | 9917 |
| Compound 8 | 8995 | 19.9 | 16.1 | 3811 |
| Compound 9 | >10000 | 19.2 | 14.2 | 3511 |

| IC50 (half maximal inhibitory concentration, nM) | | | | |
|---|---|---|---|---|
| Target compound | CDK2 | CDK4 | CDK6 | CDK9 |
| Compound 10 | >10000 | 11.54 | 3.21 | 4152 |
| Compound 12 | 1034 | 13 | 23.2 | 687.9 |
| Compound 13 | / | 71.07 | 26.61 | >10000 |
| Compound 16 | / | 60.1 | 26.42 | >10000 |
| Compound 18 | / | 99.5 | 37.81 | >10000 |
| Compound 20 | >10000 | 44.61 | 19.58 | 3759 |
| Compound 22 | >10000 | 27.41 | 18.19 | 6215 |
| Compound 11 | 8202 | 24.63 | 21.1 | 4439 |
| Compound 17 | / | 67.1 | 29.64 | >10000 |
| Compound 19 | / | 54.8 | 20.48 | 5610 |
| Compound 21 | / | 53.16 | 37.1 | 3951 |
| Compound 23 | / | 48.8 | 22.08 | 4577 |
| Compound 26 | / | 38.37 | 55.22 | 3999 |
| Compound 27 | / | 45.43 | 29.64 | >10000 |
| Compound 29 | / | 37.81 | 42.14 | 3645 |
| Compound 34 | / | 17.6 | 9.84 | 1560 |
| Compound 36 | / | 12.66 | 4.44 | 1482 |
| Compound 38 | / | 8.88 | 6.73 | 1398 |
| Compound 39 | / | 56.09 | 11.27 | 5765 |
| Compound 40 | / | 54.95 | 23.34 | 6805 |
| Compound 42 | / | 33.33 | 19.24 | >10000 |
| LY-2835219 (Abemaciclib) | 1020 | 9.1 | 24.5 | 1273 |
| Palbociclib | >10000 | 14.6 | 13.8 | >10000 |
| Staurosporine | 14.2 | 310.2 | 169.9 | 412.3 |

The results showed that each of the CDK4/6 inhibitors with different structures synthesized above had inhibitory effects on CDK4 and CDK6. Among them, compounds such as Compound 5 and Compound 4 showed results similar to that of the positive control. IC50 of these CDK4/6 inhibitors against CDK2 and CDK9 were tested in the meantime. It was found that none of these CDK4/6 inhibitors had inhibitory effect on CDK2 and CDK9, which indicated that the synthesized CDK4/6 inhibitors were site-specific and could be used as selective CDK4/6 inhibitors.

| CRBN | |
|---|---|
| Target compound | IC50 (µM) |
| Compound 1 | 3 |
| Compound 3 | 1.2 |
| Compound 5 | 5.28 |
| Compound 4 | 2.08 |
| Compound 2 | 3 |
| Compound 6 | 2.51 |
| Compound 7 | 1.42 |
| Compound 8 | 1.21 |
| Thalidomide | 6.5 |

The results of the in-vitro inhibition assay of CRBN activity indicated that all of the synthesized compounds showed better inhibitory effects as compared with the positive control.

3. Growth Inhibitory Effects of CDK4/6 Inhibitors on Human Tumor Cells Cultured In Vitro Test drugs: Compounds of the present disclosure. Tumor cell strains: human colon cancer COLO205 cells and human breast cancer MCF-7 cells.

The growth inhibitory effects on human tumor cells COLO205 and MCF-7 cultured in vitro were observed by using a CellTiter-Glo Luminescent Cell Viability Assay Kit (Promega, Cat. No. G7572). Human tumor cells COLO205 and MCF-7 were both purchased from the American Type Culture Collection.

CellTiter-Glo Luminescent Cell Viability Assay: The previous cell culture medium was discarded, and the tumor cells were rinsed twice with PBS. An appropriate amount of trypsin (VWR, Cat. No. 0458-25G) was added to digest the tumor cells until most of the cells turned round and were detached from the wall. The trypsin digestion was terminated by adding an RPMI-1640 medium (COLO205; Gibco, Cat. No. A10491-01) containing 10% fetal bovine serum (Hyclone, Cat. No. SV30160.03) and MEM medium (MCF-7; Gibco, Cat. No. 10370-021) containing 10% fetal bovine serum and 0.01 mg/mL insulin, and the cells were gently pipetted with a pipette to completely suspend the tumor cells. After cell counting, a tumor cell suspension was prepared using a complete culture medium and the final concentration was 6.7×104 cells/mL. 90 µL of the tumor cell suspension was seeded in each well of a 96-well culture plate (6000 cells/well). The plate was then placed in an incubator with 5% $CO_2$ at 37° C. and incubated for 24 h. A test drug was added by using an Agilent Bravo Automated Liquid Handling Platform, and 10 µL of the sample was added in each well. The assay was conducted in triplicate for each group. A compound of the present disclosure was dissolved in DMSO (BioRoYee, Cat. No. AF0231), and then the resulting solution was diluted to 10 µM/L, 3.33 µM/L, 1.11 µM/L, 0.37 µM/L, 0.123 µM/L, 0.041 µM/L, 0.0137 µM/L, 0.0046 µM/L, and 0.0015 µM/L with the culture medium. The concentration of DMSO was lower than 0.1%, and a culture medium containing 0.1% DMSO was added to the well which was set as a vehicle control group. The 96-well plate was placed in an incubator with 5% $CO_2$ at 37° C. and incubated for 72 h. The 96-well plate to be tested was equilibrated at room temperature for 30 min, and 100 µL of Cell Titer-Glo reagent was added to each well. The contents of each well were mixed in an orbital shaker for 2 min to induce cell lysis, and the plate was incubated at room temperature for 10 min to achieve a constant value of fluorescent intensity. Finally, the chemiluminescence intensity was detected by TECAN M1000. Data were processed with Graphpad Prism 6.0 software. The growth curve of the cells was plotted. The cell growth inhibition rate of a drug was calculated, and the half maximal inhibitory concentration (IC50) of the drug was determined. The growth inhibitory effects of the compounds on human tumor cells cultured in vitro were as shown in the following Table.

| Target compound | IC50 (nM) COLO205 | IC50 (nM) MCF-7 |
|---|---|---|
| Compound 1 | 45.69 | >10000 |
| Compound 5 | 290.89 | 30.42 |
| Compound 4 | 69.15 | 50.51 |
| Compound 2 | 25.5 | >10000 |
| Compound 8 | 96.18 | 821.43 |
| Compound 9 | 246.67 | >10000 |
| Compound 13 | 59.38 | / |
| Compound 16 | 66.91 | >10000 |
| Compound 18 | 133.3 | >10000 |
| Compound 20 | 78.29 | >10000 |
| Compound 22 | 87.1 | >10000 |
| Compound 11 | 126.64 | >10000 |
| Compound 19 | 43.22 | >10000 |
| Compound 23 | / | 13.48 |
| Compound 27 | / | 71.57 |
| Compound 29 | / | 105.79 |
| Compound 34 | 68.85 | 442.47 |
| Compound 36 | 95.86 | / |
| Compound 38 | 76.15 | / |
| Compound 39 | 439.66 | / |
| Compound 40 | 50.89 | / |
| Compound 42 | 193.5 | / |

The results indicated that Compound 1, Compound 4, Compound 2 and Compound 8 had relatively good inhibitory effects on human colon cancer COLO205 cells, in particular, Compound 2 had the best inhibitory effect, and Compound 5, Compound 4, Compound 23 and Compound 27 had relatively good inhibitory effects on human breast cancer MCF-7 cells.

Those skilled in the art will recognize or be able to determine many equivalents of the specific embodiments and methods described herein only by means of routine experimentation. These equivalents are intended to be included within the scope of the present application.

What is claimed is:

1. A compound as represented by formula (I), or a pharmaceutically acceptable salt, a solvate or a stereoisomer thereof,

PBM-L-PDM (I)

wherein
PBM is a protein binding moiety for CDK4/6 selected from the group consisting of

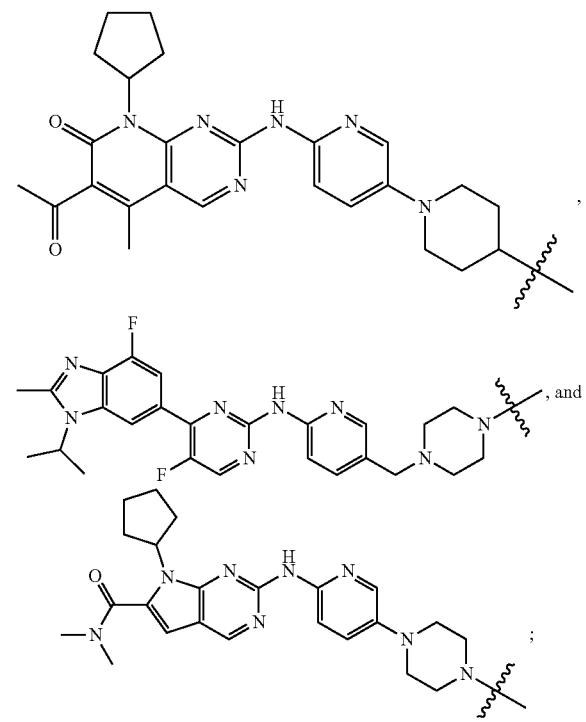

L is a linking moiety selected from the group consisting of

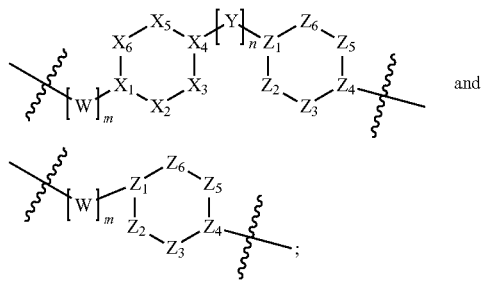

wherein
- each of W and Y is independently selected from O, CH$_2$, NHR$_1$, CR$_2$R$_3$, C(=O), C(=S), S(=O), or S(=O)$_2$; if present, each of R$_1$, R$_2$ and R$_3$ is independently hydrogen, linear or branched C1-C6 alkyl optionally substituted with one or more halogens, or C1-C6 alkoxy optionally substituted with one, two or three R$_4$; if present, each R$_4$ is independently hydrogen, halogen, hydroxy, C1-C3 alkyl, or formyl;
- each of m and n is independently 0, 1, 2, 3, 4, 5, or 6; and
- each of X$_1$, X$_4$, Z$_1$ and Z$_4$ is independently N or CH; each of X$_2$, X$_3$, X$_5$, X$_6$, Z$_2$, Z$_3$, Z$_5$ and Z$_6$ is independently NR$_5$, O, CR$_6$R$_7$, C(=O), or a covalent bond; if present, each of R$_5$, R$_6$ and R$_7$ is independently hydrogen, linear or branched C1-C6 alkyl optionally substituted with one or more halogens, or C1-C6 alkoxy optionally substituted with one, two or three R$_8$; if present, each R$_8$ is independently hydrogen, halogen, hydroxy, C1-C3 alkyl, or formyl; and
- PDM is a protein degradation moiety for CDK4/6, which has the following structure

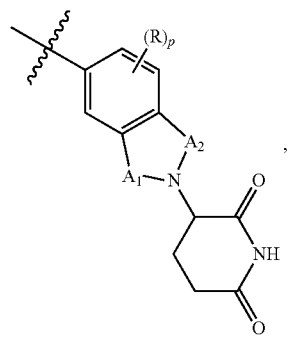

wherein each R is independently hydrogen, halogen, alkoxy, cyano, alkyl, haloalkyl, or haloalkoxy;

p is 0, 1, 2, or 3; and each of A$_1$ and A$_2$ is independently CH$_2$ or C(=O).

2. The compound according to claim 1, or a pharmaceutically acceptable salt, a solvate or a stereoisomer thereof, wherein said L is any one of the following structural formulas:

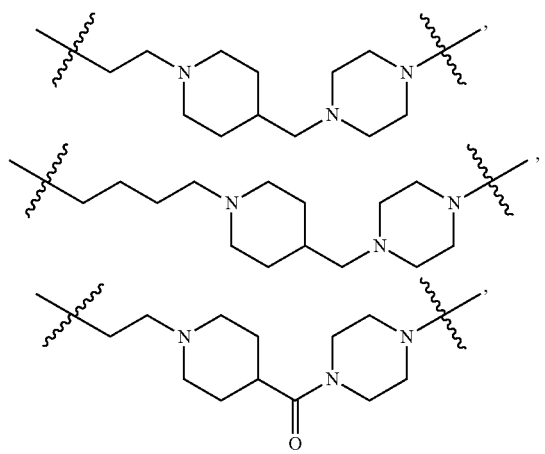

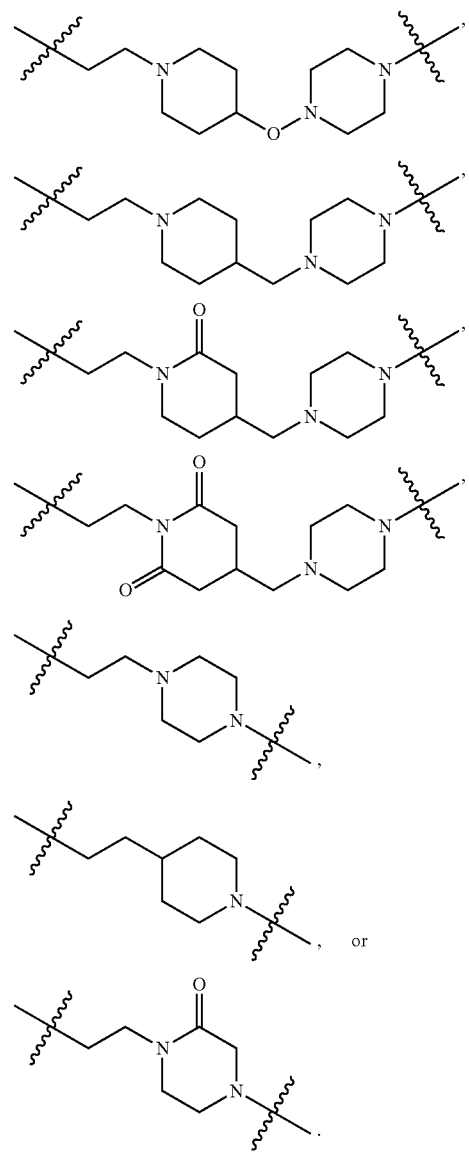

3. The compound according to claim 1, or a pharmaceutically acceptable salt, a solvate or a stereoisomer thereof, wherein said PDM is any one of the following structural formulas:

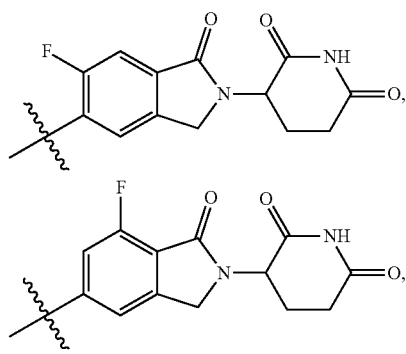

-continued

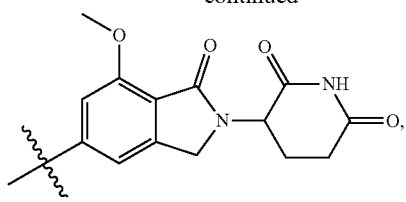

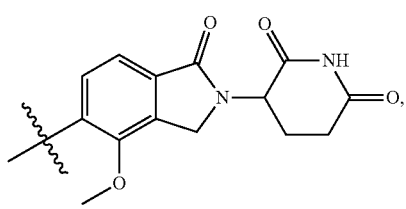

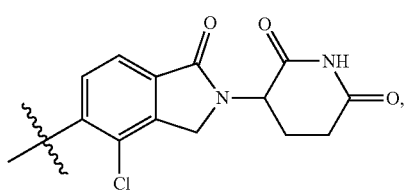

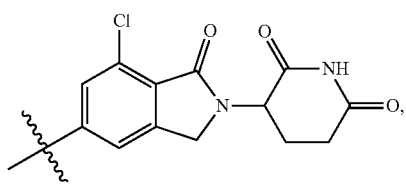

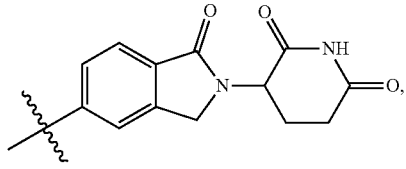

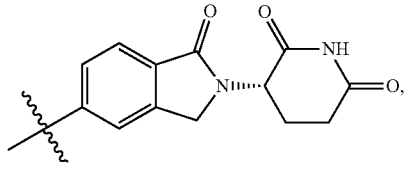

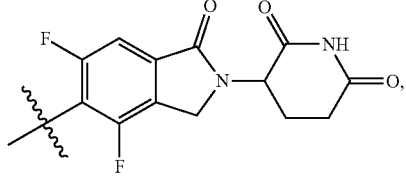

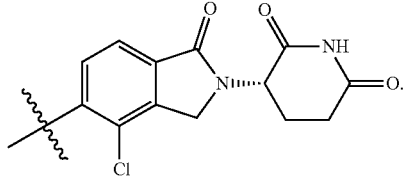

or

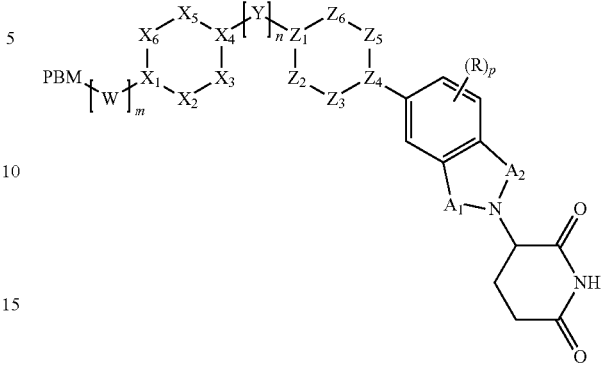

wherein said PBM is

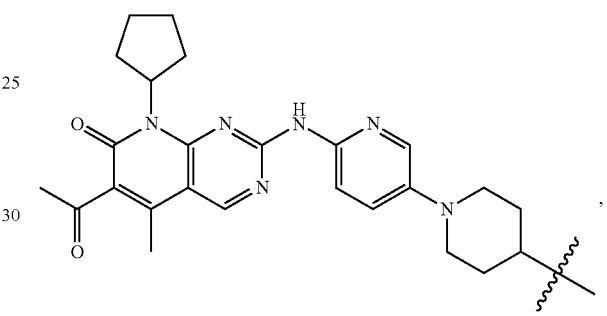

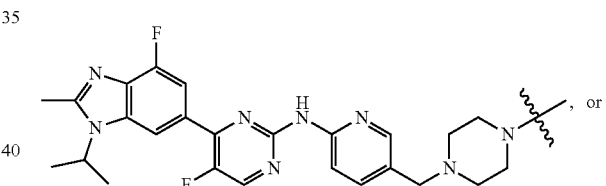

, or

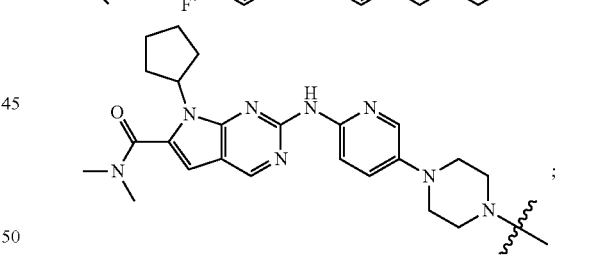

;

each of W and Y is independently O, CH$_2$, or C(=O);
each of m and n is independently 0, 1, 2, 3, or 4;
each of X$_1$, X$_4$, Z$_1$ and Z$_4$ is independently N or CH; each of X$_2$, X$_3$, X$_5$, X$_6$, Z$_2$, Z$_3$, Z$_5$ and Z$_6$ is independently O, CH$_2$, C(=O), or a covalent bond;
each R is independently hydrogen, halogen, or alkoxy;
p is 0, 1, or 2; and
each of A$_1$ and A$_2$ is independently CH$_2$ or C(=O).

4. The compound according to claim 1, or a pharmaceutically acceptable salt, a solvate or a stereoisomer thereof, wherein the compound is a compound as represented by formula (I')

5. The compound according to claim 1, or a pharmaceutically acceptable salt, a solvate or an stereoisomer thereof, wherein the compound is any one of compounds of the following formula (I-1) to formula (I-12):

I-1
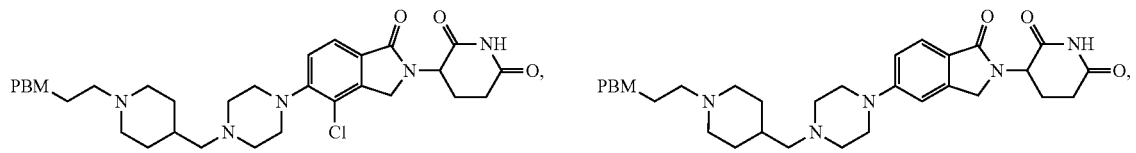
I-2
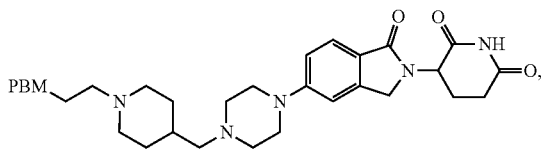
I-3
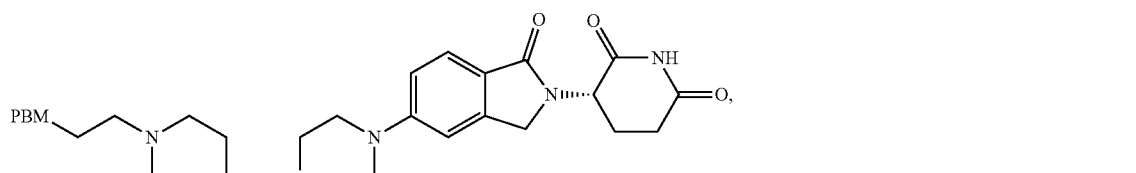
I-4
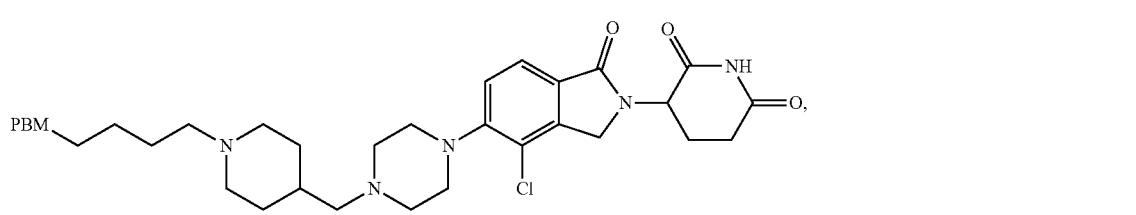
I-5
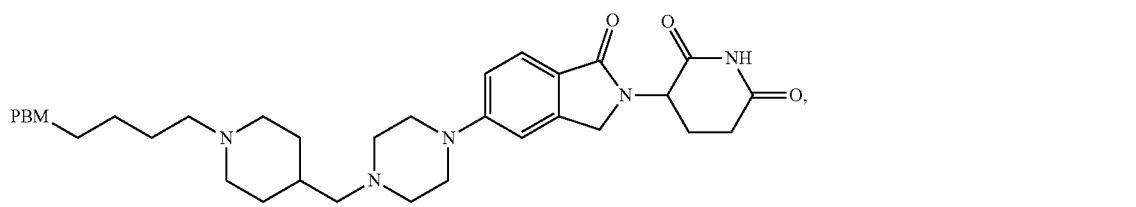
I-6
I-7
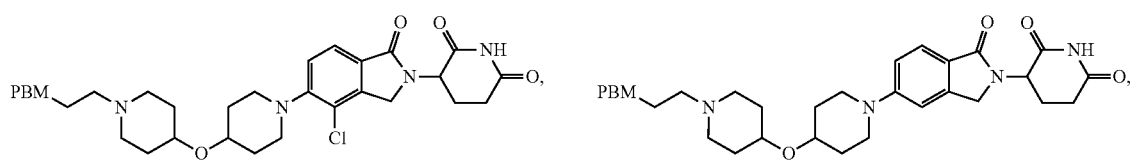
I-8
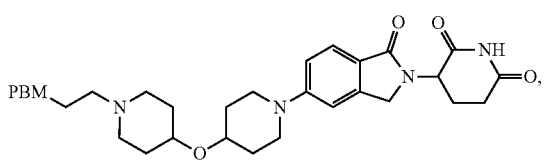
I-9
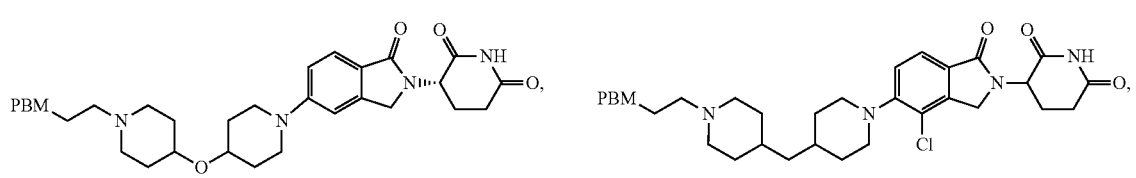
I-10
I-11
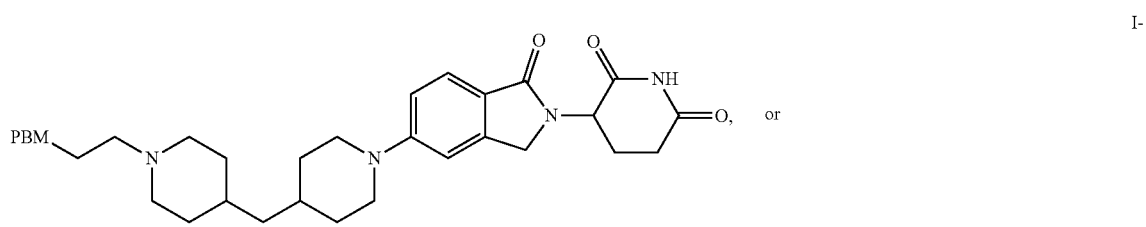
or I-12
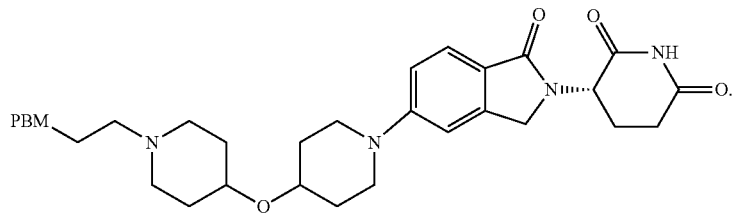
6. A compound, or a pharmaceutically acceptable salt, a solvate or a stereoisomer thereof, wherein the compound is any one of the following compounds:
| No. | Structural formula |
|---|---|
| Compound 1 | |
| Compound 3 | |
| Compound 5 | |
| Compound 8 | |

-continued
| No. | Structural formula |
|---|---|
| Compound 9 (free base) | 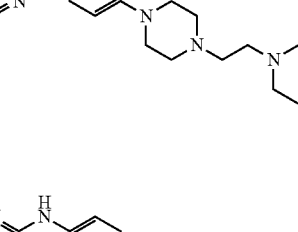 |
| Compound 10 | 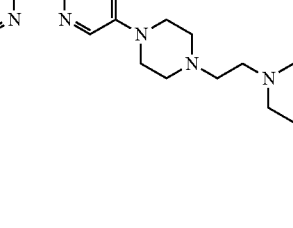 |
| Compound 12 (free base) | 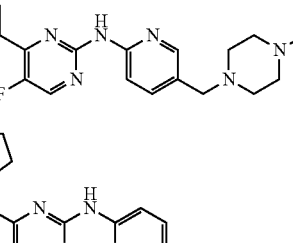 |
| Compound 13 | 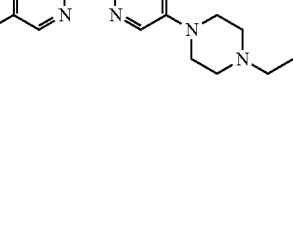 |
| Compound 15 | 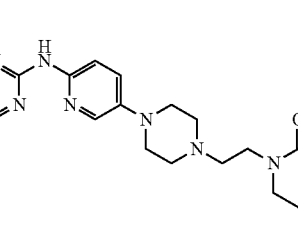 |
| Compound 16 | 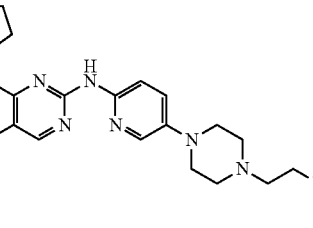 |

-continued

| No. | Structural formula |
|---|---|
| Compound 18 | |
| Compound 20 | |
| Compound 22 | |
| Compound 24 | |
| Compound 25 (free base) | |

| No. | Structural formula |
|---|---|
| Compound 26 (free base) | |
| Compound 27 (free base) | |
| Compound 28 (free base) | |
| Compound 29 (free base) | |
| Compound 30 (free base) | |

| No. | Structural formula |
|---|---|
| Compound 31 (free base) | |
| Compound 32 (free base) | |
| Compound 33 (free base) | |
| Compound 34 (free base) | |
| Compound 35 (free base) | |

-continued

| No. | Structural formula |
|---|---|
| Compound 36 (free base) | |
| Compound 37 (free base) | |
| Compound 38 (free base) | |
| Compound 39 (free base) | |
| Compound 40 (free base) | |
| Compound 41 | |

| No. | Structural formula |
|---|---|
| Compound 42 (free base) | [structure] |
| Compound 43 (free base) | [structure] |
| Compound 44 (free base) | [structure], and |
| Compound 45 (free base) | [structure]. |

7. A pharmaceutical composition comprising the compound according to claim 1, or a pharmaceutically acceptable salt, a solvate or a stereoisomer thereof.

8. A pharmaceutical preparation comprising the compound according to claim 1 or a pharmaceutically acceptable salt, a solvate or a stereoisomer thereof, and one or more pharmaceutically acceptable excipients.

* * * * *